US 9,345,759 B2

(12) United States Patent
Audonnet et al.

(10) Patent No.: US 9,345,759 B2
(45) Date of Patent: May 24, 2016

(54) BLUETONGUE VIRUS RECOMBINANT VACCINES AND USES THEREOF

(75) Inventors: Jean-Christophe Audonnet, Lyons (FR); Xuan Guo, Suwanee, GA (US); Kevin Cox, Raleigh, NC (US)

(73) Assignee: MERIAL, INC., Duluth, GA (US)

( * ) Notice: Subject to any disclaimer, the term of this patent is extended or adjusted under 35 U.S.C. 154(b) by 154 days.

(21) Appl. No.: 13/046,317

(22) Filed: Mar. 11, 2011

(65) Prior Publication Data

US 2011/0236420 A1 Sep. 29, 2011

Related U.S. Application Data

(60) Provisional application No. 61/313,164, filed on Mar. 12, 2010, provisional application No. 61/366,363, filed on Jul. 21, 2010.

(51) Int. Cl.
| | |
|---|---|
| A61K 39/15 | (2006.01) |
| C12N 15/46 | (2006.01) |
| C12N 15/82 | (2006.01) |
| A61K 39/12 | (2006.01) |
| A61K 39/00 | (2006.01) |

(52) U.S. Cl.
CPC .............. *A61K 39/15* (2013.01); *A61K 39/12* (2013.01); *C12N 15/8258* (2013.01); *A61K 2039/517* (2013.01); *A61K 2039/5252* (2013.01); *A61K 2039/552* (2013.01); *A61K 2039/55505* (2013.01); *A61K 2039/55561* (2013.01); *A61K 2039/55566* (2013.01); *A61K 2039/55577* (2013.01); *C12N 2720/12134* (2013.01)

(58) Field of Classification Search
None
See application file for complete search history.

(56) References Cited

U.S. PATENT DOCUMENTS

| | | | |
|---|---|---|---|
| 5,690,938 A | 11/1997 | Ermak et al. | |
| 5,833,995 A | 11/1998 | Roy et al. | |
| 2007/0280960 A1 | 12/2007 | Audonnet et al. | |

OTHER PUBLICATIONS

Athmaram et al (Vaccine, 24, p. 2994-3000, 2006).*
Sallieau et al (see GenBank accession ACJ65032.1).*
Rybicki (Drug Discovery Today, 14(1/2), p. 16-24, Jan. 2009).*
Walker et al (Plant Cell Rep, 24, p. 629-641, 2005).*
Stoger et al (Current Opinion in Biotechnology, 16(2), pp. 167-173, 2005).*
Lobato (Veterinary Immunology and Immunopathology, 59, pp. 293-309, 1997).*
Athmaram, TN, et al., (2006) "Integration and expression of bluetongue VP2 gene in somatic embryos of peanut through particle bombardment method", Vaccine 24: 2994-3000.
Spreull, J. (1905). "Malarial catarrhal fever (bluetongue) of sheep in South Africa." J. Comp. Path.. Ther. 18: 321-337.
Wilson, WC., et al., (2000). "Molecular Evolution of Orbiviruses." Proc USAHA 104: 169-180.
Bonneau, KR., et al. (2001). "Occurrence of genetic drift and founder effect during quasispecies evolution of the VP2 and NS3/NS3A genes of bluetongue virus upon passage between sheep, cattle, and Culicoides sonorensis." J Virol 75(17): 8298-305.
Anderson, G. A., J. L. Stott, et al. (1985). "Subclinical and clinical bluetongue disease in cattle: clinical, pathological and pathogenic considerations." Prog Clin Biol Res 178: 103-7.
MacLachlan, NJ. (1994). "The pathogenesis and immunology of bluetongue virus infection of ruminants." Comp Immunol Microbiol Infect Dis 17(3-4): 197-206.
White, DM., et al. (2005). "Studies on overwintering of bluetongue viruses in insects." J Gen Virol 86(Pt 2): 453-62.
Roy, P. (1996). "Orbivirus structure and assembly." Virology 216(1): 1-11.
Verwoerd, DW., et al. (1972). "Structure of the bluetongue virus capsid." J Virol 10(4): 783-94.
Hassan, SS., et al., (1999). "Expression and functional characterization of bluetongue virus VP2 protein: role in cell entry." J Virol 73(12): 9832-42.
Huismans, H. et al., (1981). "Identification of the serotype-specific and group-specific antigens of bluetongue virus." Onderstepoort J Vet Res 48(2): 51-8.
De Mattos, CA., et al. (1994). "Heterogeneity of the L2 gene of field isolates of bluetongue virus serotype 17 from the San Joaquin Valley of California." Virus Res 31(1): 67-87.
Demaula, CD., et al. (2000). "Changes in the outer capsid proteins of bluetongue virus serotype ten that abrogate neutralization by monoclonal antibodies." Virus Res 67(1): 59-66.
Roy, P., et al. (1990). "Recombinant virus vaccine for bluetongue disease in sheep." J Virol 64(5): 1998-2003.
Huismans, H., et al. (1987). "Isolation of a capsid protein of bluetongue virus that induces a protective immune response in sheep." Virology 157(1): 172-9.
Andrew, M., et al. (1995). "Antigen specificity of the ovine cytotoxic T lymphocyte response to bluetongue virus." Vet Immunol Immunopathol 47(3-4): 311-22.
Lobato, ZI.,et al. (1997). "Antibody responses and protective immunity to recombinant vaccinia virus-expressed bluetongue virus antigens." Vet Immunol Immunopathol 59(3-4): 293-309.
Chargelegue et al., "Transgenic Plants for Vaccine Production: Expectations and Limitations", Trends in Plant Science 2001, 6, 495-496.
Schillberg et al., "Opportunities for Recombinant Antigen and Antibody Expression in Transgenic Plants—Technology Assessment", Vaccine 2005, 23, 1764-1769.
Arntzen et al., "Plant-derived Vaccines and Antibodies; Potential and Limitations", Vaccine 2005, 23, 1753-1756.
Koprowski, "Vaccines and Sera Through Plant biotechnology", Vaccine 2005, 23, 1757-1763.
MacLachlan, NJ., et al., (2004). "Bluetongue: Prodeedings of the Third International Symposium.", Vet Italiana. 40: 1-730.

\* cited by examiner

*Primary Examiner* — David T Fox
*Assistant Examiner* — Stephen Uyeno
(74) *Attorney, Agent, or Firm* — Judy Jarecki-Black; Ruoyang Chen; Merial, Inc.

(57) ABSTRACT

The present invention encompasses BTV vaccines or compositions. The vaccine or composition may be a vaccine or composition containing BTV antigens. The invention also encompasses recombinant vectors encoding and expressing BTV antigens, epitopes or immunogens which can be used to protect animals, such as ovines, bovines, or caprines, against BTV.

16 Claims, 42 Drawing Sheets

Figure 1

| SEQ ID NO | Type | Description |
|---|---|---|
| 1 | DNA | BTV1 VP2 DNA prior to codon-optimization |
| 2 | DNA | BTV1 VP2 DNA optimized for mammalian expression (in pCG100) |
| 3 | DNA | BTV1 VP2 DNA optimized for duckweed expression (in MerD01-04) |
| 4 | protein | BTV1 VP2 protein |
| 5 | DNA | BTV1 VP2 DNA (optimized for mammalian expression) + c-myc (in pCG101) |
| 6 | protein | BTV1 VP2 protein + c-myc |
| 7 | DNA | BTV1 VP5 DNA prior to codon-optimization |
| 8 | DNA | BTV1 VP5 DNA optimized for mammalian expression (in pCG102) |
| 9 | DNA | BTV1 VP5 DNA optimized for duckweed expression (in MERD01-04) |
| 10 | protein | BTV1 VP5 protein |
| 11 | protein | BTV1 VP2 protein with GenBank accession No. ACB05467 |
| 12 | Protein | BTV1 VP2 protein with GenBank accession No. ACF37215 |
| 13 | Protein | BTV1 VP2 protein with GenBank accession No. ACF37216 |
| 14 | Protein | BTV1 VP2 protein with GenBank accession No. ACJ65032 |
| 15 | Protein | BTV1 VP2 protein with GenBank accession No. ACR58459 |
| 16 | Protein | BTV1 VP2 protein with GenBank accession No. CAA39322 |
| 17 | Protein | BTV1 VP2 protein with GenBank accession No. CAE51088 |
| 18 | Protein | BTV1 VP5 protein with GenBank accession No. ACB59233 |
| 19 | protein | BTV1 VP5 protein with GenBank accession No. ACB59234 |
| 20 | Protein | BTV1 VP5 protein with GenBank accession No. ACR58462 |
| 21 | protein | BTV1 VP5 protein with GenBank accession No. CAE52973 |
| 22 | protein | BTV1 VP5 protein with GenBank accession No. CAE52974 |
| 23 | protein | BTV1 VP5 protein with GenBank accession No. CAE52979 |
| 24 | protein | BTV2 VP5 protein with GenBank accession No. CAE52991 |
| 25 | protein | BTV1 VP5 protein with GenBank accession No. CAE53011 |
| 26 | DNA | Alpha amylase leader sequence |
| 27 | DNA | RbcS leader (Lemna gibba RbcS (SSU5B) leader sequence) |
| 28 | DNA | Aocs promoter |
| 29 | DNA | AmasPmas promoter |
| 30 | DNA | LmUBQ promoter (Lemna minor ubiquitin) |
| 31 | DNA | ADH1 intron |
| 32 | DNA | LmUBQ Intron (Ubi Intron 1) |

Figure 4

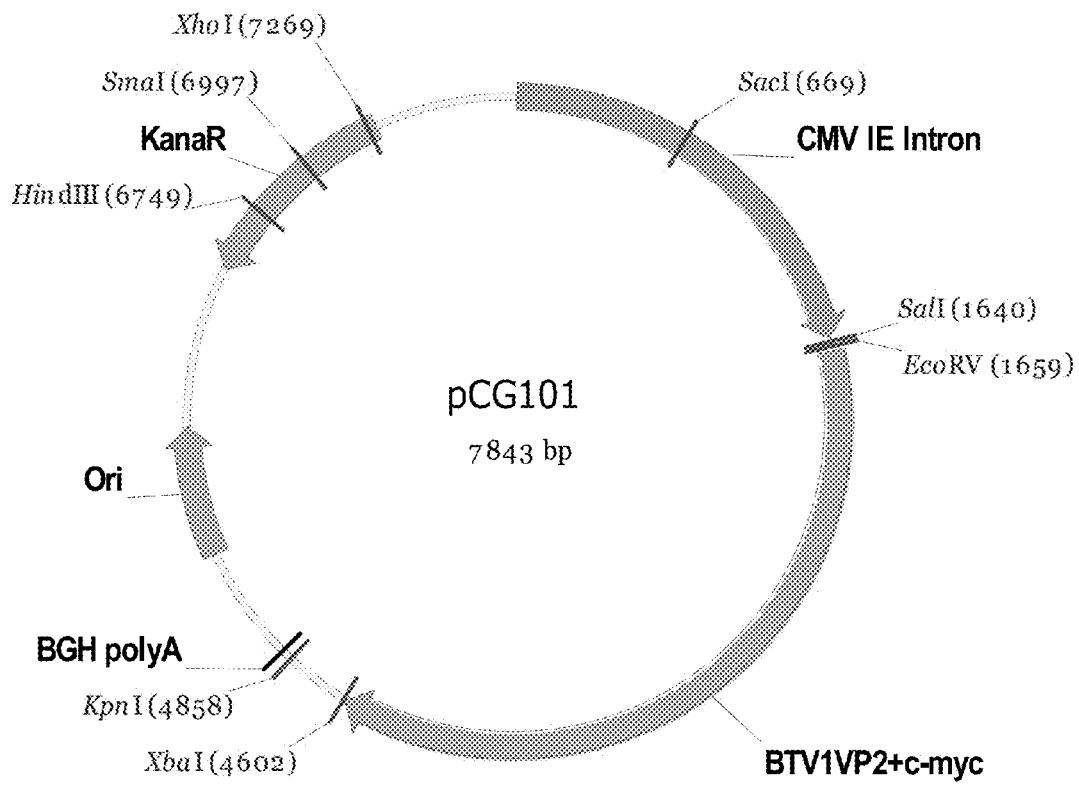

- Feature Map
  - CDS (2 total)
    - BTV1VP2+c-myc
      Start: 1676 End: 4594
      Original Location Description:
      1662..4600
    - KanaR
      Start: 6490 End: 7302 (Complementary)
      Original Location Description:
      complement(6490..7302)
  - PolyA Site (1 total)
    - BGH polyA
      Start: 4629 End: 5175
      Original Location Description:
      4629..5175
- Promoter Eukaryotic (1 total)
  - CMV IE Intron
    Start: 1 End: 1626
    Original Location Description:
    1..1626
- Replication Origin (1 total)
  - Ori
    Start: 5357 End: 5864
    Original Location Description:
    5357..5864

Figure 5

```
              pVR
              1012    pCG102
         M    C   S    C   S
200 kDa ___
120 kDa ___
100 kDa ___
 80 kDa ___
 60 kDa ___
 50 kDa ___
 40 kDa ___
 30 kDa ___
 20 kDa ___
```

1st Ab : mouse supernatant AHSV VP5 10AE12 (1/1000)

2nd Ab : anti-mouse IRDye800 1/10000

M : magic markTM XP western protein standard (Invitrogen)

1st Ab : mouse c-myc (1/1000)

2nd Ab : anti-mouse IRDye800 1/10000

M : magic markTM XP western protein standard (Invitrogen)

Figure 7a

|  | M1 | pVR1012 | pCG100 | pIV001 | pIV002 | pKM003 | pCG030 | pIV003 |
|---|---|---|---|---|---|---|---|---|

120 kDa
100 kDa
80 kDa
60 kDa
50 kDa
40 kDa
30 kDa
20 kDa

1st Ab : Pab BTV1 VP2 Rabbit L167 (1/100)
2nd Ab : anti rabbit IRDye800 au 1/5000
M1 : Magic mark XP (Invitrogen)

Figure 7b

1st Ab : Pab BTV1 VP2 Rabbit L168(1/100)
2nd Ab : anti rabbit IRDye800 au 1/5000
M1 : Magic mark XP (Invitrogen)

Figure 8A

```
                  1                                                  50
SEQ ID NO:3    (1) ATGGAGGAGCTGGGGATCCCGGTGTAGAAGCGCGGGTTCCCCGAGCAGCT
SEQ ID NO:2    (1) ATGGAGGAGCTGGGGATCCCGGTGTAGAAGAGAGGCTTCCCCGAGCAGCT
SEQ ID NO:1    (1) ATGGATGAGCTAGGGATCCCAGTTTATAACAGAGGATTTCCCGAACATCT 51                                                 100
SEQ ID NO:3   (51) GCTCCGGGGCTAGGAGTTGATGATGGAGGTGGGCACCAAGATGGAGTCGG
SEQ ID NO:2   (51) GCTGCGGGGCTAGGAGTTGATGATGGAGGTGGGCACCAAGATGGAGAGGG
SEQ ID NO:1   (51) GCTTCGTGGTTATGAGTTTATAATAGATGTTGGAACTAAGATAGAAAGTG 101                                                150
SEQ ID NO:3  (101) TGGGCGGGAGGCAGGAGGTGACCAAGATCCCGGAGATGAAGGCGTAGGAC
SEQ ID NO:2  (101) TGGGCGGCAGACAGGAGGTGACCAAGATCCCCGAGATGAAGGCGTAGGAC
SEQ ID NO:1  (101) TTGGTGGACGTCATGATGTAACGAAAATACCAGAAATGAATGCATATGAC 151                                                200
SEQ ID NO:3  (151) ATCAAGCAGGAGTCGATCGGGACGGCGGTCTGGTACAACCCGATCGGAA
SEQ ID NO:2  (151) ATCAAGCAGGAAAGGATCAGAACGGCGGTGTGGTACAACCCGATCAGAAA
SEQ ID NO:1  (151) ATCAAGCAGGAAAGTATCGGGACGGCATTATGGTATAACCCGATAAGAAA 201                                                250
SEQ ID NO:3  (201) GGAGGGCTTCGTGCTCCCGGCGGTCCTGGACATCACGGTCCGGGGGTACG
SEQ ID NO:2  (201) GGAGGGCTTCGTGCTGCCCAGAGTGCTCGACATCACGGTGAGGGGCTACG
SEQ ID NO:1  (201) TGATGGTTTTGTGTTGCCGGAGTGTTGGATATCACATTGAGGGGTTACG 251                                                300
SEQ ID NO:3  (251) AGGAGCGCGGGCGGTGGTCGAGTCGACGCGCCACAAGAGGCTTCCACACG
SEQ ID NO:2  (251) AGGAGAGAAGAGCCGTGGTGGAGAGCACCAGACACAAGAGCTTCCACACC
SEQ ID NO:1  (251) ATGAAAGACGGCGGTTGTTGAAAGTACGATACACAAGAGTTTCCACACG 301                                                350
SEQ ID NO:3  (301) AAGGACCAATGGGTGCAGTGGATGATGAAGGAGTCGATGGATGCGCAGCC
SEQ ID NO:2  (301) AAGGACCAGTGGGTGCAGTGGATGATGAAGGAGAGCATGGACGCCCAGCC
SEQ ID NO:1  (301) AATGACCAGTGGGTGCAGTGGATGATGAAAGATTCGATGGACGCTCAGCC 351                                                400
SEQ ID NO:3  (351) GCTGAAGGTCGGGCTGGAGGAGCAGTCGCGCAAGGTGGCGCACAGCGTCC
SEQ ID NO:2  (351) CCTGAAAGTGGGCCTGGAGGACCAGAGGCAGAAAGTGGCGCACAGCGTGC
SEQ ID NO:1  (351) TTTAAAGGTTGGGTTAGATGAGCAAAGTAGAATGTGGCTCACTCGTTAC 401                                                450
SEQ ID NO:3  (401) AGAAGTGCGTCGTGAAGATCGACAGCAAGAAAGCGGACACGATCGTGTAG
SEQ ID NO:2  (401) AGAAGTGCGTGGTGAAGATCGACAGCAAGAAAGCCGACACCATGAGCTAG
SEQ ID NO:1  (401) ATAATTGCGTAGTCAAAATCGATTCGAAGAAGGCTGATACTATGTCTTAT 451                                                500
SEQ ID NO:3  (451) CAGGTCGAGCCGATCGAGGACGCGCTCCAAGGGGTGGCTCCACACCCGCAC
SEQ ID NO:2  (451) CAGGTGGAGCCCATCGAGGACGCGCAGCAAGGGCTGCCTGCACACCACAAC
SEQ ID NO:1  (451) CATGTAGAGCCGATTGAGGACGCGTCAAAGGGGTGTTTGCATACGACAAC
```

Figure 8B

```
                         501                                                       550
SEQ ID NO:3      (501)   GATGATGTGGAACCACCTGGTCCGCATGGAGACCTTCCAGGCGGCGCAGG
SEQ ID NO:2      (501)   CATGATGTGGAACCACCTGGTGCGGATCGAGACATTCCAGGCCGCGCAGG
SEQ ID NO:1      (501)   CATGATGTGGAATCACCTAGTACGAATAGAAACATTTCATGCAGCACAGG 551                                                       600
SEQ ID NO:3      (551)   AGGTCGCGTACACCCTCAAGCCGACCTACGACATCGTGGTCCACGCGGAG
SEQ ID NO:2      (551)   AAGTGGCCTACACCCCGAAGCCCACCTATGACATCGTGGTGCACGCCGAG
SEQ ID NO:1      (551)   AGGTGGCATATACTCTTAAACCTACTTATGATATCGTGGTCCACGCTGAA 601                                                       650
SEQ ID NO:3      (601)   CGCAGAGACGCTCGCAGCCGTTCAGACCGGGGAGCAGACGGTGATCAA
SEQ ID NO:2      (601)   CGGAGAGACAGAAGGCAGCCCTTCAGACCGGGCAGCAGACCGTGATCAA
SEQ ID NO:1      (601)   AGGAGAGATCGTAGTCAACCGTTTAGGCCGGGGATCAGACATTAATTAA 651                                                       700
SEQ ID NO:3      (651)   CTTCGGCAGGCGGCAGAAGGTGACGATGAATCACAACAGCTACGACAAGA
SEQ ID NO:2      (651)   CTTCGGCAGAGGCCAGAAAGTGACGATGAACCACAACAGCTACGACAAGA
SEQ ID NO:1      (651)   TTTTGGGAGAGGTCAGAAGGTGACGATGAACCACAATTCATATGATAAGA 701                                                       750
SEQ ID NO:3      (701)   TGGTCGAGGGGCTCGCGCAGCTCGTGATCCGCGGAAGATCCCGAGGTC
SEQ ID NO:2      (701)   TGGTGGAAGGCCTGGCCCAGCTGGTGATCAGAGCAAGATCCCTGAGCTG
SEQ ID NO:1      (701)   TGGTTGAGGGATTAGCGCATTTACTGATTACAGCGAAATTCAGAGGTG 751                                                       800
SEQ ID NO:3      (751)   ATCGCGGACGATATGCCCTCCCTGGACGAGATCCTGAACAGGTGGATCCA
SEQ ID NO:2      (751)   ATCCCGGACGACATTGCCAGCCTGGACGAGATCCTGAACAGATGGATTCA
SEQ ID NO:1      (751)   ATTAGAGATGATATCGCTAGCTTGGATGAGATATGTAATAGGTGGATACA 801                                                       850
SEQ ID NO:3      (801)   GAGCCGCCACGACCCGGCGAGATCAAGGCCTACGAGCTGTGGAAGATCG
SEQ ID NO:2      (801)   GAGCCGGCACGACCCCGGCGAGATCAAGGCCTACGAGCTGTGGAAGATCG
SEQ ID NO:1      (801)   GAGTAGGCACGACCCTGGAGAAATAAAGGCATATGAACTATGTAAATAT 851                                                       900
SEQ ID NO:3      (851)   TCAGCACCATCGGCGCCAAGGTCCTGGACAGGCAGAAACAGCCCGAGGAG
SEQ ID NO:2      (851)   TGAGCACCATCGGCCACAAAGGTGCTGGACACACAGAAAGAGCCCGAGGAC
SEQ ID NO:1      (851)   TATCAACGATCGGTCCAAAAGTTCTCGATCGAGAGAAAGAACCAGAGGAT 901                                                       950
SEQ ID NO:3      (901)   GAGGCCTCCCTCTGCATCCGCTTGCAGGAGGCGATCGACAACAAGTTCGG
SEQ ID NO:2      (901)   GAGGCCAGCCTGAGCATCAGATTGCAGGAAGCCATCGACAACAAGTTCAG
SEQ ID NO:1      (901)   GAGGCAAGTCTATCGATCCGATTTCAAGAGGCGATCGACAATAAGTTCGG 951                                                      1000
SEQ ID NO:3      (951)   CCAGCACGACCCGGAGAGGCTGAAGATCTTCGAACAGCCGAACCAGCCGG
SEQ ID NO:2      (951)   ACAGCACGACCCTGAGAGACTGAAGATCTTCGAGCACAGAAAGCAGCCGG
SEQ ID NO:1      (951)   ACAACATGATCCTGAGCCGCCTGAAGATATTTGAGCATAGGAATCAGCGTA 1001                                                     1050
SEQ ID NO:3      (1001)  GCGACGAGGAGACAGATTCTAGATGCTCCTGATGATGGCGGTGCGACACG
SEQ ID NO:2      (1001)  GGGACGAGGAGACAGATTCTAGATCCTGGTGATGATGGCGGCAGCGACACC
SEQ ID NO:1      (1001)  GAGATGAGGATCGGTTCTATATTCTGTTGATGATTGCAGCCGCGACACT
```

```
              1601                                              1650
SEQ ID NO:3  (1601) AGGAGCAAATCGCCCAGGGCCAGTCGGACGACCCGATGGTTAAGAGGACC
SEQ ID NO:2  (1601) AGCAGCAAATCGCCCAGAGACAGAGCCAGGACCCGATGGTGAAGAGAACC
SEQ ID NO:1  (1601) ATGAAGAGATTGGCGCAGGGTCAAAGTGATGACCCGATGGTAAAACGTACT 1651                                              1700
SEQ ID NO:3  (1651) GTCTGGCCGATGACCGCGGAGCCCGATCGAGCTGCAGCGGTCACCCTGGC
SEQ ID NO:2  (1651) GTGAGCCCGATGACCGCGGAGCCCGATCGAGCTGCAGAGACTGACCCTGGC
SEQ ID NO:1  (1651) TTATCACCTATTACCGCAGATCCAATCGAATTACAAAATTGACTTTGGC 1701                                              1750
SEQ ID NO:3  (1701) GCGCTTGTACGACATGGCCCTGCTGTCGGGGGCCAGGCCCTGAGCGGCC
SEQ ID NO:2  (1701) CAGATTGTACGACATAGACCAGCCTGCGGGGGCAGGCTCTGAGCACAAC
SEQ ID NO:1  (1701) GGGATTTTACGACATTGGTCCGCTTAAGAGGACAGGCACTTTCGGGAC 1751                                              1800
SEQ ID NO:3  (1751) AGCAGGCCCAGAGCACCTACGACGAGGAGATCGCCAAGCGCCAGGAGTAC
SEQ ID NO:2  (1751) AGCAGGCCCAGAGCACCTACGACGAAGAGATCAGCAAGGACACAGGACTAC
SEQ ID NO:1  (1751) AACAGGCACAGTCCACTTACGACGAAGAGATAGCGAAAACACAGGATTAT 1801                                              1850
SEQ ID NO:3  (1801) GCCGACATCGTCAAGGCGGAGGGGATCGTGCAGATCCCGAAGAAGCCCTG
SEQ ID NO:2  (1801) GCCGACATCGTGAAGAGAAGAGGCATCGTGCAGATCCCGAAGAAGCCCTG
SEQ ID NO:1  (1801) GCAGAGATATTGAAAGGTCGTGGAATTGTGCAAATTCCAAAGAAACCTTG 1851                                              1900
SEQ ID NO:3  (1851) CCCGACGGTGACGGCCCAGTACACCGTCGAGGGCTACGCGGTCTTCATCA
SEQ ID NO:2  (1851) CCCCACCGTCACGGCCCAGTACACCGTGGAAAGATACGCCGTGTTCATCA
SEQ ID NO:1  (1851) CCCAACAGTAACGGCCCAGTATACGTTGGAAGGTTATCCTTGTTCATTA 1901                                              1950
SEQ ID NO:3  (1901) TCAGCCATCCTGCAGCAGCACGTCGTCCGCGAGTGCGACGAGGAGGCGGTT
SEQ ID NO:2  (1901) TCAGCCATCCTGCAGCAGCACGTGGTGCGGGACTGCGACGAGGAAGCGGTG
SEQ ID NO:1  (1901) TCAGTATCCTACAACAGCATGTAGTACGAGATTGCGACGAGCAGGCGGTA 1951                                              2000
SEQ ID NO:3  (1951) TACGAGCACCCGGAAGGCGGGACCAGGAGCTGGAGATCTTCGGGAGTCCAT
SEQ ID NO:2  (1951) TACGAGCACCCCAAGGCCGACCAGGAGCTGGAAATCTTCGGCGAGAGCAT
SEQ ID NO:1  (1951) TACGAACATCCGAAAGCGGACCATGAACTTGAAATATTTGGCGAGAGCAT 2001                                              2050
SEQ ID NO:3  (2001) GGTGGACATCTCCCAGGTCATGATCCTCGGCGTTGACCTGATGTTCGAGC
SEQ ID NO:2  (2001) GGTGGACATCTCTCAGGTGATCATCCTGGCCTTGACCTGATGTTCGAGA
SEQ ID NO:1  (2001) TGTGGATATCTCTCAAGTGATTATTCAGCTTTTGACTTGATATTCGAGA 2051                                              2100
SEQ ID NO:3  (2051) GGCCCAGACGCGTGCCGACGTCTACGAGAGCGGCACATGATCGCCGGC
SEQ ID NO:2  (2051) GAAGGCCGACAGTGCCGGACGTGTACGAGAGCAGACACATGATTGCCAGA
SEQ ID NO:1  (2051) GAAGAGCAGGCTTACAGATGTGTATGAATCGCGGCACATAATTGCCGGT 2101                                              2150
SEQ ID NO:3  (2101) ATCCGCCGGATGCGGGGCAAGGAGATACTCAACGTGATCGCCGAGTTCTT
SEQ ID NO:2  (2101) ATCGAAGAATGCGGGGCAAAGAACGGCTGAACGTGATCGCCGAGTTCTT
SEQ ID NO:1  (2101) ATTAGGAGAATGCGAGGTAAAGAAAGATTGAACGTGATCGCGGAGTTTTT
```

Figure 8E

```
                    2151                                                      2200
SEQ ID NO:3  (2151) CCCGACTTACGGCGGGCTGCTCAATGGCCTGAACTCCGCTACCGTCGTGC
SEQ ID NO:2  (2151) CCCCACCGTAGGGCGGCCTGCTGAACGGCCTGAACAGCGCCACCGTGGTGC
SEQ ID NO:1  (2151) CCCAACGTATGGGGGTCTTCTAAATGGTTAAACAGCGCCACCGTAGTGC 2201                                                      2250
SEQ ID NO:3  (2201) AGAACATCATGTACCTCAACTTCCTGCCGCTCTACTTCCTGGTCGGCGAC
SEQ ID NO:2  (2201) AGAACATCATGTACCTGAACTTTCTGCCCCTGTACTTCCTGGTGGGCGAC
SEQ ID NO:1  (2201) AGAATATTATGTATTTAAACTTCCTCCCATTGTATTTTTGGTAGGCGAT 2251                                                      2300
SEQ ID NO:3  (2251) AACATGATCTACTGCCACCGCCAGTGGTCCATCCCGCTGCTCCTGTACAC
SEQ ID NO:2  (2251) AACATGATCTACAGCCACGACAGTGGAGCATCCCCGTGCTGCTGTACAC
SEQ ID NO:1  (2251) AACATGATATACTGTCATAGGCAGTGGTCTATTCCTTTACTTCTATATAC 2301                                                      2350
SEQ ID NO:3  (2301) CCACGAGGTGATGGTCGTGCCGGTCGAGGTGGGCTCCTATAACGACGGCT
SEQ ID NO:2  (2301) CCACGAAGTCATCGTGCTGCCCTGTGGAAGCTGCCAAGCTACAACGACAAT
SEQ ID NO:1  (2301) TCATGAAGTGATCGTGCTCCCATTACAAGTTGGTTCATACAATGATCGT 2351                                                      2400
SEQ ID NO:3  (2351) GCGGGCTCATCGCCTACCTCGAGTACATGGTCTTCTTCCCTTCCAAGGCG
SEQ ID NO:2  (2351) GCGGGCCTGATCGCCTACCTGGAATACATGGTGTTCTTGCCTAGCAAGGCC
SEQ ID NO:1  (2351) GCGGATTAATTGCGTACCTGGAATACATGGTTTTCTTTCCCTCAAAGGCG 2401                                                      2450
SEQ ID NO:3  (2401) ATCAGATTCTCCAAGCTCAAGGAGGCCCAGCCGAAGATCGCTCGGAGAT
SEQ ID NO:2  (2401) ATCAGATTCAGCAAGCTGAAGGAGGCCCAGCCGAAGATCGCCAGAGAGAT
SEQ ID NO:1  (2401) ATTCGATTTAGCAAACTGAATGAAGCGCAGCCCAAGATTGCAGGCGAGAT 2451                                                      2500
SEQ ID NO:3  (2451) GCTCAAGTACTACGCGAACACGACCGTGTACGACGGCGGGTGAACTACA
SEQ ID NO:2  (2451) GCTGAAGTACTACGCCAACACCACCGTGTACGACGGCGGCGTGAACTACA
SEQ ID NO:1  (2451) GCTTAAGTACTACGCTAATACTACGGTATATGATGGGGAGTCAACTACA 2501                                                      2550
SEQ ID NO:3  (2501) ACGTCGTGACCACCAAGCAGCTCCTGTACGAGACGTACCTGGCCAGCCTC
SEQ ID NO:2  (2501) ACGTGGTGACCACCAAGCAGCTGCTGTACGAGACATACCTGGCCAGCCTG
SEQ ID NO:1  (2501) ACGTCGTGACGACGAAGCAGCTTCTATATGAGACATATCTCGCTTCGTTA 2551                                                      2600
SEQ ID NO:3  (2551) TGGGCGGGGATCTCGGACGGTATCGTGTGGTATCTGCCGATCACCCACCC
SEQ ID NO:2  (2551) TGGGCGGGCATCAGCGACGGCATCGTGTGGTATCTGCCCATCACCCACCC
SEQ ID NO:1  (2551) TGTGGGGGTATTTCTGATGGTATTGTCTGGTATTTACCGATCACACATCC 2601                                                      2650
SEQ ID NO:3  (2601) CAACAAGTGCATCGTCGCCCATCGAGGTGTCGACGAGCGGCTGCCGCCT
SEQ ID NO:2  (2601) CAACAAGTGCATCGTGGCCATCGAGGTGTCGACGAGAGAGTGCCGCCA
SEQ ID NO:1  (2601) GAACAAATGCATTGTAGCGATCGAGGTATCTGATGAAAGCAGTTCCGGCTA 2651                                                      2700
SEQ ID NO:3  (2651) CGATCACAGCGGGCCCATCCGCCTCCGCTTGCCCCTGAGCGCCCGCCAG
SEQ ID NO:2  (2651) GCATCACGGCCGGCAGAATCAGACTGACATTCCCCTGAGCGCCACAGAG
SEQ ID NO:1  (2651) GCATTACAGCGGGGCGTATAAGCTAAGATTTCCGCTGAGCGCGGGACAT
```

Figure 8F

```
                   2701                                               2750
SEQ ID NO:3  (2701) CTCAAGGCGGTCGTGATCATCCAGATGGAGGAGGAGGGGGAGTTGACGGT
SEQ ID NO:2  (2701) CTGAAGGCGGTGGTGATCATTCAGATGGACGAAGAGGGGGAGTTGACCGT
SEQ ID NO:1  (2701) CTAAAAGGGGTTGTAATCATACAAATTGATGAGGAGGGCGAATTTACAGT 2751                                               2800
SEQ ID NO:3  (2751) GTAGTGGGAGGGGATGGTGTCGCAGGGGGTGTGGAAGAAGAAGCTGCTGA
SEQ ID NO:2  (2751) GTAGTGGGAGGGGATGGTGTCGCAGAGAGTGTGGAAGAAGAACCTGCTGA
SEQ ID NO:1  (2751) GTATAGCGAGGGGATTGTGTCTCATCGGGTGTGTAAAAAGAATTTACTGA 2801                                               2850
SEQ ID NO:3  (2801) AGTACATGTGCGAGATGATCGTGCTCAAGTTCTCGGGCACGTCTTGGGC
SEQ ID NO:2  (2801) AGTATATGTGCGACATGATTCTGCTGAAGTTCAGCGGGCACGTGTTGGC
SEQ ID NO:1  (2801) AGTATATGTGCGATATTATATTACTGAAGTTTTCCGGGCACGTTTTTGGT 2851                     2886
SEQ ID NO:3  (2851) AACGACGAGATGCTGACGAAGCTCCTGAACGTGTAA
SEQ ID NO:2  (2851) AACGACGAGATGCTGACGAAGCTGCTGAACGTGTGA
SEQ ID NO:1  (2851) AACGACGAGATGCTGACAAAACTTCTCAACGTATGA
```

Sequence identity percentage (using Vector NTI software, ClustalW algorithm)

|            | SEQ ID NO:1 | SEQ ID NO:2 | SEQ ID NO:3 |
|------------|-------------|-------------|-------------|
| SEQ ID NO:1 | 100%       | 74%         | 73%         |
| SEQ ID NO:2 |             | 100%        | 87%         |
| SEQ ID NO:3 |             |             | 100%        |

Figure 9A

```
                      1                                                  50
SEQ ID NO:9    (1)    ATGGGGAAGGTGATCCGCTCCCTCTCCCGCTTCGGCAAGAAGGTCGGCAA
SEQ ID NO:8    (1)    ATGGGCAAGGTGATCAGAAGCCTGAGCAGATTCGGCAAGAAGGTGGGCAA
SEQ ID NO:7    (1)    ATGGGTAAAGTCATACGGTCCTTAAGCCGATTTGGCAAGAAGGTGGGCAA 51                                                 100
SEQ ID NO:9    (51)   CGCCCTCACGTCCAAGACCGCCAAGAAGATCTACTCGACGATCGGCAAGG
SEQ ID NO:8    (51)   CGCTCTGACCAGCAAGACCGCCAAGAAGATCTACAGCACCATCGGCAAGG
SEQ ID NO:7    (51)   CGCGTTAACCTCTAATACCGCAAAAAAGATCTATAGTACAATCGGAAAAG 101                                                150
SEQ ID NO:9    (101)  CCGCGGAGCGCTTCGCCGACAGCGAGATCGGGTCCGCGGCGATCGAGGGG
SEQ ID NO:8    (101)  CTGCCGAAAGATTCGCCGACAGCGAGATCGGCAGCGCGGCCATCGAGGGC
SEQ ID NO:7    (101)  CGGCGGAACGATTCGCTGAGAGTGAGATAGGTTCAGCGGCGATCGATGGA 151                                                200
SEQ ID NO:9    (151)  CTCGTCCAGGGCAGCGTCCACTCGATCATCACGGGCGAGTCCTACGCCGA
SEQ ID NO:8    (151)  CTGGTGCAGGGAAGCGTGCACAGCATCATCACCGGAGAGAGCTACGGAGA
SEQ ID NO:7    (151)  TTGGTACAGGGGACGCGTACATTCAATCATAACGGGCGAATCTTACGGCGA 201                                                250
SEQ ID NO:9    (201)  GTCGCTGAAGCAGGCCGTGCTGCTCAAGGTCCTGGCGTCCGCGGAGGAGA
SEQ ID NO:8    (201)  GAGCCTGAAGCAGGCCGTGCTGCTGAAGCTGCTGGCCAGCGCGGAGGAGA
SEQ ID NO:7    (201)  ATCTGTGAAACAAGCTGTGTTGTTAAATGTGTTGGCGAGTGGTGAGGAAA 251                                                300
SEQ ID NO:9    (251)  TCCCGGACCCTCTCTCGCCGGGCGAGAGGGGCATCCAGGCGAAGCTCAAG
SEQ ID NO:8    (251)  TCCCCGACCCCTGAGCCCTGCCGACAGCGGCATCCAGCCAAGCTGAAA
SEQ ID NO:7    (251)  TTCCTGATCCGCTAAGCCCAGGAGAGCCGGGGATACAAGCTAAGTTGAAA 301                                                350
SEQ ID NO:9    (301)  GAACTCGAGGACGAGCAGAAAAATGAGCTGGTGCCGCTGAAGTACAACGA
SEQ ID NO:8    (301)  GAACTGGAAGATCAGCAGAGGAACGAGCTGGTGCCGGTCAAGTACAACGA
SEQ ID NO:7    (301)  GAGTTAGAGGATGAGCAACGTAATGAATTAGTTCGCTTGAAATATAATGA 351                                                400
SEQ ID NO:9    (351)  CAAGATCAAGGAGAAATTCGGGAAGCAACTCGAGGAAGTGTACAAGTTCA
SEQ ID NO:8    (351)  CAAGATCAAGGAGAAGTTCGGCAAGCAACTGGAAGAGGTCTACAAGTTCA
SEQ ID NO:7    (351)  TAAGATTAAGGAGAAATTTGGAAAAGAGCTTGAGGAGGTGTACAATTTTA 401                                                450
SEQ ID NO:9    (401)  TGAACGGCGAGGCCAAGGCCGGAGATCGAGGATGAGAAGCAGTTCGACATC
SEQ ID NO:8    (401)  TGAACGGCGAGGCCAAGGCCGAGATCGAGGACGAGAAGCAGTTCGACATC
SEQ ID NO:7    (401)  TGAATGGGGAGGCGAATGCTGAGATTGAAGATGAGAAGCAGTTTGATATA 451                                                500
SEQ ID NO:9    (451)  CTGAACAAGGCCGTGACCAGCTACAACAAGATCCTCACGGAGGAGGAGCCT
SEQ ID NO:8    (451)  CTGAACAAGGCCGTGACCAGCTACAACAAGATCCTGACCGAGGAGGAGCCT
SEQ ID NO:7    (451)  TTGAACAAGGCCGTGACCTCGTATAACAAAATCCTTACGGAAGAAGATCT
```

Figure 9B

```
                       501                                                550
SEQ ID NO:9     (501)  GCAAATGCCAGACTCGCCACGGCCCTGCAGAAGGAGATCGGGGAGCGGA
SEQ ID NO:8     (501)  GCAGATGAGAAGGCTGGCCACGGCCCTGCAGAAGGAGATCGGCGAGAGGA
SEQ ID NO:7     (501)  ACAGATGCGCCGGCTAGCTACGGCGTTACAGAAGAGATCGGAGAAGAA 551                                                600
SEQ ID NO:9     (551)  CTCAGGCGGAGACCGTGATGGTGAAGGAGTATCGCGACAAGATGGACGCG
SEQ ID NO:8     (551)  CCCAGGCGGAGACAGTGATGGTGAAGGAGTACAGGGAGAAGATGGACGCC
SEQ ID NO:7     (551)  CACATGCGGAGACGGTCATGGTAAAAGAATACGAGATAAAATTGACGCT 601                                                650
SEQ ID NO:9     (601)  CTGAAGAACGCCATCGAGGTCGAGACGGACGGGATGCAGAGGAGGCCAT
SEQ ID NO:8     (601)  CTGAAGAACGCCATCGAGGTGGAGACGGACGGCATGCAGAGGAGGCCAT
SEQ ID NO:7     (601)  TTAAAAAATGCGATTGAGGTAGAAAGAGATGGCATGCAAGAGGAGGCAAT 651                                                700
SEQ ID NO:9     (651)  CCAGGAGATCGCCGGCGATGACCGCGGAGGTGCTCGAGGCCGCGAGCGAGG
SEQ ID NO:8     (651)  TCAGGAAATCGCCGGCATGACCGCCGAGGTGCTGGAGGCTGCCAGGGAGG
SEQ ID NO:7     (651)  ACAGGAGATTGCGGCGATGACCGCAGATGTGTTAGAGGCGGCATCGGAGG 701                                                750
SEQ ID NO:9     (701)  AGGTGCCGCTGATCGGCGCCGGGATGGCCACGGCCGTCGCCACGGGCGCC
SEQ ID NO:8     (701)  AGGTGCCGCTGATCGGAGCTGGAATGGCTACGGCTGTGGCCACGGGCACA
SEQ ID NO:7     (701)  AGGTTCCGCTGATTGGTGCGGCGATGGCTACGGCTGTAGCGACAGGAACA 751                                                800
SEQ ID NO:9     (751)  GCTATCGAGGCGGCGTACAAGCTGAAGAAGGCTCATCAACGCGCTCAGCGG
SEQ ID NO:8     (751)  GCCATCGAGGCGGCGTACAAGCTGAAGAAGGCTGATCAACGCTCTGTCGG
SEQ ID NO:7     (751)  GCTATAGAAGGAGCGTATAAACTCAAAAAGGTGATTAACGCTCTAAGCGG 801                                                850
SEQ ID NO:9     (801)  CATCGAGCTCACCGACCTCACGAACCCCGAAGATCGAGCCGTCCGTGGTCT
SEQ ID NO:8     (801)  CATCGAGCTGACCGACCTGAGGACCCCCAAGATCGAGCCAGCGTGGTGT
SEQ ID NO:7     (801)  GATCGATCTAACGCATTTGCGCACCCCGAAAATCGAACCTAGTGTTGTTT 851                                                900
SEQ ID NO:9     (851)  CGACCATGCTCGAGTACGGGACGAAGGAGATGCCCGAGAACGCGCTGGCG
SEQ ID NO:8     (851)  CCACCATGCTGGAGTACAGGACGAAGCAGATGCCTGAGAACGCGCTGGCG
SEQ ID NO:7     (851)  CAACTATTCTTGAGTACGGCACAAAGGAAATTCCTGATAACGCTCTAGCT 901                                                950
SEQ ID NO:9     (901)  GTTAGCGTCCTGTCGAAGAACGGGCCATCCAGGAGAACCACAAGGAGCT
SEQ ID NO:8     (901)  GTGACGGTGCTGTCCAAGAACAGAGCCATTCAGGAAAACCACAAGGAACT
SEQ ID NO:7     (901)  GTTAGTGTTCTATCAAAAATGCGCGGATTCAAGAAAACCACAAGGAACT 951                                               1000
SEQ ID NO:9     (951)  GATGCAGATCAAGAACGAGATCGCTCCCCGGTTGAAGAAGCCGATGGAGG
SEQ ID NO:8     (951)  GATGCAGATCAAGAACGAGATCCTGCCAAGGTTCAAAAAGCCGATGGACG
SEQ ID NO:7     (951)  GATGCATATCAAGAATGAGATATTACCTAGGTTTAAGAAAGCGATGGATG
```

Figure 9C

```
                   1001                                              1050
SEQ ID NO:9  (1001) AGCAGAAGGAGATCTGGGGATCGAGGACAAAGTGATCCACCCGAAGGTG
SEQ ID NO:8  (1001) AGGAGAAGGAGATCTGGGGATCGAGGACAAGGTGATCCACCCCAAGGTG
SEQ ID NO:7  (1001) AAGAAAAGGAAATATGTGGATAGAAGACAAAGTGATCCACCCGAAGGTG 1051                                              1100
SEQ ID NO:9  (1051) ATGATGAAGTTCAAGATGCCCGCGCTCAGCAGCCGCAGATCCAGGTCTA
SEQ ID NO:8  (1051) ATGATGAAGTTCAAGATGCCCCAGGCCCAGCAGCCGCAGATCCAGGTGTA
SEQ ID NO:7  (1051) ATGATGAAGTTCAAGATTCCGAGAGCTCAACAGCCGCAGATTCATGTATA 1101                                              1150
SEQ ID NO:9  (1101) CTCGGCGCCGTGGGAGTGGGAGCAGGTCTTCTTCTTGCAGTGGATCGGC
SEQ ID NO:8  (1101) CAGCGCCCCGTGGGAGAGGGAGCAGGTGTTCTTCTTGCAGTGGATCAGGC
SEQ ID NO:7  (1101) CAGTGCTCCATGGGATGGTGATGATGTGTTCTTCTTTCATTGTATCGGC 1151                                              1200
SEQ ID NO:9  (1151) ACCAGCACGCCAAGGAGTCCTTCTTGGTCGGGTTCGACGTGTCCATGGAG
SEQ ID NO:8  (1151) ACCAGCACGCCAAGGAGTCTTTCTTGGTGGGGTTCGACGTGTCCATGGAG
SEQ ID NO:7  (1151) ACCATCATGCAAATGAGTCGTTCTTTTAGGTTTCGATTTGAGCATTGAT 1201                                              1250
SEQ ID NO:9  (1201) CTGGTCCAGTACGAGGAGCTCACCGCGCAGTGGCAGGCTGTGGGTGCCGC
SEQ ID NO:8  (1201) CTGGTGCAGTACGAGGAGCTGACCGCGCAGTGGCAGGCCCTGGGAGCCGC
SEQ ID NO:7  (1201) TTAGTTCATTATGAAGATCTTACCGCGCATTGGCATGCATTGGGAGCAGC 1251                                              1300
SEQ ID NO:9  (1251) GCAGGCGGCTGCCGGGGGGACCGTCACCGAGGCCTACCGCGAGTTCCTCA
SEQ ID NO:8  (1251) TCAGGCGGCTGCTGGCAGAACCGTGACCGAGGCCTACAGAGAGTTCCTGA
SEQ ID NO:7  (1251) TCAAGCAGCGGCGGGAGTACGTTGACTGAAGCGTATAGAGAATTTTTAA 1301                                              1350
SEQ ID NO:9  (1301) ACGTGGCCATCAGCAAGGCGTTCGGCACGCAGATGCACACGCGGGCCTG
SEQ ID NO:8  (1301) ACGTGGCCATCAGCAAGGCCTTCGGCACCCAGATGCACACCAGGCCGCTG
SEQ ID NO:7  (1301) ATTTGGCGATCTCAAATGCATTCGGCACGCAAATGCACACGAAGTTG 1351                                              1400
SEQ ID NO:9  (1351) GTGAGGAGCAAAACGGTGCAGCCGATCTACCTGGCCAGCCTCCAGTACGA
SEQ ID NO:8  (1351) GTGCGGAGCAAGACCGTGCAGCCCATCTACCTGGCCAGCCTGCACTACGA
SEQ ID NO:7  (1351) GTTAGGTCAAAAACGGTACATCCAATTATTTAGGTTCCTTGCATTACGA 1401                                              1450
SEQ ID NO:9  (1401) GATCAGCTTCTCGGAGCTGGGCGGAACGCGCAGCGGATGGTGTAGGAGG
SEQ ID NO:8  (1401) GATCAGCTTCAGCGAGCTGAGAAGCAACGCGCAGAGGATGGTGTAGGAGG
SEQ ID NO:7  (1401) TATTTCCTTTTGGATCTGGGTGCAAACGCTCAGAATAGTTTATGATG 1451                                              1500
SEQ ID NO:9  (1451) AGGAGCTGCAGATGCACATGCTGGCGCGGCCCATGCACTTGCAGCGCCGC
SEQ ID NO:8  (1451) AGGAGCTGCAGATGCACATGCTGAGGGCGCCCATGCACTTGCAGAAAAG
SEQ ID NO:7  (1451) ATGAGCTGCAAATGCACATACTGGGTGGCCGATACACTTTCAAAAGCT
```

Figure 9D

```
             1501                                                      1550
SEQ ID NO:9  (1501) GCGATGCTCGGGCCGCTCAAGTTGGGTGCAAGGTGCTCGGTGACGGCCT
SEQ ID NO:8  (1501) GCGATGCTGGGCGCCCTGAAGTTGGCTGCAAGGTGCTGGCGACAGGCT
SEQ ID NO:7  (1501) GCAATACTGCCAGCTTGAAATTTGATGTAAGGTTTGCGGCACGGTTT 1551          1581
SEQ ID NO:9  (1551) CGACGTGCCGCTGTTCGTCGGCAAGGCGTAA
SEQ ID NO:8  (1551) GGACGTGCCGCTGTTCGTGAGGAAGGCGTGA
SEQ ID NO:7  (1551) AGACGTACCACTCTTCTTAGGAAATGCTTGA
```

Sequence identity percentage (using Vector NTI software, ClustalW algorithm)

|            | SEQ ID NO:7 | SEQ ID NO:8 | SEQ ID NO:9 |
|------------|-------------|-------------|-------------|
| SEQ ID NO:7 | 100%       | 73%         | 73%         |
| SEQ ID NO:8 |             | 100%        | 87%         |
| SEQ ID NO:9 |             |             | 100%        |

Figure 10

MerD01: Cytoplasmically localized VP2 + VP5 in Tandem

MerD02: Cytoplasmically localized VP2 optimized 5'UTR + VP5 in Tandem

MerD03: Cytoplasmically localized VP2 alone

MerD04: Cytoplasmically localized VP2 with optimized 5'UTR alone

Figure 11

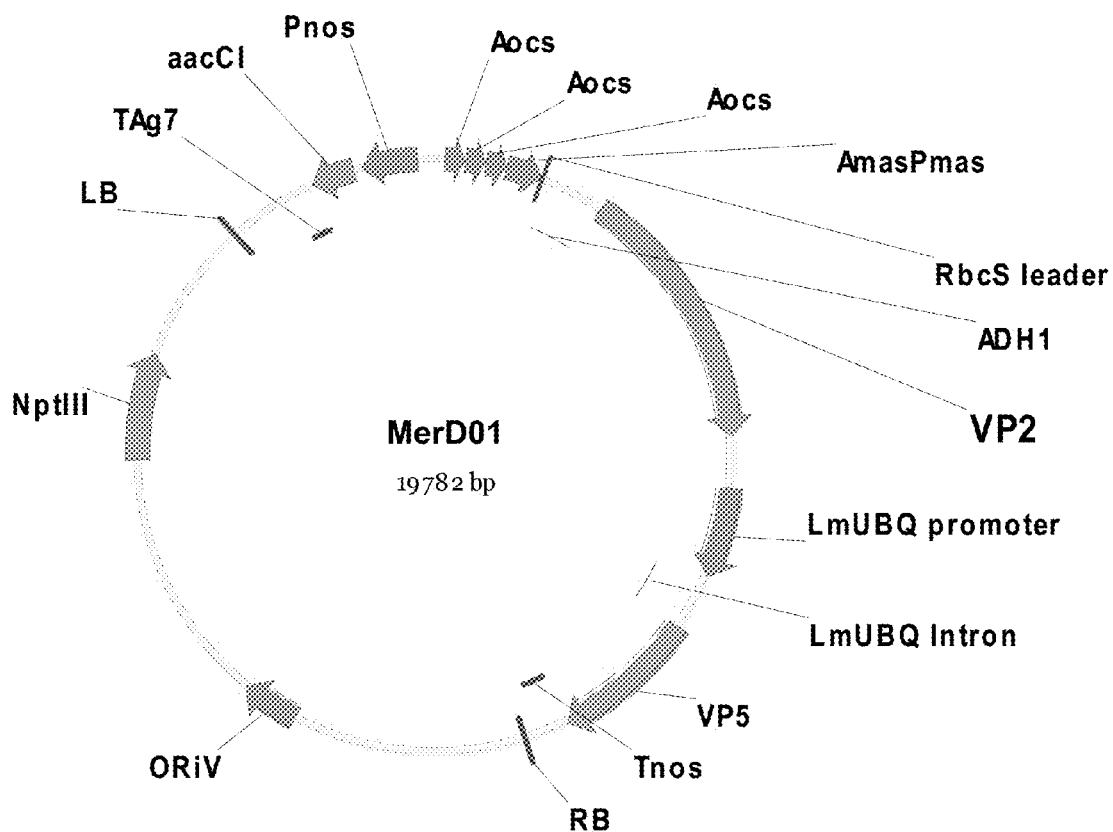

Feature Map

CDS (4): VP2: 1828-4713; VP5: 6849-8426; NptIII: 14793-15941;

aacCl (Gentamycin resistance gene): 18448-18912 (Complementary)

Intron (2): ADH1 intron: 1231-1772; LmUBQ Intron (Ubi Intron 1): 6305-6839

Promoter Eukaryotic (6): Aocs: 74-286; Aocs: 293-505; Aocs: 512-724; AmasPmas: 731-1122;

LmUBQ promoter (Lemna minor ubiquitin): 5265-6240; Pnos: 18997-19591 (Complementary)

Terminator (2): Tnos: 8448-8703; TAg7 (Gene 7 octopine synthase): 18202-18414 (Complementary)

5' UTR (1): RbcS leader (Lemna gibba RbcS (SSU5B) leader sequence): 1131-1193

Misc. Recombination (2): RB (T-DNA Right Border): 8907-9068;
        LB (T-DNA Left borderJ01825): 17467-17614 (Complementary)

Figure 12

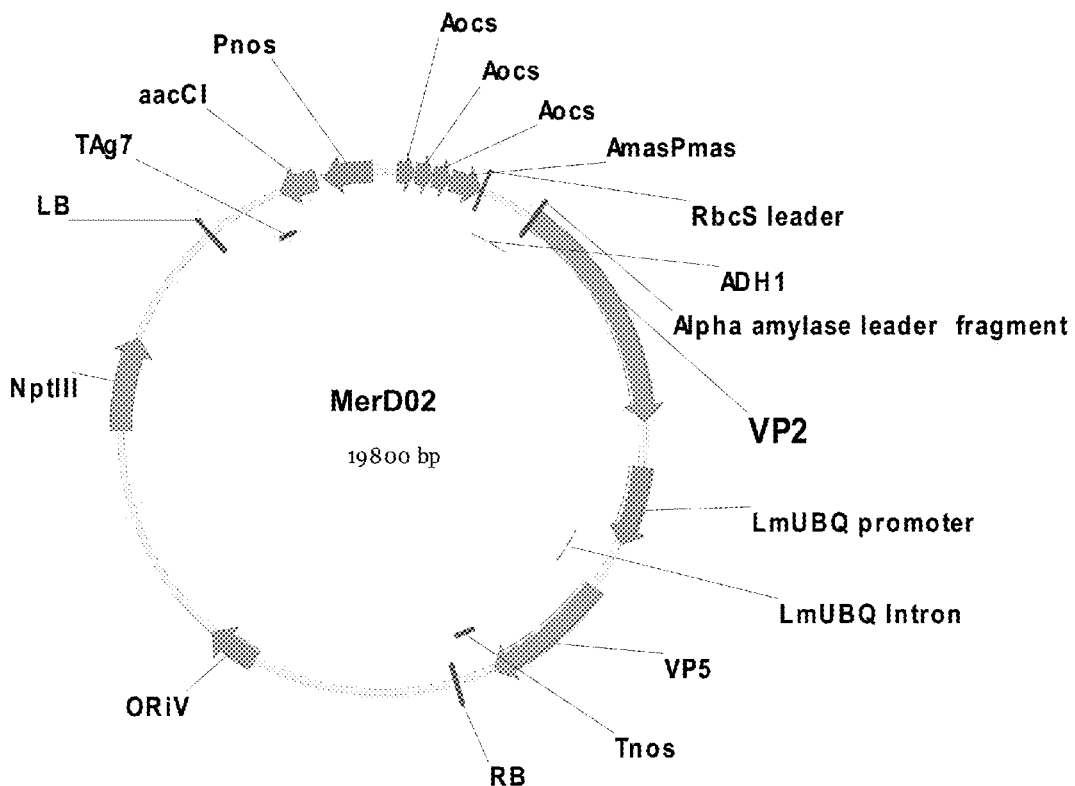

Feature Map

CDS (4): VP2: 1907-4792; VP5: 6928-8505; KmR NptIII: 14872-16020 aacCI (Gentamycin resistance gene): 18527-18991 (Complementary)

Intron (2): ADH1: 1292-1833; LmUBQ Intron (Ubi Intron 1): 6384- 6918

Promoter Eukaryotic (6): Aocs: 135-347; Aocs: 354-566; Aocs: 573-785; AmasPmas: 792-1183;

LmUBQ promoter (Lemna minor ubiquitin): 5344- 6319; Pnos: 19076-19670 (Complementary)
Terminator (2): Tnos: 8527-8782; TAg7 (Gene 7 octopine synthase): 18281 End: 18493 (Complementary)
5' UTR (2): Alpha amylase leader (fragment):1889-1909;

RbcS leader (Lemna gibba RbcS (SSU5B) leader sequence): 1192 - 1254
Misc. Recombination (2): RB (T-DNA Right Border): 8986 End: 9147;
    LB (T-DNA Left borderJ01825): 17546 End: 17693 (Complementary)

Figure 13

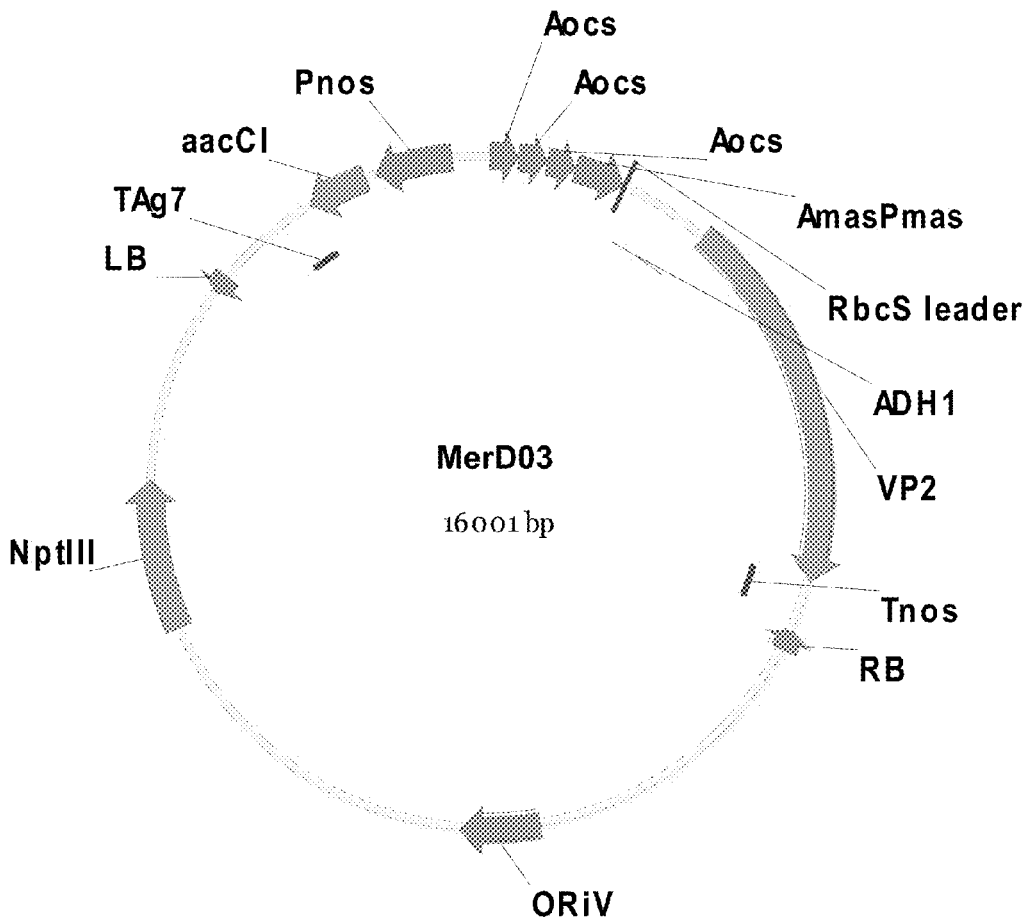

Feature Map

CDS (3): VP2: 1771-4656; KmR NptIII: 10942-12090;

aacCI (Gentamycin resistance gene): 14597-15061 (Complementary)
Intron (1): ADH1: 1161-1702;
Promoter Eukaryotic (5): Aocs: 4-216; Aocs: 223-435; Aocs: 442-654; AmasPmas: 661-1052;

Pnos: 15146-15740 (Complementary)

Terminator (2): Tnos: 4673-4928; TAg7 (Gene 7 octopine synthase): 14351-14563 (Complementary)
5' UTR (1): RbcS leader (Lemna gibba RbcS (SSU5B) leader sequence): 1061-1123
Misc. Recombination (2):

RB (T-DNA right border):5056-5217 (Complementary);

LB (T-DNA Left border.J01825):13616-13763 (Complementary)

Figure 14

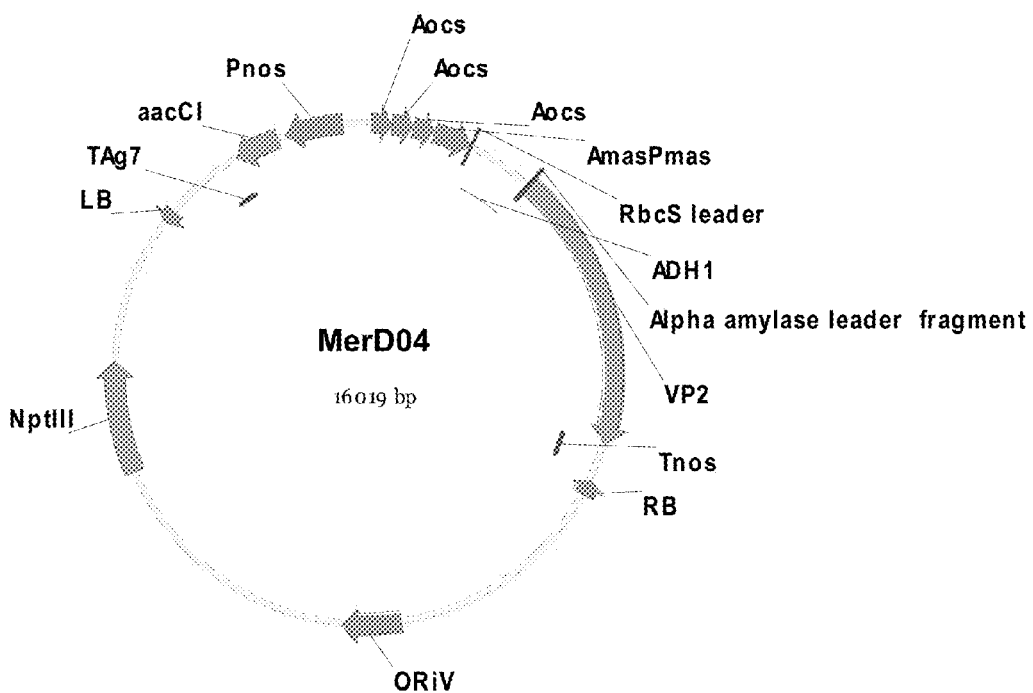

CDS (3): VP2: 1821-4706; KmR NptIII: 10992-12140 aacCI (Gentamycin resistance gene): 14647-15111 (Complementary)

Intron (1):

ADH1: 1193-1734

Promoter Eukaryotic (5): Aocs: 36-248; Aocs: 255-467; Aocs: 474-686;

AmasPmas: 693-1084; Pnos: 15196-15790 (Complementary)

Terminator (2):

Tnos: 4723-4978; TAg7 (Gene 7 octopine synthase): 14401-14613 (Complementary)

5' UTR (2): Alpha amylase leader (fragment): 1803-1823;

RbcS leader (Lemna gibba RbcS (SSU5B) leader sequence): 1093-1155

Misc. Recombination (2 total)

RB (T-DNA right border): 5106-5267 (Complementary);

LB (T-DNA Left borderJ01825): 13666-13813 (Complementary)

Figure 15
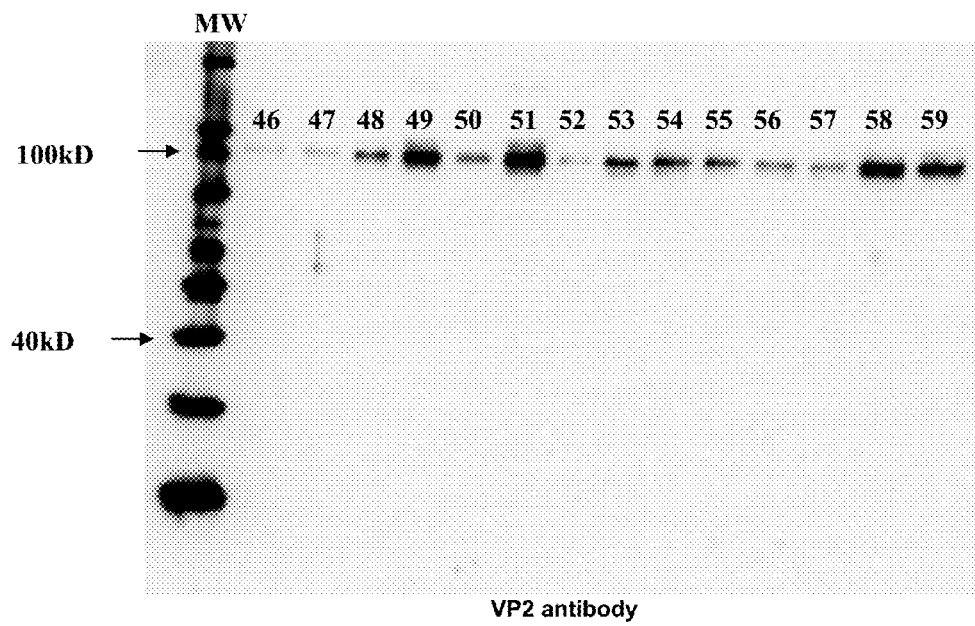
VP2 antibody
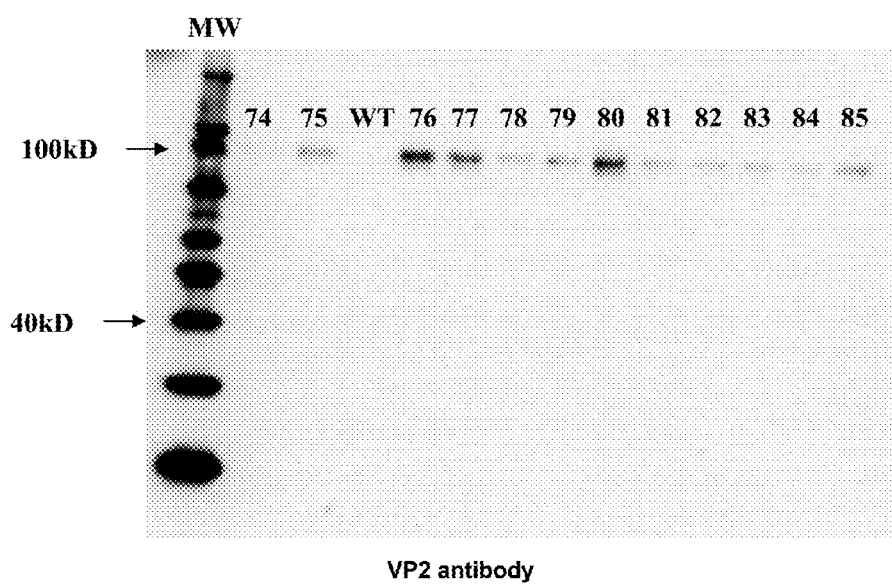
VP2 antibody

Figure 16
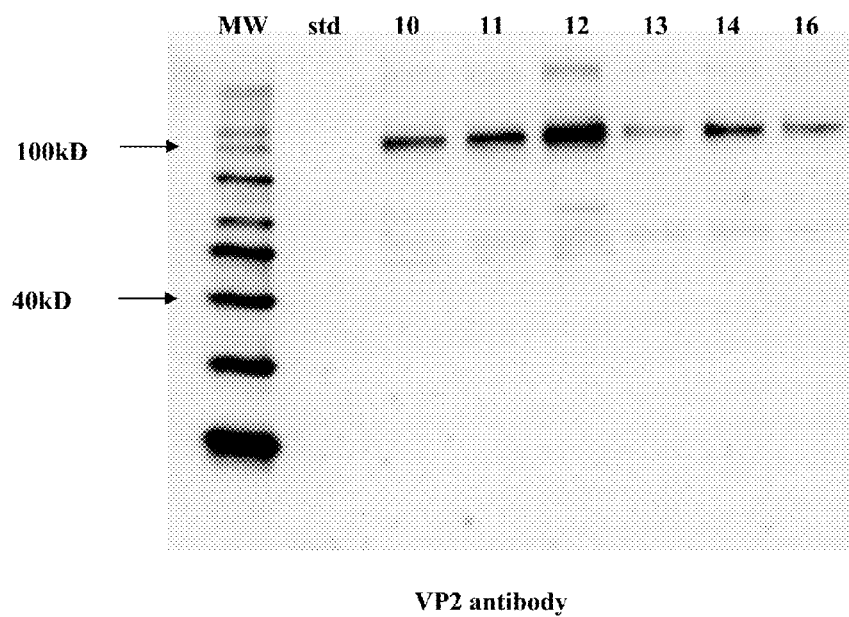
VP2 antibody
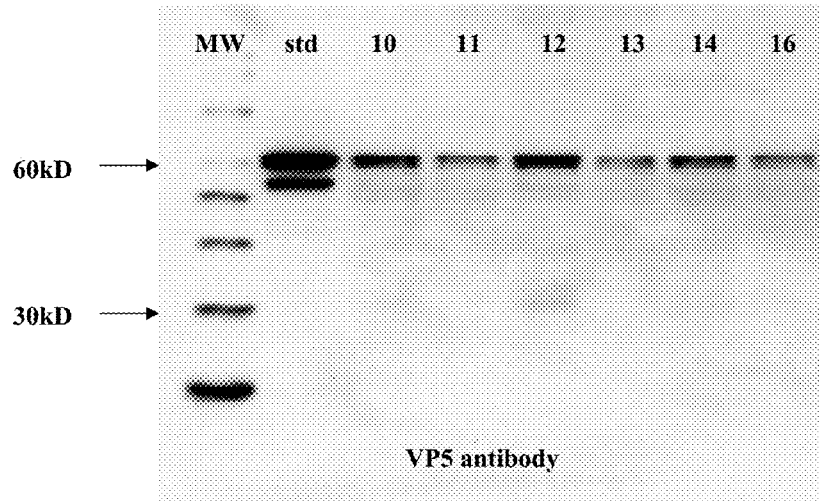
VP5 antibody
10, 11, 12, 13, 14, and 16 represent different transgenic lines transformed with Mer

Figure 17

BTV1 VP2

| Lane | Sample |
|------|--------|
| 1 | MW ladder |
| 2 | Ref |
| 3 | D01-53-0.1 µg |
| 4 | D02-3-0.1 µg (initial) |
| 5 | D02-3-0.1 µg(SV) |
| 6 | D03-80-0.1 µg (initial) |
| 7 | D03-80-0.1 µg (SV) |
| 8 | D04-11-0.1 µg |
| 9 | D01-53-0.5 µg |
| 10 | D02-3-0.5 µg (initial) |
| 11 | D02-3-0.5 µg (SV) |
| 12 | D03-80-0.5 µg (initial) |
| 13 | D03-80-0.5 µg (SV) |
| 14 | D04-11-0.5 µg |
| 15 | MW ladder |

Figure 18

BTV1 VP5

A. control

| Lane | Sample |
|---|---|
| 1 | MW |
| 2 | Time 0 |
| 3 | 4°C 2 hr |
| 4 | 4°C 4hr |
| 5 | 1x Freeze and thaw |
| 6 | 2x Freeze and thaw |
| 7 | 3x Freeze and thaw |

B. Glycerol extraction

1st Ab: mAb anti-ASHV4 VP5, Clone# 10AE12, 1:1000
2nd Ab: HRP anti-mouse IgG, 1:1000

Figure 20
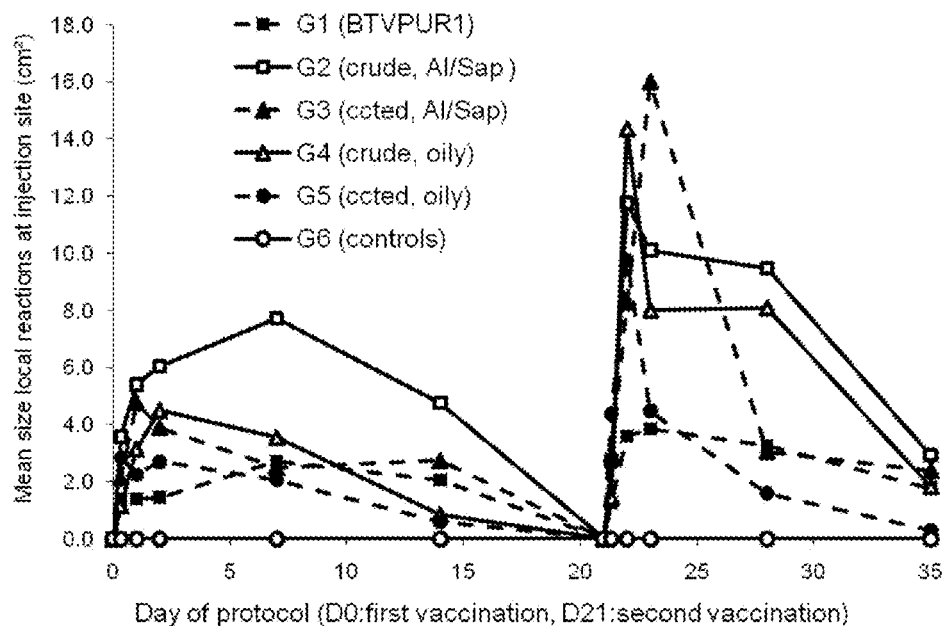
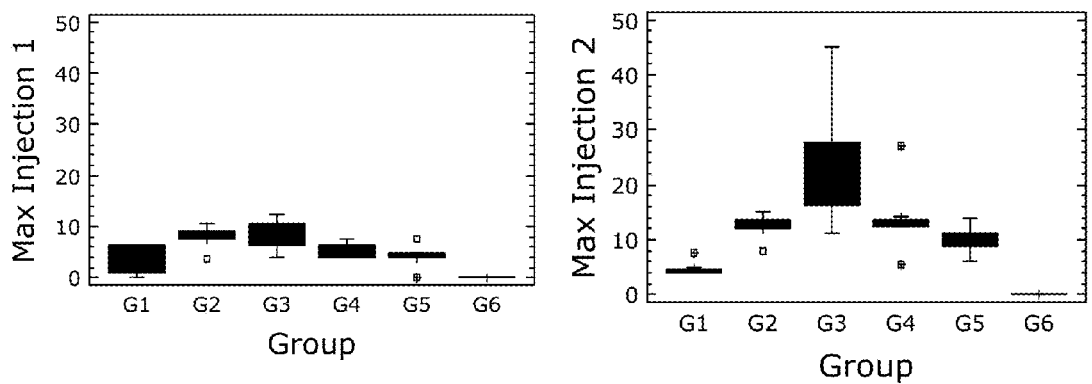

Figure 21
Rectal Temperature following First Vaccination
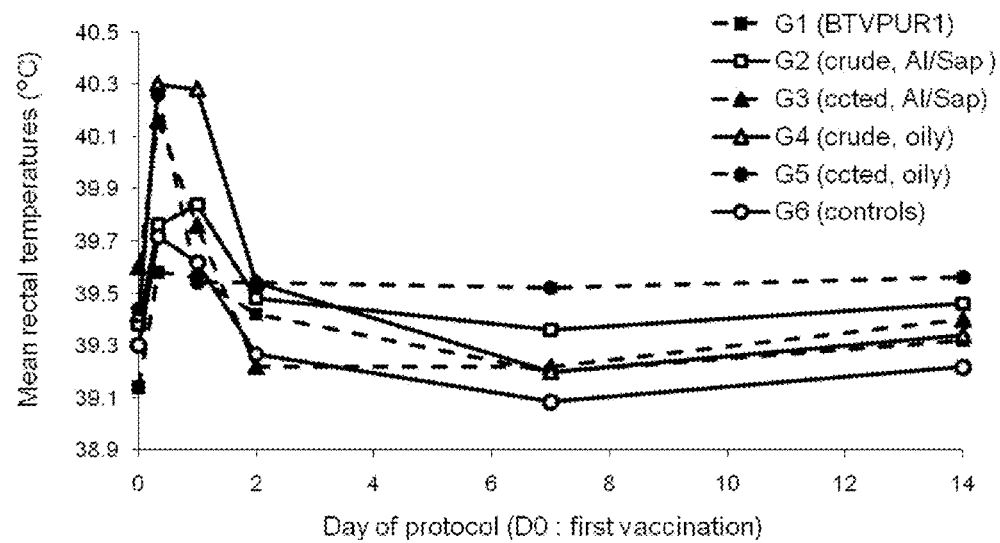
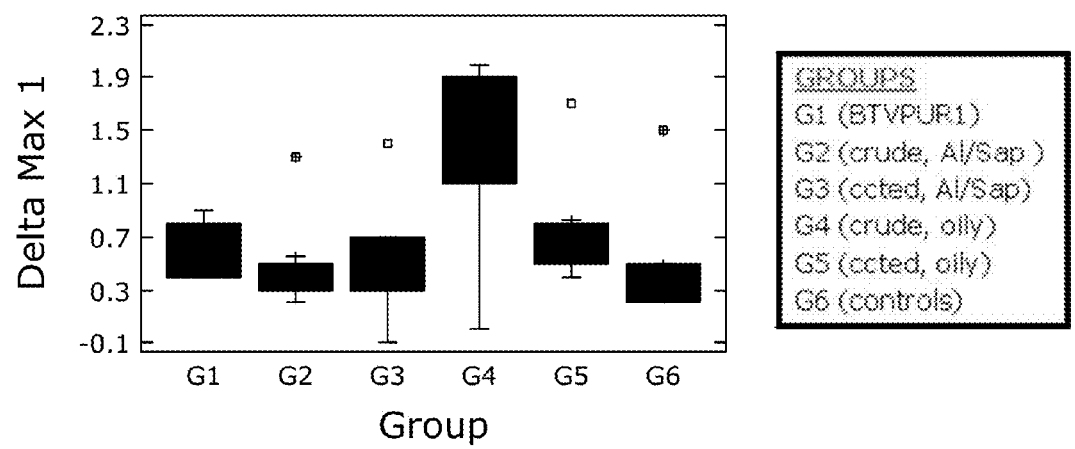

Figure 22
Rectal Temperature following Second Vaccination
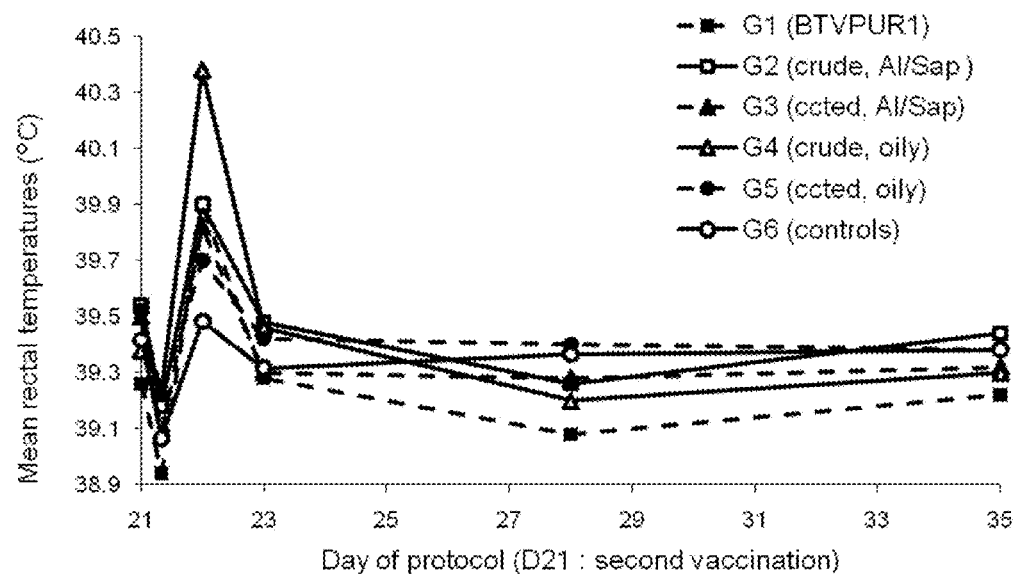
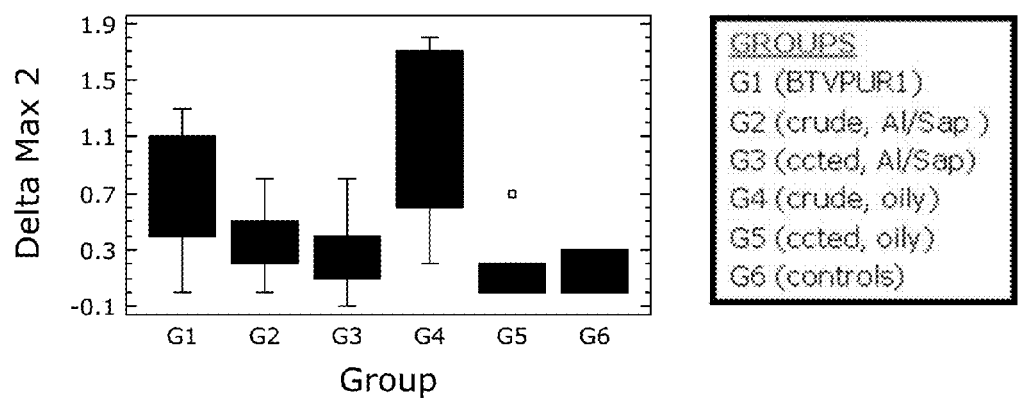

Figure 24

Clinical Signs

Legend:
- G1 (BTVPUR1)
- G2 (crude, Al/Sap)
- G3 (ccted, Al/Sap)
- G4 (crude, oily)
- G5 (ccted, oily)
- G6 (controls)

X-axis: Day of protocol (D42 : challenge)
Y-axis: Mean daily clinical score

Figure 25

BTV1 Antibody Titer by Seroneutralization

| G1 : vacc BTVPUR1 (Merial Commericial) |
| G2 : vacc 0 3122 8A011 (Duckweed Produced) |
| G3 : vacc 0 3122 8A021 (Duckweed Produced) |
| G4 : vacc 0 3122 8B031 (Duckweed Produced) |
| G5 : vacc 0 3122 8B041 (Duckweed Produced) |
| G6 : controls |

Figure 26

Mean viraemia titre measured by qRT-PCR in each treatment group

- G1 (BTVPUR1)
- G2 (031228A011;Crude Ag;Al/Sap Adjuv)
- G3 (031228A021;Conc Ag;Al/Sap Adjuv)
- G4 (031228B031;Crude Ag;Emul/CpG Adjuv)
- G5 (031228B041;Conc Ag;Emul/CpG Adjuv)
- G6 (control)

Figure 27A

```
                         1                                                  50
ACB05467(VP2)    (1)    MDELGIPVYKRGFPRHLLRGYEFQIDVGTKIESVGGRHDVTKIPEMNAYD
ACJ65032(VP2)    (1)    MDELGIPVYKRGFPRHLLRGYEFQIDVGTKIESVGGRHDVTKIPEMNAYD
SEQ ID NO:4      (1)    MDELGIPVYKRGFPRHLLRGYEFQIDVGTKIESVGGRHDVTKIPEMNAYD
ACF37215(VP2)    (1)    MDELGIPVYKRGFPRHLLRGYEFQIDVGTKIESVGGRHDVTKIPEMNAYD
ACF37216(VP2)    (1)    MDELGIPVYKRGFPVHLLRGYEFQIDVGTKIESVGGRHDVTKIPEMNAYD
ACR58459(VP2)    (1)    MDELGIPVYKRGFPRHLLRGYEFQIDVGTKIESVGGRHDVTKIPEMNAYD
CAA39322(VP2)    (1)    MDELGIPVYKRGFPRHLLRGYEFTIDVGTKIESVGGRHDVTKIPEMNAYD
CAE51088(VP2)    (1)    MDELGIPVYKRGFPRHLLRGYEFQIDVGTKIESVGGRHDVTKIPEMNAYD 51                                                100
ACB05467(VP2)    (51)   IKQESIRTALWYNPIRNDGPVLPRVLDITLRGYDERRAVVESTRHKSFHT
ACJ65032(VP2)    (51)   IKQESIRTALWYNPIRNDGPVLPRVLDITLRGYDERRAVVESTRHKSFHT
SEQ ID NO:4      (51)   IKQESIRTALWYNPIRNDGPVLPRVLDITLRGYDERRAVVESTRHKSFHT
ACF37215(VP2)    (51)   IKQESIRTALWYNPIRNDGPVLPRVLDITLRGYDERRAVVESTRHKSFHT
ACF37216(VP2)    (51)   IKQESIRTALWYNPIRNDGPVLPRVLDITLRGYDERRAVVESTRHKSFHT
ACR58459(VP2)    (51)   IKQESIRTALWYNPIRNDGPVLPRVLDITLRGYDERRAVVESTRHKSFHT
CAA39322(VP2)    (51)   IKQESIRTALWYNPIRNDGIVLPRVLDITLRGYDERRAVVESTRHKSFHT
CAE51088(VP2)    (51)   IKQESIRTALWYNPIRNDGIVLPRVLDITLRGYDERRAVVESTRHKSFHT 101                                               150
ACB05467(VP2)    (101)  NDQWVQWMMKDSMDAQPLKVGLDDQSRNVAHSLHNCVVKIDSKKADTMSY
ACJ65032(VP2)    (101)  NDQWVQWMMKDSMDAQPLKVGLDDQSRNVAHSLHNCVVKIDSKKADTMSY
SEQ ID NO:4      (101)  NDQWVQWMMKDSMDAQPLKVGLDDQSRNVAHSLHNCVVKIDSKKADTMSY
ACF37215(VP2)    (101)  NDQWVQWMMKDSMDAQPLKVGLDDQSRNVAHSLHNCVVKIDSKKADTMSY
ACF37216(VP2)    (101)  NDQWVQWMMKDSMDAQPLKVGLDDQSRNVAHSLHNCVVKIDSKKADTMSY
ACR58459(VP2)    (101)  NDQWVQWMMKDSMDAQPLKVGLDDQSRNVAHSLHNCVVKIDSKKADTMSY
CAA39322(VP2)    (101)  NDQWVQWMMKDSMDAQPLKVGLDDQSRNVAHSLHNCVVKIDSKKADTMSY
CAE51088(VP2)    (101)  NDQWVQWMMKDSMDAQPLKVGLDDQSRNVAHSLHNCVVKIDSKKADTMSY 151                                               200
ACB05467(VP2)    (151)  HVEPIEDASKGCLHTRTMMMNHLVRIETFHAQEVAYTLKPTYDIVVHAK
ACJ65032(VP2)    (151)  HVEPIEDASKGCLHTRTMMMNHLVRIETFHAQEVAYTLKPTYDIVVHAK
SEQ ID NO:4      (151)  HVEPIEDASKGCLHTRTMMMNHLVRIETFHAQEVAYTLKPTYDIVVHAK
ACF37215(VP2)    (151)  HVEPIEDASKGCLHTRTMMMNHLVRIETFHAQEVAYTLKPTYDIVVHAK
ACF37216(VP2)    (151)  HVEPIEDASKGCLHTRTMMMNHLVRIETFHAQEVAYTLKPTYDIVVHAK
ACR58459(VP2)    (151)  HVEPIEDASKGCLHTRTMMMNHLVRIETFHAQEVAYTLKPTYDIVVHAK
CAA39322(VP2)    (151)  HVEPIEDASKGCLHTRTMMMNHLVRIETFHTAQEVHILFKPTYDIVVHAK
CAE51088(VP2)    (151)  HVEPIEDASKGCLHTRTMMMNHLVRIETFHAQEVAYTLKPTYDIVVHAK 201                                               250
ACB05467(VP2)    (201)  RRDRSQPFRPGDQTLINFGRGQKVTMNHNSYDKMVEGLAHLVIRGKIPEV
ACJ65032(VP2)    (201)  RRDRSQPFRPGDQTLINFGRGQKVTMNHNSYDKMVEGLAHLVIRGKIPEV
SEQ ID NO:4      (201)  RRDRSQPFRPGDQTLINFGRGQKVTMNHNSYDKMVEGLAHLVIRGKIPEV
ACF37215(VP2)    (201)  RRDRSQPFRPGDQTLINFGRGQKVTMNHNSYDKMVEGLAHLVIRGKIPEV
ACF37216(VP2)    (201)  RRDRSQPFRPGDQTLINFGRGQKVTMNHNSYDKMVEGLAHLVIRGKIPEV
ACR58459(VP2)    (201)  RRDRSQPFRPGDQTLINFGRGQKVAMNHNSYDKMVEGLTHLVIRGKTPEV
CAA39322(VP2)    (201)  RRDRSQPFRPGDQTLINFGRGQKVHMNHNSYDKMVEGLTHLVMRGKMPEV
CAE51088(VP2)    (201)  RRDRSQPFRPGDQTLINFGRGQKVAMNHNSYDKMVEGLTHLVIRGKTPEV
```

Figure 27B

```
                    251                                                   300
ACB05467(VP2)  (251) IRDDIASLDEICNRWIQSRHDPGEIKAYELCKILSTIGRKVLDREKEPED
ACJ65032(VP2)  (251) IRDDIASLDEICNRWIQSRHDPGEIKAYELCKILSTIGRKVLDREKEPED
SEQ ID NO:4    (251) IRDDIASLDEICNRWIQSRHDPGEIKAYELCKILSTIGRKVLDREKEPED
ACF37215(VP2)  (251) IRDDIASLDEICNRWIQSRHDPGEIKAYELCKILSTIGRKVLDREKEPED
ACF37216(VP2)  (251) IRDDIASLDEICNRWIQSRHDPGEIKAYELCKILSTIGRKVLDREKEPED
ACR58459(VP2)  (251) IRDDIASLDEICNRWIQSRHDPGEIKAYELCKILSTIGRKVLDREKEPED
CAA39322(VP2)  (251) IRDDIASLDEICNRWIQSRHDPGEVKAYELCKILSTIGRKVLDREKEPED
CAE51088(VP2)  (251) IRDDIASLDEICNRWIQSRHDPGEIKAYELCKILSTIGRKVLDREKEPED 301                                                   350
ACB05467(VP2)  (301) EASLSIRFQEAIDNKFRQHDPERLKIFEHRNQRRDEDRFYILLMIAASDT
ACJ65032(VP2)  (301) EASLSIRFQEAIDNKFRQHDPERLKIFEHRNQRRDEDRFYILLMIAASDT
SEQ ID NO:4    (301) EASLSIRFQEAIDNKFRQHDPERLKIFEHRNQRRDEDRFYILLMIAASDT
ACF37215(VP2)  (301) EASLSIRFQEAIDNKFRQHDPERLKIFEHRNQRRDEDRFYILLMIAASDT
ACF37216(VP2)  (301) EASLSIRFQEAIDNKFRQHDPERLKIFEHRNQRRDEDRFYILLMIAASDT
ACR58459(VP2)  (301) EANLSIRFQEAIDNKFRQHDPERLKIFEHRNQRRDEDRFYILLMIAASDT
CAA39322(VP2)  (301) EANLSIRFQEAIDNKFRQHDPERLKIFEHGNQRRDEDRFYILLMIAASDT
CAE51088(VP2)  (301) EANLSIRFQEAIDNKFRQHDPERLKIFEHRNQRRDEDRFYILLMIAASDT 351                                                   400
ACB05467(VP2)  (351) FNTRVWWSNPYPCLRGTLIASETKLGDVYSMMRSWYDWSVRPTYTPYEKT
ACJ65032(VP2)  (351) FNTRVWWSNPYPCLRGTLIASETKLGDVYSMMRSWYDWSVRPTYTPYEKT
SEQ ID NO:4    (351) FNTRVWWSNPYPCLRGTLIASETKLGDVYSMMRSWYDWSVRPTYTPYEKT
ACF37215(VP2)  (351) FNTRVWWSNPYPCLRGTLIASETKLGDVYSMMRSWYDWSVRPTYTPYEKT
ACF37216(VP2)  (351) FNTRVWWSNPYPCLRGTLIASETKLGDVYSMMRSWYDWSVRPTYTPYEKT
ACR58459(VP2)  (351) FNTRVWWSNPYPCLRGTLIASETKLGDVYSMMRSWYDWSVRPTYTPYEKT
CAA39322(VP2)  (351) FNTRVWWSNPYPCLRGTLIASETKLGDVYSMMRSWYDWSVRPTYTPYEKT
CAE51088(VP2)  (351) FNTRVWWSNPYPCLRGTLIASETKLGDVYSMMRSWYDWSVRPTYTPYEKT 401                                                   450
ACB05467(VP2)  (401) REQEKYIYGRVNLFDFVAEPGIKIVHWEYRLNHSTREITYAQGNPCDLYP
ACJ65032(VP2)  (401) REQEKYIYGRVNLFDFVAEPGIKIVHWEYRLNHSTREITYAQGNPCDLYP
SEQ ID NO:4    (401) REQEKYIYGRVNLFDFVAEPGIKIVHWEYRLNHSTREITYAQGNPCDLYP
ACF37215(VP2)  (401) REQEKYIYGRVNLFDFVAEPGIKIVHWEYRLNHSTREITYAQGNPCDLYP
ACF37216(VP2)  (401) REQEKYIYGRVNLFDFVAEPGIKIVHWEYRLNHSTREITYAQGNPCDLYP
ACR58459(VP2)  (401) REQEKYIYGRVNLFDFVAEPGIKIVHWEYRLNHSTREITYAQGNPCDLYP
CAA39322(VP2)  (401) REQEEYIYGRVNLFDFVAEPGIKIVHWEYRLNHSTREITYAQGNPCDLYP
CAE51088(VP2)  (401) REQEKYIYGRVNLFDFVAEPGIKIVHWEYRLNHSTREITYAQGNPCDLYP 451                                                   500
ACB05467(VP2)  (451) EDDDVIVTKFDDVAYGQMINEMINGGWNQEQFKMHKILKSEGNVLTIDFE
ACJ65032(VP2)  (451) EDDDVIVTKFDDVAYGQMINEMINGGWNQEQFKMHKILKSEGNVLTIDFE
SEQ ID NO:4    (451) EDDDVIVTKFDDVAYGQMINEMINGGWNQEQFKMHKILKSEGNVLTIDFE
ACF37215(VP2)  (451) EDDDVIVTKFDDAAYGQMINEMINGGWNQEQFKMHKILKSEGNVLTIDFE
ACF37216(VP2)  (451) EDDDVIVTKFDDAAYGQMINEMINGGWNQEQFKMHKILKSEGNVLTIDFE
ACR58459(VP2)  (451) EDDDVIVTKFDDVAYGQMINEMINGGWNQEQFKMHKILKSEGNVLTIDFE
CAA39322(VP2)  (451) EDDDVIVTKFDDVAYGQMINEMINGGWNQEQFKMHKILKTEGNVLTIDFE
CAE51088(VP2)  (451) EDDDVIVTKFDDVAYGQMINEMINGGWNQEQFKMHKILKSEGNVLTIDFE
```

Figure 27C

```
                     501                                                    550
ACB05467(VP2)  (501) KDAKLTTNEGVTMPEYFNRWIIAPMFNAKLRIKHEEIAQRQSDDPMVKRT
ACJ65032(VP2)  (501) KDAKLTTNEGVTMPEYFNRWIIAPMFNAKLRIKHEEIAQRQSDDPMVKRT
SEQ ID NO:4    (501) KDAKLTTNEGVTMPEYFNRWIIAPMFNAKLRIKHEEIAQRQSDDPMVKRT
ACF37215(VP2)  (501) KDAKLTTNEGVTMPEYFNRWIIAPMFNAKLRIKHEEIAQRQSDDPMVKRT
ACF37216(VP2)  (501) KDAKLTTNEGVTMPEYFNKWIIAPMFNAKLRIKHEEIAQRQSDDPMVKRT
ACR58459(VP2)  (501) KDAKLTTNEGVTMPEYFNRWIIAPMFNAKLRIKHEEIAQRQSDDPMVKRT
CAA39322(VP2)  (501) KDAKLTTNEGVTMPEYFNRWIIAPMFNAMVRIKHEEIAQRQSDDPMVKRT
CAE51088(VP2)  (501) KDAKLTTNEGVTMPEYFNRWIIAPMFNAKLRIKHEEIAQRQSDDPMVKRT 551                                                    600
ACB05467(VP2)  (551) LSPITADPIELQRLTLARFYDIRPALRGQALSRQQAQSTYDEEISKRQDY
ACJ65032(VP2)  (551) LSPITADPIELQRLTLARFYDIRPALRGQALSRQQAQSTYDEEISKRQDY
SEQ ID NO:4    (551) LSPITADPIELQRLTLARFYDIRPALRGQALSRQQAQSTYDEEISKRQDY
ACF37215(VP2)  (551) LSPITADPIELQRLTLARFYDIRPALRGQALSRQQAQSTYDEEISKRQDY
ACF37216(VP2)  (551) LSPITADPIELQRLTLARFYDIRPALRGQALSRQQAQSTYDEEISKRQDY
ACR58459(VP2)  (551) LSPITADPIELQRLTLARFYDIRPALRGQALSRQQAQSTYDEEISKQRDY
CAA39322(VP2)  (551) LSPITADPIELQRLTLARFYDIRPALRGQALSRQQAQSTYDEEISKKAGY
CAE51088(VP2)  (551) LSPITADPIELQRLTLARFYDIRPALRGQALSRQQAQSTYDEEISRKAGY 601                                                    650
ACB05467(VP2)  (601) AEILKRRGIVQIPKRPCPTVTAQYTLERYALFIINILQQHVVRDCDEEAV
ACJ65032(VP2)  (601) AEILKRRGIVQIPKRPCPTVTAQYTLERYALFIISILQQHVVRDCDEEAV
SEQ ID NO:4    (601) AEILKRRGIVQIPKRPCPTVTAQYTLERYALFIISILQQHVVRDCDEEAV
ACF37215(VP2)  (601) AEILKRRGIVQIPKRPCPTVTAQYTLERYALFIINILQQHVVRDCDEEAV
ACF37216(VP2)  (601) AEILKRRGIVQIPKRPCPTVTAQYTLERYALFIINILQQHVVRDCDEEAV
ACR58459(VP2)  (601) AEILKRRGIVQIPKRPCPTVTAQYTLERYALFIINILQQHVARDCDEEAI
CAA39322(VP2)  (601) AEVLKRRGIVQIPKRPCPTVTAQYTLERYALFIINYLQQHVARDCDEEAI
CAE51088(VP2)  (601) AEILKRRGIVQIPKRPCPTVTAQYTLERYALFIINYLQQHVARDCDEEAI 651                                                    700
ACB05467(VP2)  (651) YEHPKADHELEIFGESIVDISQVITLAFDLIFERRRVRDVYESRHIIAR
ACJ65032(VP2)  (651) YEHPKADHELEIFGESIVDISQVITLAFDLIFERRRVRDVYESRHIIAR
SEQ ID NO:4    (651) YEHPKADHELEIFGESIVDISQVITLAFDLIFERRRVRDVYESRHIIAR
ACF37215(VP2)  (651) YEHPKADHELEIFGESIVDISQVITLAFDLIFERRRVRDVYESRHIIAR
ACF37216(VP2)  (651) YEHPKADHELEIFGESIVDISQVITLAFDLIFERRRVRDVYESRHIIAR
ACR58459(VP2)  (651) YEHPKADYELEIFGESIVDISQVIVLVFDLIFERRRVRDVYESRYIIAR
CAA39322(VP2)  (651) YEHPKADHELEIFGESIVDISQVIVLVFDLIFERRRVRDVYESRYIIAR
CAE51088(VP2)  (651) YEHPKADYELEIFGESIVDISQVIVLVFDLIFERRRVRDVYESRYIIAR 701                                                    750
ACB05467(VP2)  (701) IRRMRGKERLNVIAEFFPTYGGLLNGLNSATVVQDIMYLNFLPLYFLVGD
ACJ65032(VP2)  (701) IRRMRGKERLNVIAEFFPTYGGLLNGLNSATVVQNIMYLNFLPLYFLVGD
SEQ ID NO:4    (701) IRRMRGKERLNVIAEFFPTYGGLLNGLNSATVVQNIMYLNFLPLYFLVGD
ACF37215(VP2)  (701) IRRMRGKERLNVIAEFFPTYGGLLNGLNSATVVQDIMYLNFLPLYFLVGD
ACF37216(VP2)  (701) IRRMRGKERLNVIAEFFPTYGGLLNGLNSATVVQDIMYLNFLPLYFLVGD
ACR58459(VP2)  (701) IRRMRGKERLNVIAEFFPTYGSLLNGLNSATVVQDIMYLNFLPLYFLAGD
CAA39322(VP2)  (701) IREMRGKERLNVIAEFFPTYGSLLNGLSGATVVQDIMYLNFLPLYFLVGD
CAE51088(VP2)  (701) IRRMRGKERLNVIAEFFPTYGSLLNGLNSATVVQDIMYLNFLPLYFLAGD 751                                                    800
ACB05467(VP2)  (751) NMIYSHRQWSIPLLLYTHEVMVVPLEVGSYNDRCGLIAYLEYMVFPSKA
ACJ65032(VP2)  (751) NMIYSHRQWSIPLLLYTHEVMVVPLEVGSYNDRCGLIAYLEYMVFPSKA
SEQ ID NO:4    (751) NMIYSHRQWSIPLLLYTHEVMVVPLEVGSYNDRCGLIAYLEYMVFPSKA
ACF37215(VP2)  (751) NMIYSHRQWSIPLLLYTHEVMVVPLEVGSYNDRCGLIAYLEYMVFPSKA
```

Figure 27D

```
ACF37216(VP2)  (751)  NMIYSHRQWSIPLLLYTHEVMVVPLEVGSYNDRCGLIAYLEYMVFFPSKA
ACR58459(VP2)  (751)  NMIYSHRQWSIPLLLYTHEVMVVPLEVGSYNDRCGLIAYLEYMVFFPSKA
CAA39322(VP2)  (751)  NMIYSHRQWSIPLLLYTHEVMVIPLEVGSYNDRCGLIAYLEYMVFFPSKA
CAE51088(VP2)  (751)  NMIYSHRQWSIPLLLYTHEVMVIPLEVGSYNDRCGLIAYLEYMVFFPSKA 801                                            850
ACB05467(VP2)  (801)  IRESKLNEAQPKIAREMLKYYANTIVYDGGVNYNVVTTKQLLYETYLASL
ACJ65032(VP2)  (801)  IRESKLNEAQPKIAREMLKYYANTIVYDGGVNYNVVTTKQLLYETYLASL
SEQ ID NO:4    (801)  IRESKLNEAQPKIAREMLKYYANTIVYDGGVNYNVVTTKQLLYETYLASL
ACF37215(VP2)  (801)  IRESKLNEAQPKIAREMLKYYANTIVYDGGVNYNVVTTKQLLYETYLASL
ACF37216(VP2)  (801)  IRSSKLNEAQPKIAREMLKYYANTIVYDGGVNYNVVTTKQLLYETYLASL
ACR58459(VP2)  (801)  IRLSKLNEAQPKIAREMLKYYANTAVYDGGVNYNVVTTKQLLYETYLASL
CAA39322(VP2)  (801)  IRLSKLNEAHAKIAREMLKYYANTIVYDGGDNSNVVTTKQLLYETYLASL
CAE51088(VP2)  (801)  IRLSKLNEAHAKIAREMLKYYANTIVYDGGDNYNVVTTKQLLYETYLASL 851                                            900
ACB05467(VP2)  (851)  CGGISDGIVWYLPITHPNKCIVAIEVSDERVPASIRAGRIRLRFPLSARH
ACJ65032(VP2)  (851)  CGGISDGIVWYLPITHPNKCIVAIEVSDERVPASIRAGRIRLRFPLSARH
SEQ ID NO:4    (851)  CGGISDGIVWYLPITHPNKCIVAIEVSDERVPASIRAGRIRLRFPLSARH
ACF37215(VP2)  (851)  CGGISDGIVWYLPITHPNKCIVAIEVSDERVPASIRAGRIRLRFPLSARH
ACF37216(VP2)  (851)  CGGISDGIVWYLPITHPNKCIVAIEVSDERVPASIRAGRIRLRFPLSARH
ACR58459(VP2)  (851)  CGGISDGIVWYLPITHPNKCIVAIEVSDERVPASIRAGRIRLRFPLSARH
CAA39322(VP2)  (851)  CGGFLDGIVWYLPITHPNKCIVAIEVSDERVPASVRAGRIRLRFPLSARH
CAE51088(VP2)  (851)  CGGISDGIVWYLPITHPNKCIVAIEVSDERVPASIRAGRIRLRFPLSARH 901                                            950
ACB05467(VP2)  (901)  LKGVVIIQIDEEGRFTVYSEGIVSHRVCKKNLLKYMCDIILLKFSGHVFG
ACJ65032(VP2)  (901)  LKGVVIIQIDEEGRFTVYSEGIVSHRVCKKNLLKYMCDIILLKFSGHVFG
SEQ ID NO:4    (901)  LKGVVIIQIDEEGRFTVYSEGIVSHRVCKKNLLKYMCDIILLKFSGHVFG
ACF37215(VP2)  (901)  LKGVVIIQIDEEGRFTVYSEGIVSHRVCKKNLLKYMCDIILLKFSGHVFG
ACF37216(VP2)  (901)  LKGVVIIQIDEEGRFTVYSEGIVSHRVCKKNLLKYMCDIILLKFSGHVFG
ACR58459(VP2)  (901)  LKGVVIIQIDEEGRFTVYSEGIVSHRVCKKNLLKYMCDIILLKFSGHVFG
CAA39322(VP2)  (901)  LKGVVIIQVDLGGRFTVYSEGIVSHRVCKKNLLKYMCDIILLKFSGHVFG
CAE51088(VP2)  (901)  LKGVVIIQIDRGGRFTVYSEGIVSHRVCKKNLLKYMCDIILLKFSGHVFG 951      962
ACB05467(VP2)  (951)  NDEMLTKLLNV-
ACJ65032(VP2)  (951)  NDEMLTKLLNV-
SEQ ID NO:4    (951)  NDEMLTKLLNV-
ACF37215(VP2)  (951)  NDEMLTKLLNV-
ACF37216(VP2)  (951)  NDEMLTKLLNV-
ACR58459(VP2)  (951)  NDEMLTKLLNV-
CAA39322(VP2)  (951)  NDEMLTKLLNV-
CAE51088(VP2)  (951)  NDEMLTKLLNV-
```

Sequence identity percentage (performed using VNTI software)
SEQ ID NO:4 v. ACB05467 (SEQ ID NO:11) = 99.8%
SEQ ID NO:4 v. ACF37215 (SEQ ID NO:12) = 99.7%
SEQ ID NO:4 v. ACF37216 (SEQ ID NO:13) = 99.5%
SEQ ID NO:4 v. ACJ65032 (SEQ ID NO:14) = 100%
SEQ ID NO:4 v. ACR58459 (SEQ ID NO:15) = 98.1%
SEQ ID NO:4 v. CAA39322 (SEQ ID NO:16) = 95.0%
SEQ ID NO:4 v. CAE51088 (SEQ ID NO:17) = 97.1%

Figure 28A

```
                       1                                                  50
ACB59233(VP5)    (1)   MGKVIRSLSRFGKKVGNALTSNTARKIYSTIGKAAERFAESEIGSAAIDG
ACB59234(VP5)    (1)   MGKVIRSLSRFGKKVGNALTSNTARKIYSTIGKAAERFAESEIGSAAIDG
SEQ ID NO:10     (1)   MGKVIRSLSRFGKKVGNALTSNTARKIYSTIGKAAERFAESEIGSAAIDG
ACR58462(VP5)    (1)   MGKVIRSLNRFGKKVGNALTSNTARKIYSTIGKAAERFAESEIGSAAIDG
CAE53011(VP5)    (1)   MGKVIRSLSRFGKKVGNALTSNTARKIYSTIGKAAERFAESEIGSAAIDG
CAE52973(VP5)    (1)   MGKVIRSLSRFGKKVGNALTSNTARKIYSTIGKAAERFAESEIGSAAIDG
CAE52974(VP5)    (1)   MGKVIRSLSRFGKKVGNALTSNTARKIYSTIGKAAERFAESEIGSAAIDG
CAE52979(VP5)    (1)   MGKVIRSLSRFGKKVGNALTSNTARKIYSTIGKAAERFAESEIGSAAIDG
CAE52991(VP5)    (1)   MGKVIRSLSRFGKKVGSALTSNTARKIYSTIGKAAERFAESEIGSAAIDG 51                                                100
ACB59233(VP5)    (51)  LVQGSVRSIITGESYGESVRQAVLLNVLGSGEEIPDPLSPGERGIQAKLK
ACB59234(VP5)    (51)  LVQGSVRSIITGESYGESVRQAVLLNVLGSGEEIPDPLSPGERGIQAKLK
SEQ ID NO:10     (51)  LVQGSVRSIITGESYGESVRQAVLLNVLGSGEEIPDPLSPGERGIQAKLK
ACR58462(VP5)    (51)  LVQGSVRSIITGESYGESVRQAVLLNVLGSGEEIPDPLSPGERGIQAKLK
CAE53011(VP5)    (51)  LVQGSVRSIITGESYGESVRQAVLLNVLGSGEEIPDPLSPGERGIQAKLK
CAE52973(VP5)    (51)  LVQGSVRSIITGESYGESVRQAVLLNVLGSGEEIPDPLSPGERGIQAKLK
CAE52974(VP5)    (51)  LVQGSVRSIITGESYGESVRQAVLLNMLGNGEEIPDPLSPGERGIQAKLK
CAE52979(VP5)    (51)  LVQGSVRSIITGESYGESVRQAVLLNVLGSGEEIPDPLSPGERGIQAKLK
CAE52991(VP5)    (51)  LVQGSVRSIITGESYGQSVRQAVLLNVLGNGEEIPDPLSPGERGMQVKLK 101                                               150
ACB59233(VP5)    (101) RLEDEQRNELVRLKYNDKIKEKFGKELEEVYNFMNGEANAEIEDEKQFDI
ACB59234(VP5)    (101) RLEDEQRNELVRLKYNDKIKEKFGKELEEVYNFMNGEANAEIEDEKQFDI
SEQ ID NO:10     (101) RLEDEQRNELVRLKYNDKIKEKFGKELEEVYNFMNGEANAEIEDEKQFDI
ACR58462(VP5)    (101) RLEDEQRNELVRLKYNDKIKEKFGKELEEVYNFMNGEANAEIEDEKQFDI
CAE53011(VP5)    (101) RLEDEQRNELVRLKYNDKIKEKFGKELEEVYNFMNGEANAEIEDEKQFDI
CAE52973(VP5)    (101) RLEDEQRNELVRLKYNDKIKEKFGKELEEVYNFMNGEANAEIEDEKQFDI
CAE52974(VP5)    (101) RLEDEQRNELVRLKYNDKIKEKFGKELEEVYNFMNGEANAEIEDEKQFDI
CAE52979(VP5)    (101) RLEDEQRNELVRLKYNDKIKEKFGEELEEVYEFMNGAAKAEVEDEKQFDI
CAE52991(VP5)    (101) RLEDEQRNELVRLKYNDKIKEKFGKELEEIYEFMNGEAKVEAEDEKQFDI 151                                               200
ACB59233(VP5)    (151) LNKAVTSYNKILTEEDLQMRRLATALQKEIGERTHAETVMVKEYRDKIDA
ACB59234(VP5)    (151) LNRAGTSYNKILTEEDLQMRRLATALQKEIGERTHAETVMVKEYRDKIDA
SEQ ID NO:10     (151) LNKAVTSYNKILTEEDLQMRRLATALQKEIGERTHAETVMVKEYRDKIDA
ACR58462(VP5)    (151) LNKAVTSYNKILTEEDLQMRRLATALQKEIGERTHAETVMVKEYRDKIDA
CAE53011(VP5)    (151) LNKAVTSYNKILTEEDLQMRRLATALQKEIGERTHAETVMVKEYRDKIDA
CAE52973(VP5)    (151) LNKAVTSYNKILTEEDLQMRRLATALQKEIGERTHAETVMVKEYRDKIDA
CAE52974(VP5)    (151) LNKAVTSYNKILTEEDLQMRRLATALQKEIGERTHAETVMVKEYRDKIDA
CAE52979(VP5)    (151) LNKAVTSYNKILTEEDLQMRRLANALQKEIGERTHAETVMVKEYRNKIDA
CAE52991(VP5)    (151) LNKAVTSYNKILTEEDLQMRRLATALQKEVSERTHAETVMVKEYRNKIDA 201                                               250
ACB59233(VP5)    (201) LKNAIEVERDGMQEEAIQEIAGMTADVLEAASEEVPLIGAGMATAVATGR
ACB59234(VP5)    (201) LKNAIEVERDGMQEEAIQEIAGMTADVLEAASEEVPLIGAGMATAVATGR
SEQ ID NO:10     (201) LKNAIEVERDGMQEEAIQEIAGMTADVLEAASEEVPLIGAGMATAVATGR
ACR58462(VP5)    (201) LKNAIEVERDGMQEEAIQEIAGMTADVLEAASEEVPLIGAGMATAVATGR
CAE53011(VP5)    (201) LKNAIEVERDGMQEEAIQEIAGMTADVLEAASEEVPLIGAGMATAVATGR
CAE52973(VP5)    (201) LKNAIEVERDGMQEEAIQEIAGMTADVLEAASEEVPLIGAGMATAVATGR
CAE52974(VP5)    (201) LKNAIEVERDGMQEEAIQEIAGMTADVLEAASEEVPLIGAGMATAVATGR
CAE52979(VP5)    (201) LKNAIEIERDGMQEEAIQEIAGMTADVLEAASEEVPLIGAGMATAVATGR
CAE52991(VP5)    (201) LKSAIEIERDGMQEEAIQEIAGMTADVLEAASEEVPLIGAGMATAVATGR
```

Figure 28B

```
                      251                                                    300
ACB59233(VP5)   (251) AIEGAYKLKKVINALSGIDLTHLRTPKIEPSVVSTILEYRTKEIPDNALA
ACB59234(VP5)   (251) AIEGAYKLKKVINALSGIDLTHLRTPKIEPSVVSTILEYRTKEIPDNALA
SEQ ID NO:10    (251) AIEGAYKLKKVINALSGIDLTHLRTPKIEPSVVSTILEYRTKEIPDNALA
ACR58462(VP5)   (251) AIEGAYKLKKVINALSGIDLTHLRTPKIEPSVVSTILEYRAKEIPDNALA
CAE53011(VP5)   (251) AIEGAYKLKKVINALSGIDLTHLRTPKIEPSVVSTILEYRAKEIPDNALA
CAE52973(VP5)   (251) AIEGAYKLKKVINALSGIDLTHLRTPKIEPSVVSTILEYRTKEIPDNALA
CAE52974(VP5)   (251) AIEGAYKLKKVINALSGIDLTHLRTPKIEPSVVSTILEYRTKEIPDNALA
CAE52979(VP5)   (251) AIEGAYKLKKVINALSGIDLTHLRTPKIEPSVVSTILEYRTKDIPDSALA
CAE52991(VP5)   (251) AIEGAYKLKKVINALSGIDLTHLRTPKIEPSVVSTILEYRTKEIPDNALA 301                                                    350
ACB59233(VP5)   (301) VSVLSKNRAIQENHKELMHIKNEILPRFKKAMDEEKEICGIEDKVIHPKV
ACB59234(VP5)   (301) VSVLSKNRAIQENHKELMHIKNEILPRFKKAMDEEKEICGIEDKVIHPKV
SEQ ID NO:10    (301) VSVLSKNRAIQENHKELMHIKNEILPRFKKAMDEEKEICGIEDKVIHPKV
ACR58462(VP5)   (301) VSVLSKNRAIQENHKELMHIKNEILPRFKKAMDEEKEICGIEDKVIHPKV
CAE53011(VP5)   (301) VSVLSKNRAIQENHKELMHIKNEILPRFKKAMDEEKEICGIEDKVIHPKV
CAE52973(VP5)   (301) VSVLSKNRAIQENHKELMHIKNEILPRFKKAMDEEKEICGIEDRVIHPKV
CAE52974(VP5)   (301) VSVLSKNRAIQENHKELMHIKNEILPRFKKAMDEEKEICGIEDRVIHPKV
CAE52979(VP5)   (301) VSVLSKNRAIQENHKELVHIQDEILPRFKKAMDEEKEICGIEDKVIHPKV
CAE52991(VP5)   (301) VSILSKNRAIQENHKELMHIKDEILPRFKKAMDEEKEICGIEDKTIHPKV 351                                                    400
ACB59233(VP5)   (351) MMKFKIPRAQQPQIHVYSAPWDSDDVFSFHCISHHHANESFTLGFDLSID
ACB59234(VP5)   (351) MMKFKIPRAQQPQIHVYSAPWDSDDVFSFHCISHHHANESFTIGFSSID
SEQ ID NO:10    (351) MMKFKIPRAQQPQIHVYSAPWDSDDVFSFHCISHHHANESFTLGFDLSID
ACR58462(VP5)   (351) MMKFKIPRAQQPQIHVYSAPWDSDDVFSFHCISHHHANESFTLGFDLSID
CAE53011(VP5)   (351) MMKFKIPRAQQPQIHVYSAPWDSDDVFSFHCISHHHANESFTLGFDLSID
CAE52973(VP5)   (351) MMKFKIPRAQQPQIHVYSAPWDSDDVFSFHCISHHHANESFTLGFDLSID
CAE52974(VP5)   (351) MMKFKIPRAQQPQIHVYSAPWDSDDVFSFHCISHHHANESFTLGFDLSID
CAE52979(VP5)   (351) MMRFKIPRAQQPQIHVYSAPWDSDDVFSFHCISHHHANESFTLGFDLSID
CAE52991(VP5)   (351) MMKFKIPRAQQPQIHVYSAPWDSDDVFSFHCISHHHANESFTLGFDLSID 401                                                    450
ACB59233(VP5)   (401) LVHYEDLTAHGHALGAAQAAAGRTLTEAYREFLNLAISNAFGTQMHTRRL
ACB59234(VP5)   (401) LVHYEDLTAHGHALGAAQAAAGRTLTEAYREFLNLAISNAFGTQMHTRRL
SEQ ID NO:10    (401) LVHYEDLTAHWHALGAAQAAAGRTLTEAYREFLNLAISNAFGTQMHTRRL
ACR58462(VP5)   (401) LVHYEDLTAHWHALGAAQTAAGRTLTEAYREFLNLAISNAFGTQMHTRRL
CAE53011(VP5)   (401) LVHYEDLTAHWHALGAAQTAAGRTLTEAYREFLNLAISNAFGTQMHTRRL
CAE52973(VP5)   (401) LVHYEDLTAHWHALGAAQTAAGRTLTEAYREFLNLAISNAFGTQMHTRRL
CAE52974(VP5)   (401) LVHYEDLTAHWHALGAAQTAAGRTLTEAYREFLNLAISNAFGTQMHTRRL
CAE52979(VP5)   (401) LVHYEDLTAHWHALGAAQMAMGRTLSEAYREFLNMAISNSFGTQMHTRRL
CAE52991(VP5)   (401) LVHYEDLTAHWHALGAAQMAAGRTLTEAYREFLNMAISNVLGTQMHTRRL 451                                                    500
ACB59233(VP5)   (451) VRSKTVHPIYLGSLHYDISPSDLRGNAQRIVYDDELQMHILRGPIHFQRR
ACB59234(VP5)   (451) VRSKTVHPIYLGSLHYDISPSDLRGNAQRIVYDDELQMHILRGPIHFQRR
SEQ ID NO:10    (451) VRSKTVHPIYLGSLHYDISPSDLRGNAQRIVYDDELQMHILRGPIHFQRR
ACR58462(VP5)   (451) VRSKTVHPIYLGSLHYDISPSDLRGNAQRIVYDDELQMHILRGPIHFQRR
CAE53011(VP5)   (451) VRSKTVHPIYLGSLHYDISPSDLRGNAQRIVYDDELQMHILRGPIHFQRR
CAE52973(VP5)   (451) VRSKTVHPIYLGSLHYDISPSDLRGNAQRIVYDDELQMHILRGPIHFQRR
CAE52974(VP5)   (451) VRSKTVHPIYLGSLHYDISPSDLRGNAQRIVYDDELQMHILRGPIHFQRR
CAE52979(VP5)   (451) VRSKTVHPIYLGSLHYDISPPDLRGNAQRIVYDDELQMHILRGPIHFQRR
CAE52991(VP5)   (451) VRSKTVHPIYLGSMHYDISPSDLRGNAQRIVYDDELQMHILRGPIHFQRR
```

Figure 28C

```
                              501                        527
ACB59233(VP5)   (501) AILGALKFGCKVLGDRLDVPLFLRNA-
ACB59234(VP5)   (501) AILGALKFGCKVLGDRLDVPLFLRNA-
SEQ ID NO:10    (501) AILGALKFGCKVLGDRLDVPLFLRNA-
ACR58462(VP5)   (501) AILGALKFGCKVLGDRLDVPLFLRNA-
CAE53011(VP5)   (501) AILGALKFGCKVLGDRLDVPLFLRNA-
CAE52973(VP5)   (501) AILGALKFGCKVLGDRLDVPLFLRNA-
CAE52974(VP5)   (501) AILGALKFGCKVLGDRLDVPLFLRNA-
CAE52979(VP5)   (501) AILGALKFGCKVLGDRLDVPLFLRNA-
CAE52991(VP5)   (501) AILGALKFGCKVLGDRLDVPLFLRNA-
```

Sequence identity percentage (performed using VNTI software)

SEQ ID NO:10 v. ACB59233 (SEQ ID NO:18) = 99.6%
SEQ ID NO:10 v. ACB59234 (SEQ ID NO:19) = 98.7%
SEQ ID NO:10 v. ACR58462 (SEQ ID NO:20) = 99.4%
SEQ ID NO:10 v. CAE52973 (SEQ ID NO:21) = 99.8%
SEQ ID NO:10 v. CAE52974 (SEQ ID NO:22) = 99.4%
SEQ ID NO:10 v. CAE52979 (SEQ ID NO:23) = 95.2%
SEQ ID NO:10 v. CAE52991 (SEQ ID NO:24) = 95.1%
SEQ ID NO:10 v. CAE53011 (SEQ ID NO:25) = 99.6%

SEQUENCE LISTING

```
<160> NUMBER OF SEQ ID NOS: 32

<210> SEQ ID NO 1
<211> LENGTH: 2886
<212> TYPE: DNA
<213> ORGANISM: artificial sequence
<220> FEATURE:
<223> OTHER INFORMATION: BTV VP2 wild-type DNA

<400> SEQUENCE: 1
atggatgagc taggcatccc agtttataag agaggatttc ccgaacatct gcttcgtggt      60
tatgagttta taatagatgt tggaactaag atagaaagtt ttggtggacg tcatgatgta     120
acgaaaatac cagaaatgaa tgcatatgac atcaagcagg aaagtatccg gaccgcatta     180
tggtataacc cgataagaaa tgatggtttt gtgttgccgc gagtgttgga tatcacattg     240
aggggttacg atgaaagacg ggcggttgtt gaaagtacga gacacaagag tttccacacg     300
aatgaccagt gggtgcagtg gatgatgaaa gattcgatgg acgctcagcc tttaaaggtt     360
gggttagatg atcaaagtag gaatgtggct cactcgttac ataattgcgt agtcaaaatc     420
gattcgaaga aggctgatac tatgtcttat catgtagagc cgattgagga cgcgtcaaag     480
gggtgtttgc atacgagaac catgatgtgg aatcacctag tacgaataga aacatttcat     540
gcagcacagg aggtggcata tactcttaaa cctacttatg atatcgtggt ccacgctgaa     600
aggagagatc gtagtcaacc gtttaggccg ggggatcaga cattaattaa ttttgggaga     660
ggtcagaagg tgacgatgaa ccacaattca tatgataaga tggttgaggg attagcgcat     720
ttagtgatta gagggaaaat tccagaggtg attagagatg atatcgctag cttggatgag     780
atatgtaata ggtggataca gagtaggcac gaccctggag aaataaaggc atatgaacta     840
tgtaaaatat tatcaacgat cggtcgaaaa gttctcgatc gagagaaaga accagaggat     900
gaggcaagtc tatcgatccg atttcaagag gcgatcgaca taagttccg acaacatgat      960 cctgagcgcc tgaagatatt tgagcatagg aatcagcgta gagatgagga tcggttctat    1020
attctgttga tgattgcagc ctccgacact tttaacacac gagtgtggtg gtcgaaccca    1080
tatccatgtt taagaggaac cttaattgca tcggaaacga aactaggtga cgtttattca    1140
atgatgcgct catggtacga ttggagtgtt cgaccaacct atacgcctta cgaaaaaacg    1200
agggaacagg aaaaatatat ttatggacgg gttaacctgt ttgatttcgt cgcggaacct    1260
gggattaaaa tcgttcattg ggaatatagg ctgaatcatt ccacccggga gataacctat    1320
gcacaaggga acccatgtga tttatacccca gaggatgatg atgtaatagt cacaaagttc    1380
gacgatgtcg cgtatggtca aatgatcaat gagatgataa atgggggttg gaatcaagag    1440
cagttcaaga tgcataaaat tttaaaatca gaaggtaacg ttctaacgat agattttgaa    1500
aaggatgcaa agctaacaac caacgaaggc gtaacaatgc cagaatattt caataagtgg    1560
ataatcgctc cgatgttcaa cgctaagcta cgtataaaac atgaagagat tgcgcagcgt    1620
caaagtgatg acccgatggt aaaacgtact ttatcaccta ttaccgcaga tccaatcgaa    1680
ttacaaagat tgactttggc gcgattttac gacattcgtc ccgctttaag aggacaggca    1740 cttttcgcgac aacaggcaca gtccacttac gacgaagaga tatcgaaaag acaggattat    1800
```

```
gcagagatat tgaaacgtcg tggaattgtg caaattccaa agaaaccttg cccaacagta    1860
acggcccagt atacgttgga acgttatgcc ttgttcatta tcagtatcct acaacagcat    1920
gtagtacgag attgcgacga ggaggcggta tacgaacatc cgaaagcgga ccatgaactt    1980
gaaatatttg gcgagagcat tgtggatatc tctcaagtga ttattctagc ttttgacttg    2040
atattcgaga gaagaaggag ggttagagat gtgtatgaat cgcggcacat aattgcgcgt    2100
attaggagaa tgcgaggtaa agaaagattg aacgtgatcg cggagttttt cccaaccctat   2160 ggggtcttc taaatgggtt aaacagcgcc accgtagtgc agaatattat gtatttaaac     2220
tttctcccat tgtatttttt ggtaggcgat aacatgatat actctcatag gcagtggtct    2280
attcctttac ttctatatac tcatgaagtg atggtggtcc cattagaagt tggttcatac    2340
aatgatcggt gcggattaat tgcgtacctg aatacatgg ttttctttcc ctcaaaggcg     2400
attcgattta gcaaactgaa tgaagcgcag cccaagattg cacgcgagat gcttaagtac    2460
tacgctaata ctacggtata tgatggggga gtcaactaca acgtcgtgac gacgaagcag    2520
cttctatatg agacatatct cgcttcgtta tgtgggggta tttctgatgg tattgtctgg    2580
tatttaccga tcacacatcc gaacaaatgc attgtagcga tcgaggtatc tgatgaaaga    2640
gttccggcta gcattagagc ggggcgtata aggctaagat ttccgctgag cgcgcgacat   2700
ctaaaagggg ttgtaatcat acaaattgat gaggagggcg aatttacagt gtatagcgag    2760
gggattgtgt ctcatcgggt gtgtaaaaag aatttactca gtatatgtg cgatattata     2820 ttactgaagt tttcggggca cgttttttggt aacgacgaga tgctgacaaa acttctcaac    2880
gtatga                                                              2886
```

<210> SEQ ID NO 2
<211> LENGTH: 2886
<212> TYPE: DNA
<213> ORGANISM: artificial sequence
<220> FEATURE:
<223> OTHER INFORMATION: BTV VP2 codon-optimzied for mammalian
      expression

<400> SEQUENCE: 2

```
atggacgagc tgggcatccc cgtgtacaag agaggcttcc ccgagcacct gctgcgcggc      60
tacgagttca tcatcgacgt gggcaccaag atcgagagcg tgggcggcag acacgacgtg    120
accaagatcc ccgagatgaa cgcctacgac atcaagcagg aaagcatcag aaccgccctg    180
tggtacaacc ccatcagaaa cgacggcttc gtgctgccca gagtgctgga catcaccctg    240 agggggctacg acgagaagag agccgtggtg gagagcacca gacacaagag cttccacacc    300
aacgaccagt gggtgcagtg gatgatgaag acagcatgg acgcccagcc cctgaaagtg     360
ggcctggacg accagagcag aaacgtggcc cacagcctgc acaactgcgt ggtgaagatc     420
gacagcaaga agccgacac catgagctac acgtggagc ccatcgagga cgccagcaag      480
ggctgcctgc acaccagaac catgatgtgg aaccacctgg tgcggatcga gacattccac    540
gccgcccagg aagtggccta caccctgaag cccaccatg acatcgtggt gcacgccgag     600
cggagagaca gaagccagcc cttcagaccc ggcgaccaga ccctgatcaa cttcggcaga    660
ggccagaaag tgaccatgaa ccacaacagc tacgacaaga tggtggaagg cctggcccac    720
ctggtgatca gaggcaagat ccctgaagtg atccgggacg acattgccag cctggacgag    780
atctgcaaca atggattca gagccggcac gaccccggcg agatcaaggc ctacgagctg    840
tgcaagatcc tgagcaccat cggcagaaag gtgctggaca gagagaaaga gcccgaggac    900
```

```
gaggccagcc tgagcatcag attccaggaa gccatcgaca caagttcag acagcacgac      960 cctgagagac tgaagatctt cgagcacaga accagcggc gggacgagga cagattctac     1020
atcctgctga tgatcgccgc cagcgacacc ttcaacacca gagtgtggtg gagcaacccc     1080 taccctgcc tgagaggcac cctgatcgcc agcgagacaa agctgggcga cgtgtacagc     1140
atgatgcggt cttggtacga ttggagcgtg cggcccacct acacccccta cgagaaaacc     1200
agagagcagg aaaagtacat ctacggccgc gtgaacctgt tcgacttcgt ggccgagccc     1260
ggcatcaaga tcgtgcactg ggagtacaga ctgaaccaca gcaccagaga gatcacctac     1320
gcccagggca cccctgcga cctgtacccc gaggatgacg acgtgatcgt gaccaagttc     1380
gacgacgtgg cctacggcca gatgatcaac gagatgatca atggcggctg gaaccaggaa     1440
cagttcaaga tgcacaagat tctgaagagc gagggcaacg tgctgaccat cgacttcgag     1500
aaggacgcca agctgaccac caacgagggc gtgaccatgc ccgagtactt caacaagtgg     1560
atcattgccc ccatgttcaa tgccaagctg cggatcaagc acgaggaaat cgcccagaga     1620
cagagcgacg accccatggt gaagagaacc ctgagcccca tcaccgccga ccccatcgag     1680
ctgcagagac tgaccctggc cagattctac gacatcagac cagctctgcg cgggcaggct     1740
ctgagcgaca gcaggcccca gagcacctac gacgaagaga tcagcaagag acaggactac     1800
gccgagatcc tgaagagaag aggcatcgtg cagatcccca gaagccctg ccccaccgtc     1860 accgcccagt acaccctgga agatacgcc ctgttcatca tcagcatcct gcagcagcac     1920
gtggtgcggg actgcgacga ggaagccgtg tacgagcacc ccaaggccga ccacgagctg     1980
gaaatcttcg gcgagagcat cgtggacatc tctcaggtga tcatcctggc cttcgacctg     2040
atcttcgaga aaggcggag agtgcgggac gtgtacgaga gcagacacat cattgccaga     2100
atcagaagaa tgcggggcaa agaacggctg aacgtgatcg ccgagttctt ccccaccttac    2160 ggcggcctgc tgaacggcct gaacagcgcc accgtggtgc agaacatcat gtacctgaac     2220
tttctgcccc tgtacttcct ggtgggcgac aacatgatct acagccacag acagtggagc     2280
atccccctgc tgctgtacac ccacgaagtg atggtggtgc ctctggaagt gggaagctac     2340
aacgacagat gcggcctgat cgcctacctg aatacatgg tgttcttccc tagcaaggcc     2400
atcagattca gcaagctgaa cgaggcccag cccaagatcg cagagagat gctgaagtac     2460 tacgccaaca ccaccgtgta cgacggcggc gtgaactaca acgtggtgac caccaagcag     2520
ctgctgtacg agacatacct ggccagcctg tgcggcggca tcagcgacgg catcgtgtgg     2580
tatctgccca tcacccaccc caacaagtgc atcgtggcca tcgaggtgtc cgacgagaga     2640
gtgcccgcca gcatcagggc cggcagaatc agactgagat tccccctgag cgccagacac     2700
ctgaagggcg tggtgatcat tcagatcgac gaagagggcg agttcaccgt gtactccgag     2760
ggcatcgtgt cccacagagt gtgcaagaag aacctgctga gtatatgtg cgacatcatt     2820 ctgctgaagt tcagcggcca cgtgttcggc aacgacgaga tgctgaccaa gctgctgaac     2880
gtgtga                                                                2886
```

<210> SEQ ID NO 3
<211> LENGTH: 2886
<212> TYPE: DNA
<213> ORGANISM: artificial sequence
<220> FEATURE:
<223> OTHER INFORMATION: BTV VP2 codon-optimized for duckweed expression

<400> SEQUENCE: 3

```
atggacgagc tggggatccc cgtgtacaag cgcgggttcc ccgagcacct gctccgcggc       60
```

| | |
|---|---|
| tacgagttca tcatcgacgt gggcaccaag atcgagtccg tgggcgggag gcacgacgtg | 120 |
| accaagatcc cggagatgaa cgcctacgac atcaagcagg agtccatccg gacggccctc | 180 |
| tggtacaacc ccatccggaa cgacggcttc gtgctcccgc gggtcctgga catcaccctc | 240 |
| cggggggtacg acgagcgccg ggccgtggtc gagtccaccc gccacaagag cttccacacg | 300 |
| aacgaccaat gggtgcagtg gatgatgaag gactcgatgg atgcgcagcc cctgaaggtc | 360 |
| gggctggacg atcaatcccg caacgtggcc cacagcctcc acaactgcgt cgtgaagatc | 420 |
| gacagcaaga aagcggacac gatgtcgtac cacgtcgagc cgatcgagga cgcctccaag | 480 |
| gggtgcctcc acaccccgcac gatgatgtgg aaccacctgg tccgcatcga gaccttccac | 540 |
| gcggcccagg aggtcgcgta caccctcaag ccgacctacg acatcgtggt ccacgcggag | 600 |
| cgcagagacc gctcccagcc gttcagaccc ggcgaccaga cgctgatcaa cttcggcagg | 660 |
| gggcagaagg tgaccatgaa tcacaacagc tacgacaaga tggtcgaggg gctcgcgcac | 720 |
| ctcgtgatcc gcgggaagat ccccgaggtc atccgcgacg atatcgcctc cctggacgag | 780 |
| atctgcaaca ggtggatcca gagccgccac gaccccggcg agatcaaggc ctacgagctg | 840 |
| tgcaagatcc tcagcaccat cggccgcaag gtcctggaca gggagaaaga gcccgaggac | 900 |
| gaggcctccc tctccatccg cttccaggag gcgatcgaca acaagttccg ccagcacgac | 960 |
| ccggagaggc tgaagatctt cgaacaccgg aaccagcggc gcgacgagga cagattctac | 1020 |
| atcctcctga tgatcgccgc gtccgacacg ttcaacacga gagtgtggtg gtccaacccc | 1080 |
| tacccgtgtc tcaggggtac gctcatcgcc agcgagacca agctcgggga cgtttactcg | 1140 |
| atgatgcgca gctggtacga ctggtccgtc cgcccgacct acacgcccta cgagaagacc | 1200 |
| cgcgagcagg aaaagtacat ctacggccgc gtcaacctgt tcgacttcgt cgcggagccc | 1260 |
| ggcatcaaga tcgtccactg ggaataccgg ctgaaccact ccacccgcga gatcacctac | 1320 |
| gcgcagggta acccctgcga cctctatccg gaggacgacg acgtcatcgt gaccaagttc | 1380 |
| gacgacgtcg cctacggcca gatgatcaac gagatgatca acggcgggtg gaaccaggag | 1440 |
| cagttcaaga tgcacaaaat cctgaagagc gaggggaacg ttctcaccat cgacttcgag | 1500 |
| aaggacgcca agctgaccac gaacgagggg gtgaccatgc ccgagtactt caacaagtgg | 1560 |
| atcatcgccc ccatgttcaa cgccaagctc cgcatcaagc acgaggaaat cgcccagcgc | 1620 |
| cagtcggacg accccatggt taagaggacc ctctcgccca tcaccgccga ccccatcgag | 1680 |
| ctgcagcggc tcaccctggc ccgcttctac gacatccgcc ctgctctccg cggccaggcc | 1740 |
| ctgagccgcc agcaggccca gagcacctac gacgaggaga tctccaagcg ccaggactac | 1800 |
| gccgagatcc tcaagcggag ggggatcgtg cagatcccca gaagccctg cccgacggtg | 1860 |
| accgccagt acaccctcga gcgctacgcg ctcttcatca tcagcatcct gcagcagcac | 1920 |
| gtcgtccgcg actgcgacga ggaggccgtt tacgagcacc cgaaggcgga ccacgagctg | 1980 |
| gagatcttcg gggagtccat cgtggacatc tcccaggtca tcatcctcgc gttcgacctg | 2040 |
| atcttcgagc ggcgcagacg cgtgcgcgac gtctacgaga gccggcacat catcgcccgc | 2100 |
| atccgccgga tgcggggcaa ggagagactc aacgtgatcg ccgagttctt cccgacttac | 2160 |
| ggcgggctgc tcaatggcct gaactccgct accgtcgtga gaacatcat gtacctcaac | 2220 |
| ttcctgccgc tctacttcct ggtcggcgac aacatgatct actcccaccg ccagtggtcc | 2280 |
| atcccgctgc tcctgtacac ccacgaggtg atggtcgtgc cgctcgaggt gggctcctat | 2340 |
| aacgaccgct gcggcctcat cgcctacctc gagtacatgg tcttcttccc ttccaaggcc | 2400 |

-continued

```
atcagattct ccaagctcaa cgaggcccag ccgaagatcg ctcgggagat gctcaagtac    2460
tacgcgaaca cgaccgtgta cgacggcggg gtgaactaca acgtcgtgac cacgaagcag    2520
ctcctgtacg agacgtacct cgccagcctc tgcggcggga tctcggacgg tatcgtgtgg    2580
tatctgccga tcacccaccc caacaagtgc atcgtcgcca tcgaggtgtc cgacgagcgg    2640
gtgcccgcct cgatcagagc cggccgcatc cgcctccgct tcccctgag cgcccgccac    2700 ctcaagggcg tcgtgatcat ccagatcgac gaggaggggg agttcacggt gtactcggag    2760
ggcatcgtgt cccaccgggt gtgcaagaag aacctgctca gtacatgtg cgacatcatc    2820 ctgctcaagt tctcgggcca cgtcttcggc aacgacgaga tgctgaccaa gctcctgaac    2880
gtgtaa                                                               2886
```

<210> SEQ ID NO 4
<211> LENGTH: 961
<212> TYPE: PRT
<213> ORGANISM: artificial sequence
<220> FEATURE:
<223> OTHER INFORMATION: BTV VP2 protein

<400> SEQUENCE: 4

```
Met Asp Glu Leu Gly Ile Pro Val Tyr Lys Arg Gly Phe Pro Glu His
1               5                  10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
    210                 215                 220

Thr Met Asn His Asn Ser Tyr Asp Lys Met Val Glu Gly Leu Ala His
225                 230                 235                 240

Leu Val Ile Arg Gly Lys Ile Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270
```

-continued

```
Gly Glu Ile Lys Ala Tyr Glu Leu Cys Lys Ile Leu Ser Thr Ile Gly
            275                 280                 285

Arg Lys Val Leu Asp Arg Glu Lys Glu Pro Glu Asp Glu Ala Ser Leu
        290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Arg Asp Glu
                325                 330                 335

Asp Arg Phe Tyr Ile Leu Leu Met Ile Ala Ala Ser Asp Thr Phe Asn
            340                 345                 350

Thr Arg Val Trp Trp Ser Asn Pro Tyr Pro Cys Leu Arg Gly Thr Leu
        355                 360                 365

Ile Ala Ser Glu Thr Lys Leu Gly Asp Val Tyr Ser Met Met Arg Ser
370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                405                 410                 415

Val Ala Glu Pro Gly Ile Lys Ile Val His Trp Glu Tyr Arg Leu Asn
            420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Val Ala
450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Ser Glu Gly Asn Val Leu Thr
                485                 490                 495

Ile Asp Phe Glu Lys Asp Ala Lys Leu Thr Thr Asn Glu Gly Val Thr
            500                 505                 510

Met Pro Glu Tyr Phe Asn Lys Trp Ile Ile Ala Pro Met Phe Asn Ala
        515                 520                 525

Lys Leu Arg Ile Lys His Glu Glu Ile Ala Gln Arg Gln Ser Asp Asp
530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                565                 570                 575

Arg Gly Gln Ala Leu Ser Arg Gln Gln Ala Gln Ser Thr Tyr Asp Glu
            580                 585                 590

Glu Ile Ser Lys Arg Gln Asp Tyr Ala Glu Ile Leu Lys Arg Arg Gly
        595                 600                 605

Ile Val Gln Ile Pro Lys Lys Pro Cys Pro Thr Val Thr Ala Gln Tyr
610                 615                 620

Thr Leu Glu Arg Tyr Ala Leu Phe Ile Ile Ser Ile Leu Gln Gln His
625                 630                 635                 640

Val Val Arg Asp Cys Asp Glu Glu Ala Val Tyr Glu His Pro Lys Ala
                645                 650                 655

Asp His Glu Leu Glu Ile Phe Gly Glu Ser Ile Val Asp Ile Ser Gln
            660                 665                 670

Val Ile Ile Leu Ala Phe Asp Leu Ile Phe Glu Arg Arg Arg Val
        675                 680                 685

Arg Asp Val Tyr Glu Ser Arg His Ile Ile Ala Arg Ile Arg Arg Met
```

```
                690             695            700
Arg Gly Lys Glu Arg Leu Asn Val Ile Ala Glu Phe Phe Pro Thr Tyr
705                 710                715                720

Gly Gly Leu Leu Asn Gly Leu Asn Ser Ala Thr Val Val Gln Asn Ile
                725                730                735

Met Tyr Leu Asn Phe Leu Pro Leu Tyr Phe Leu Val Gly Asp Asn Met
            740                745                750

Ile Tyr Ser His Arg Gln Trp Ser Ile Pro Leu Leu Leu Tyr Thr His
        755                760                765

Glu Val Met Val Val Pro Leu Glu Val Gly Ser Tyr Asn Asp Arg Cys
770                775                780

Gly Leu Ile Ala Tyr Leu Glu Tyr Met Val Phe Phe Pro Ser Lys Ala
785             790                795                800

Ile Arg Phe Ser Lys Leu Asn Glu Ala Gln Pro Lys Ile Ala Arg Glu
                805                810                815

Met Leu Lys Tyr Tyr Ala Asn Thr Thr Val Tyr Asp Gly Gly Val Asn
            820                825                830

Tyr Asn Val Val Thr Thr Lys Gln Leu Leu Tyr Glu Thr Tyr Leu Ala
        835                840                845

Ser Leu Cys Gly Gly Ile Ser Asp Gly Ile Val Trp Tyr Leu Pro Ile
850                855                860

Thr His Pro Asn Lys Cys Ile Val Ala Ile Glu Val Ser Asp Glu Arg
865             870                875                880

Val Pro Ala Ser Ile Arg Ala Gly Arg Ile Arg Leu Arg Phe Pro Leu
                885                890                895

Ser Ala Arg His Leu Lys Gly Val Val Ile Ile Gln Ile Asp Glu Glu
            900                905                910

Gly Glu Phe Thr Val Tyr Ser Glu Gly Ile Val Ser His Arg Val Cys
        915                920                925

Lys Lys Asn Leu Leu Lys Tyr Met Cys Asp Ile Ile Leu Leu Lys Phe
930                935                940

Ser Gly His Val Phe Gly Asn Asp Glu Met Leu Thr Lys Leu Leu Asn
945             950                955                960

Val
```

<210> SEQ ID NO 5
<211> LENGTH: 2916
<212> TYPE: DNA
<213> ORGANISM: artificial sequence
<220> FEATURE:
<223> OTHER INFORMATION: BTV VP2 codon-optimized for mammalian
      expression with c-myc attached

<400> SEQUENCE: 5

```
atggacgagc tgggcatccc cgtgtacaag agaggcttcc ccgagcacct gctgcgcggc      60
tacgagttca tcatcgacgt gggcaccaag atcgagagcg tgggcggcag acacgacgtg     120
accaagatcc ccgagatgaa cgcctacgac atcaagcagg aaagcatcag aaccgccctg     180
tggtacaacc ccatcagaaa cgacggcttc gtgctgccca gagtgctgga catcaccctg     240
aggggctacg acgagagaag agccgtggtg gagagcacca gacacaagag cttccacacc     300
aacgaccagt gggtgcagtg gatgatgaag gacagcatgg acgcccagcc cctgaaagtg     360
ggcctggacg accagagcag aaacgtggcc cacagcctgc acaactgcgt ggtgaagatc     420
gacagcaaga agccgacac catgagctac cacgtggagc ccatcgagga cgccagcaag     480
```

```
ggctgcctgc acaccagaac catgatgtgg aaccacctgg tgcggatcga gacattccac    540
gccgcccagg aagtggccta caccctgaag cccacctatg acatcgtggt gcacgccgag    600
cggagagaca gaagccagcc cttcagaccc ggcgaccaga ccctgatcaa cttcggcaga    660
ggccagaaag tgaccatgaa ccacaacagc tacgacaaga tggtggaagg cctggcccac    720
ctggtgatca gaggcaagat ccctgaagtg atccgggacg acattgccag cctggacgag    780
atctgcaaca gatggattca gagccggcac gaccccggcg agatcaaggc ctacgagctg    840
tgcaagatcc tgagcaccat cggcagaaag gtgctggaca gagagaaaga gcccgaggac    900
gaggccagcc tgagcatcag attccaggaa gccatcgaca caagttcag acagcacgac    960
cctgagagac tgaagatctt cgagcacaga aaccagcggc gggacgagga cagattctac   1020
atcctgctga tgatcgccgc cagcgacacc ttcaacacca gagtgtggtg agcaacccc    1080
taccctgcc tgagaggcac cctgatcgcc agcgagacaa agctgggcga cgtgtacagc   1140
atgatgcggt cttggtacga ttggagcgtg cggcccacct acacccccta cgagaaaacc   1200
agagagcagg aaaagtacat ctacggccgc gtgaacctgt tcgacttcgt ggccgagccc   1260
ggcatcaaga tcgtgcactg ggagtacaga ctgaaccaca gcaccagaga gatcacctac   1320
gcccagggca acccctgcga cctgtacccc gaggatgacg acgtgatcgt gaccaagttc   1380
gacgacgtgg cctacggcca gatgatcaac gagatgatca atggcggctg gaaccaggaa   1440
cagttcaaga tgcacaagat tctgaagagc gagggcaact gctgaccat cgacttcgag   1500
aaggacgcca agctgaccac caacgagggc gtgaccatgc ccgagtactt caacaagtgg   1560
atcattgccc ccatgttcaa tgccaagctg cggatcaagc acgaggaaat cgcccagaga   1620
cagagcgacg accccatggt gaagagaacc ctgagcccca tcaccgccga ccccatcgag   1680
ctgcagagac tgaccctggc cagattctac gacatcagac cagctctgcg cgggcaggct   1740
ctgagcagac agcaggccca gagcacctac gacgaagaga tcagcaagag acaggactac   1800
gccgagatcc tgaagagaag aggcatcgtg cagatcccca gaagccctg ccccaccgtc   1860
accgcccagt acaccctgga aagatacgcc ctgttcatca tcagcatcct gcagcagcac   1920
gtggtgcggg actgcgacga ggaagccgtg tacgagcacc ccaaggccga ccacgagctg   1980
gaaatcttcg gcgagagcat cgtggacatc tctcaggtga tcatcctggc cttcgacctg   2040
atcttcgaga gaaggcggag agtgcggac gtgtacgaga gcagacacat cattgccaga   2100
atcagaagaa tgcggggcaa agaacggctg aacgtgatcg ccgagttctt ccccacctac   2160
ggcggcctgc tgaacggcct gaacagcgcc accgtggtgc agaacatcat gtacctgaac   2220
tttctgcccc tgtacttcct ggtgggcgac aacatgatct acagccacag acagtggagc   2280
atcccctgc tgctgtacac ccacgaagtg atggtggtgc ctctggaagt gggaagctac   2340
aacgacagat gcggcctgat cgcctacctg gaatacatgg tgttcttccc tagcaaggcc   2400
atcagattca gcaagctgaa cgaggcccag cccaagatcg ccagagagat gctgaagtac   2460
tacgccaaca ccaccgtgta cgacggcggc gtgaactaca acgtggtgac caccaagcag   2520
ctgctgtacg agacatacct ggccagcctg tgcggcggca tcagcgacgg catcgtgtgg   2580
tatctgccca tcacccaccc caacaagtgc atcgtggcca tcgaggtgtc cgacgagaga   2640
gtgcccgcca gcatcagggc cggcagaatc agactgagat tcccctgag cgccagacac   2700
ctgaagggcg tggtgatcat tcagatcgac gaagagggcg agttcaccgt gtactccgag   2760
ggcatcgtgt cccacagagt gtgcaagaag aacctgctga gtatatgtg cgacatcatt   2820
ctgctgaagt tcagcggcca cgtgttcggc aacgacgaga tgctgaccaa gctgctgaac   2880
```

```
gtggagcaga agctgatcag cgaggaggac ctgtga                         2916

<210> SEQ ID NO 6
<211> LENGTH: 971
<212> TYPE: PRT
<213> ORGANISM: artificial sequence
<220> FEATURE:
<223> OTHER INFORMATION: BTV VP2 protein + c-myc

<400> SEQUENCE: 6

Met Asp Glu Leu Gly Ile Pro Val Tyr Lys Arg Gly Phe Pro Glu His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
    210                 215                 220

Thr Met Asn His Asn Ser Tyr Asp Lys Met Val Glu Gly Leu Ala His
225                 230                 235                 240

Leu Val Ile Arg Gly Lys Ile Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270

Gly Glu Ile Lys Ala Tyr Glu Leu Cys Lys Ile Leu Ser Thr Ile Gly
        275                 280                 285

Arg Lys Val Leu Asp Arg Glu Lys Glu Pro Glu Asp Glu Ala Ser Leu
    290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Arg Asp Glu
                325                 330                 335

Asp Arg Phe Tyr Ile Leu Leu Met Ile Ala Ala Ser Asp Thr Phe Asn
            340                 345                 350
```

```
Thr Arg Val Trp Trp Ser Asn Pro Tyr Pro Cys Leu Arg Gly Thr Leu
        355                 360                 365

Ile Ala Ser Glu Thr Lys Leu Gly Asp Val Tyr Ser Met Met Arg Ser
        370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                    405                 410                 415

Val Ala Glu Pro Gly Ile Lys Ile Val His Trp Glu Tyr Arg Leu Asn
            420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Val Ala
450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Ser Glu Gly Asn Val Leu Thr
                485                 490                 495

Ile Asp Phe Glu Lys Asp Ala Lys Leu Thr Thr Asn Glu Gly Val Thr
            500                 505                 510

Met Pro Glu Tyr Phe Asn Lys Trp Ile Ile Ala Pro Met Phe Asn Ala
        515                 520                 525

Lys Leu Arg Ile Lys His Glu Glu Ile Ala Gln Arg Gln Ser Asp Asp
        530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                    565                 570                 575

Arg Gly Gln Ala Leu Ser Arg Gln Gln Ala Gln Ser Thr Tyr Asp Glu
            580                 585                 590

Glu Ile Ser Lys Arg Gln Asp Tyr Ala Glu Ile Leu Lys Arg Arg Gly
        595                 600                 605

Ile Val Gln Ile Pro Lys Lys Pro Cys Pro Thr Val Thr Ala Gln Tyr
        610                 615                 620

Thr Leu Glu Arg Tyr Ala Leu Phe Ile Ile Ser Ile Leu Gln Gln His
625                 630                 635                 640

Val Val Arg Asp Cys Asp Glu Glu Ala Val Tyr Glu His Pro Lys Ala
                    645                 650                 655

Asp His Glu Leu Glu Ile Phe Gly Glu Ser Ile Val Asp Ile Ser Gln
            660                 665                 670

Val Ile Ile Leu Ala Phe Asp Leu Ile Phe Glu Arg Arg Arg Arg Val
        675                 680                 685

Arg Asp Val Tyr Glu Ser Arg His Ile Ile Ala Arg Ile Arg Arg Met
        690                 695                 700

Arg Gly Lys Glu Arg Leu Asn Val Ile Ala Glu Phe Phe Pro Thr Tyr
705                 710                 715                 720

Gly Gly Leu Leu Asn Gly Leu Asn Ser Ala Thr Val Val Gln Asn Ile
                    725                 730                 735

Met Tyr Leu Asn Phe Leu Pro Leu Tyr Phe Leu Val Gly Asp Asn Met
            740                 745                 750

Ile Tyr Ser His Arg Gln Trp Ser Ile Pro Leu Leu Leu Tyr Thr His
        755                 760                 765

Glu Val Met Val Val Pro Leu Glu Val Gly Ser Tyr Asn Asp Arg Cys
```

```
                  770             775              780
Gly Leu Ile Ala Tyr Leu Glu Tyr Met Val Phe Phe Pro Ser Lys Ala
785                 790                 795                 800

Ile Arg Phe Ser Lys Leu Asn Glu Ala Gln Pro Lys Ile Ala Arg Glu
                805                 810                 815

Met Leu Lys Tyr Tyr Ala Asn Thr Thr Val Tyr Asp Gly Gly Val Asn
                820                 825                 830

Tyr Asn Val Val Thr Thr Lys Gln Leu Leu Tyr Glu Thr Tyr Leu Ala
            835                 840                 845

Ser Leu Cys Gly Gly Ile Ser Asp Gly Ile Val Trp Tyr Leu Pro Ile
850                 855                 860

Thr His Pro Asn Lys Cys Ile Val Ala Ile Glu Val Ser Asp Glu Arg
865                 870                 875                 880

Val Pro Ala Ser Ile Arg Ala Gly Arg Ile Arg Leu Arg Phe Pro Leu
                885                 890                 895

Ser Ala Arg His Leu Lys Gly Val Val Ile Gln Ile Asp Glu Glu
                900                 905                 910

Gly Glu Phe Thr Val Tyr Ser Glu Gly Ile Val Ser His Arg Val Cys
            915                 920                 925

Lys Lys Asn Leu Leu Lys Tyr Met Cys Asp Ile Ile Leu Leu Lys Phe
            930                 935                 940

Ser Gly His Val Phe Gly Asn Asp Glu Met Leu Thr Lys Leu Leu Asn
945                 950                 955                 960

Val Glu Gln Lys Leu Ile Ser Glu Glu Asp Leu
                965                 970

<210> SEQ ID NO 7
<211> LENGTH: 1581
<212> TYPE: DNA
<213> ORGANISM: artificial sequence
<220> FEATURE:
<223> OTHER INFORMATION: BTV VP5 wild-type DNA

<400> SEQUENCE: 7
atgggtaaag tcatacggtc cttaagccga tttggcaaga aggtgggcaa cgcgttaacc      60
tctaataccg caaaaaagat ctatagtaca atcggaaaag cggcggaacg attcgctgag     120
agtgagatag gttcagcggc gatcgatgga ttggtacagg ggagcgtaca ttcaatcata     180 acggcgaat cttacggcga atctgtgaaa caagctgtgt tgttaaatgt gttggggagt     240
ggtgaggaaa ttcctgatcc gctaagccca ggagagcggg ggatacaagc taagttgaaa     300
gagttagagg atgagcaacg taatgaatta gttcgcttga atataatga taagattaag     360 gagaaatttg gaaagagct tgaggaggta caatttta tgaatgggga ggcgaatgct     420
gagattgaag atgagaagca gtttgatata ttgaacaagg cggtgacctc gtataacaaa     480
atccttacgg aagaagatct acagatgcgc cggctagcta cggcgttaca gaaagagatc     540
ggagaaagaa cacatgcgga gacggtcatg gtaaaagaat accgagataa aattgacgct     600 ttaaaaatg cgattgaggt agaaagagat ggcatgcaag aggaggcaat acaggagatt     660
gcggggatga ccgcagatgt gttagaggcg catcggagg aggttccgct gattggtgcg     720
gggatggcta cggctgtagc gacaggaaga gctatagaag gagcgtataa actcaaaaag     780
gtgattaacg ctctaagcgg gatcgatcta acgcatttgc gcaccccgaa atcgaaccct     840
agtgttgttt caactattct tgagtaccgc acaaaggaaa ttcctgataa cgctctagct     900
gttagtgttc tatcaaaaaa tcgcgcgatt caagaaaacc acaaagaact gatgcatatc     960
```

-continued

```
aagaatgaga tattacctag gtttaagaaa gcgatggatg aagaaaagga aatatgtggg   1020
atagaagaca aagtgatcca cccgaaggtc atgatgaagt tcaagattcc gagagctcaa   1080
cagccgcaga ttcatgtata cagtgctcca tgggattctg atgatgtgtt cttctttcat   1140
tgtatctcgc accatcatgc aaatgagtcg ttctttttag gtttcgattt gagcattgat   1200
ttagttcatt atgaagatct taccgcccat tggcatgcat tgggagcagc tcaagcagcg   1260
gcgggacgta cgttgactga agcgtataga gaatttttaa atttggcgat ctcaaatgca   1320
ttcggcacgc aaatgcacac gagaaggttg gttaggtcaa aaacggtaca tccaatttat   1380
ttaggttcct tgcattacga tatttccttt tcggatctgc gtggaaacgc tcagagaata   1440
gtttatgatg atgagctgca aatgcacata ctccgtgggc cgatacactt tcaaagacgt   1500
gcaatactgg gagctttgaa atttggatgt aaggttttgg gggaccgttt agacgtacca   1560
ctcttcttac gaaatgcttg a                                              1581
```

```
<210> SEQ ID NO 8
<211> LENGTH: 1581
<212> TYPE: DNA
<213> ORGANISM: artificial sequence
<220> FEATURE:
<223> OTHER INFORMATION: BTV VP5 codon-optimized for mammalian
      expression

<400> SEQUENCE: 8
```

```
atgggcaagg tgatcagaag cctgagcaga ttcggcaaga aggtgggcaa cgctctgacc     60
agcaacaccg ccaagaagat ctacagcacc atcggcaagg ctgccgaaag attcgccgag    120
agcgagatcg gcagcgccgc catcgacggc ctggtgcagg gaagcgtgca cagcatcatc    180
accggagaga gctacggaga gagcgtcaag caggccgtgc tgctgaacgt gctgggcagc    240
ggcgaggaga tccccgaccc cctgagccct ggcgagaggg gcatccaggc caagctgaaa    300
gaactggaag atgagcagag gaacgagctg gtgcggctga agtacaacga caagatcaag    360
gagaagttcg gcaaggaact ggaagaggtc tacaacttca tgaacggcga ggccaacgcc    420
gagatcgagg acgagaagca gttcgacatc ctgaacaagg ccgtgaccag ctacaacaag    480
atcctgaccg aggaggacct gcagatgaga aggctggcca ccgccctgca gaaggagatc    540
ggcgagagga cccacgccga gacagtgatg gtgaaggagt acagggacaa gatcgacgcc    600
ctgaagaacg ccatcgaggt ggagagggac ggcatgcagg aggaggccat tcaggaaatc    660
gccggcatga ccgccgacgt gctggaggct gccagcgagg aggtgcccct gatcggagct    720
ggaatggcta ccgctgtggc caccggcaga gccatcgagg gcgcctacaa gctgaagaag    780
gtgatcaacg ctctctccgg catcgacctg acccacctga ggacccccaa gatcgagccc    840
agcgtggtgt ccaccatcct ggagtacagg accaaggaga tccctgacaa cgccctggcc    900
gtgagcgtgc tgtccaagaa cagagccatt caggaaaacc acaaagaact gatgcacatc    960
aagaacgaga tcctgcccag gttcaaaaag gccatggacg aggagaagga gatctgcggc   1020
atcgaggaca aggtgatcca ccccaaggtg atgatgaagt tcaagatccc cagggcccag   1080
cagccccaga tccacgtgta cagcgccccc tgggacagcg acgacgtgtt cttcttccac   1140
tgcatcagcc accaccacgc caacgagtct ttcttcctgg gcttcgacct gtccatcgac   1200
ctggtgcact acgaggacct gaccgcccac tggcacgccc tgggagccgc tcaggccgct   1260
gctggcagaa ccctgaccga ggcctacaga gagttcctga acctggccat cagcaacgcc   1320
ttcggcaccc agatgcacac caggcggctg gtgcggagca agaccgtgca ccccatctac   1380
```

-continued

```
ctgggcagcc tgcactacga catcagcttc agcgacctga gaggcaacgc cagaggatc    1440 gtgtacgacg acgagctgca gatgcacatc ctgaggggcc ccatccactt ccagagaagg    1500
gccatcctgg gcgccctgaa gttcggctgc aaggtgctgg gcgacaggct ggacgtgccc    1560
ctgttcctga ggaacgcctg a                                              1581
```

<210> SEQ ID NO 9
<211> LENGTH: 1581
<212> TYPE: DNA
<213> ORGANISM: artificial sequence
<220> FEATURE:
<223> OTHER INFORMATION: BTV VP5 codon-optimzied for duckweed expression

<400> SEQUENCE: 9

```
atggggaagg tgatccgctc cctctcccgc ttcggcaaga aggtcggcaa cgccctcacg     60
tccaacaccg ccaagaagat ctactcgacg atcggcaagg ccgcggagcg cttcgccgag    120
agcgagatcg ggtccgccgc gatcgacggg ctcgtccagg gcagcgtcca ctcgatcatc    180
acgggcgagt cctacggcga gtcggtcaag caggccgtgc tgctcaacgt cctggggtcc    240
ggcgaggaga tcccggaccc tctctcgccg ggcgagaggg gcatccaggc gaagctcaag    300
gaactcgagg acgagcagag aaatgagctg gtgcgcctga agtacaacga caagatcaag    360
gagaaattcg ggaaggaact cgaggaagtg tacaacttca tgaacggcga ggccaacgcg    420
gagatcgagg atgagaagca gttcgacatc ctgaacaagg cggtgaccag ctacaacaag    480
atcctcacgg aggaagacct gcaaatgcgc agactcgcca ccgccctgca gaaggagatc    540
ggggagcgga ctcacgccga gaccgtgatg gtgaaggagt atcgcgacaa gatcgacgcg    600
ctgaagaacg ccatcgaggt cgagagggac gggatgcagg aggaggccat ccaggagatc    660
gccgggatga ccgcggacgt gctcgaggcc gcgagcgagg aggtgcccct gatcggcgcc    720
gggatggcca ccgccgtcgc caccgggcgc gctatcgagg gcgcctacaa gctgaagaag    780
gtcatcaacg cgctcagcgg catcgacctc acccacctca gaaccccgaa gatcgagccg    840
tccgtggtct cgaccatcct cgagtaccgg accaaggaga tccccgacaa cgccctggcc    900
gttagcgtcc tgtcgaagaa ccgggccatc caggagaacc acaaggagct gatgcacatc    960
aagaacgaga tcctcccccg gttcaagaag gccatggacg aggagaagga gatctgcggc   1020
atcgaggaca aagtgatcca cccgaaggtc atgatgaagt tcaagatccc ccgcgctcag   1080
cagccccaga tccacgtcta ctccgcgccc tgggactccg acgacgtctt cttcttccac   1140
tgcatctccc accaccacgc caacgagtcc ttcttcctcg gcttcgacct gtccatcgac   1200
ctggtccact acgaggacct caccgcgcac tggcacgctc tgggtgccgc gcaggccgct   1260
gccgggcgga ccctcaccga ggcctaccgc gagttcctca acctggccat cagcaacgcg   1320
ttcggcacgc agatgcacac gcggcgcctg gtgaggagca aaacggtgca cccgatctac   1380
ctgggcagcc tccactacga catcagcttc tccgacctgc gcgggaacgc ccagcggatc   1440
gtgtacgacg acgagctgca gatgcacatc ctccgcggcc ccatccactt ccagcgccgc   1500
gccatcctcg ggccctcaa gttcgggtgc aaggtgctcg gtgaccgcct cgacgtgccc    1560
ctgttcctcc gcaacgccta a                                             1581
```

<210> SEQ ID NO 10
<211> LENGTH: 526
<212> TYPE: PRT
<213> ORGANISM: artificial sequence
<220> FEATURE:

<223> OTHER INFORMATION: BTV VP5 protein

<400> SEQUENCE: 10

```
Met Gly Lys Val Ile Arg Ser Leu Ser Arg Phe Gly Lys Lys Val Gly
 1               5                  10                  15

Asn Ala Leu Thr Ser Asn Thr Ala Lys Lys Ile Tyr Ser Thr Ile Gly
             20                  25                  30

Lys Ala Ala Glu Arg Phe Ala Glu Ser Glu Ile Gly Ser Ala Ala Ile
         35                  40                  45

Asp Gly Leu Val Gln Gly Ser Val His Ser Ile Ile Thr Gly Glu Ser
     50                  55                  60

Tyr Gly Glu Ser Val Lys Gln Ala Val Leu Leu Asn Val Leu Gly Ser
 65                  70                  75                  80

Gly Glu Glu Ile Pro Asp Pro Leu Ser Pro Gly Glu Arg Gly Ile Gln
                 85                  90                  95

Ala Lys Leu Lys Glu Leu Glu Asp Glu Gln Arg Asn Glu Leu Val Arg
            100                 105                 110

Leu Lys Tyr Asn Asp Lys Ile Lys Glu Lys Phe Gly Lys Glu Leu Glu
        115                 120                 125

Glu Val Tyr Asn Phe Met Asn Gly Glu Ala Asn Ala Glu Ile Glu Asp
    130                 135                 140

Glu Lys Gln Phe Asp Ile Leu Asn Lys Ala Val Thr Ser Tyr Asn Lys
145                 150                 155                 160

Ile Leu Thr Glu Glu Asp Leu Gln Met Arg Arg Leu Ala Thr Ala Leu
                165                 170                 175

Gln Lys Glu Ile Gly Glu Arg Thr His Ala Glu Thr Val Met Val Lys
            180                 185                 190

Glu Tyr Arg Asp Lys Ile Asp Ala Leu Lys Asn Ala Ile Glu Val Glu
        195                 200                 205

Arg Asp Gly Met Gln Glu Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
            260                 265                 270

Leu Arg Thr Pro Lys Ile Glu Pro Ser Val Val Ser Thr Ile Leu Glu
        275                 280                 285

Tyr Arg Thr Lys Glu Ile Pro Asp Asn Ala Leu Ala Val Ser Val Leu
    290                 295                 300

Ser Lys Asn Arg Ala Ile Gln Glu Asn His Lys Glu Leu Met His Ile
305                 310                 315                 320

Lys Asn Glu Ile Leu Pro Arg Phe Lys Lys Ala Met Asp Glu Glu Lys
                325                 330                 335

Glu Ile Cys Gly Ile Glu Asp Lys Val Ile His Pro Lys Val Met Met
            340                 345                 350

Lys Phe Lys Ile Pro Arg Ala Gln Gln Pro Gln Ile His Val Tyr Ser
        355                 360                 365

Ala Pro Trp Asp Ser Asp Val Phe Phe Phe His Cys Ile Ser His
    370                 375                 380

His His Ala Asn Glu Ser Phe Phe Leu Gly Phe Asp Leu Ser Ile Asp
385                 390                 395                 400
```

-continued

```
Leu Val His Tyr Glu Asp Leu Thr Ala His Trp His Ala Leu Gly Ala
                405                 410                 415

Ala Gln Ala Ala Ala Gly Arg Thr Leu Thr Glu Ala Tyr Arg Glu Phe
            420                 425                 430

Leu Asn Leu Ala Ile Ser Asn Ala Phe Gly Thr Gln Met His Thr Arg
        435                 440                 445

Arg Leu Val Arg Ser Lys Thr Val His Pro Ile Tyr Leu Gly Ser Leu
    450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 11
<211> LENGTH: 961
<212> TYPE: PRT
<213> ORGANISM: artificial sequence
<220> FEATURE:
<223> OTHER INFORMATION: BTV VP2 protein ACB05467

<400> SEQUENCE: 11

Met Asp Glu Leu Gly Ile Pro Val Tyr Lys Arg Gly Phe Pro Glu His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
    210                 215                 220

Thr Met Asn His Asn Ser Tyr Asp Lys Met Val Glu Gly Leu Ala His
225                 230                 235                 240
```

```
Leu Val Ile Arg Gly Lys Ile Pro Glu Val Ile Arg Asp Asp Ile Ala
            245                 250                 255
Ser Leu Asp Glu Ile Cys Asn Arg Trp Ile Gln Ser Arg His Asp Pro
        260                 265                 270
Gly Glu Ile Lys Ala Tyr Glu Leu Cys Lys Ile Leu Ser Thr Ile Gly
    275                 280                 285
Arg Lys Val Leu Asp Arg Glu Lys Glu Pro Glu Asp Glu Ala Ser Leu
290                 295                 300
Ser Ile Arg Phe Gln Glu Ala Ile Asp Asn Lys Phe Arg Gln His Asp
305                 310                 315                 320
Pro Glu Arg Leu Lys Ile Phe Glu His Arg Asn Gln Arg Arg Asp Glu
                325                 330                 335
Asp Arg Phe Tyr Ile Leu Leu Met Ile Ala Ala Ser Asp Thr Phe Asn
            340                 345                 350
Thr Arg Val Trp Trp Ser Asn Pro Tyr Pro Cys Leu Arg Gly Thr Leu
        355                 360                 365
Ile Ala Ser Glu Thr Lys Leu Gly Asp Val Tyr Ser Met Met Arg Ser
    370                 375                 380
Trp Tyr Asp Trp Ser Val Arg Pro Thr Tyr Thr Pro Tyr Glu Lys Thr
385                 390                 395                 400
Arg Glu Gln Glu Lys Tyr Ile Tyr Gly Arg Val Asn Leu Phe Asp Phe
                405                 410                 415
Val Ala Glu Pro Gly Ile Lys Ile Val His Trp Glu Tyr Arg Leu Asn
            420                 425                 430
His Ser Thr Arg Glu Ile Thr Tyr Ala Gln Gly Asn Pro Cys Asp Leu
        435                 440                 445
Tyr Pro Glu Asp Asp Val Ile Val Thr Lys Phe Asp Asp Val Ala
    450                 455                 460
Tyr Gly Gln Met Ile Asn Glu Met Ile Asn Gly Trp Asn Gln Glu
465                 470                 475                 480
Gln Phe Lys Met His Lys Ile Leu Lys Ser Glu Gly Asn Val Leu Thr
                485                 490                 495
Ile Asp Phe Glu Lys Asp Ala Lys Leu Thr Thr Asn Glu Gly Val Thr
            500                 505                 510
Met Pro Glu Tyr Phe Asn Lys Trp Ile Ile Ala Pro Met Phe Asn Ala
        515                 520                 525
Lys Leu Arg Ile Lys His Glu Glu Ile Ala Gln Arg Gln Ser Asp Asp
    530                 535                 540
Pro Met Val Lys Arg Thr Leu Ser Pro Ile Thr Ala Asp Pro Ile Glu
545                 550                 555                 560
Leu Gln Arg Leu Thr Leu Ala Arg Phe Tyr Asp Ile Arg Pro Ala Leu
                565                 570                 575
Arg Gly Gln Ala Leu Ser Arg Gln Gln Ala Gln Ser Thr Tyr Asp Glu
            580                 585                 590
Glu Ile Ser Lys Arg Gln Asp Tyr Ala Glu Ile Leu Lys Arg Arg Gly
        595                 600                 605
Ile Val Gln Ile Pro Lys Lys Pro Cys Pro Thr Val Thr Ala Gln Tyr
    610                 615                 620
Thr Leu Glu Arg Tyr Ala Leu Phe Ile Ile Asn Ile Leu Gln Gln His
625                 630                 635                 640
Val Val Arg Asp Cys Asp Glu Glu Ala Val Tyr Glu His Pro Lys Ala
                645                 650                 655
Asp His Glu Leu Glu Ile Phe Gly Glu Ser Ile Val Asp Ile Ser Gln
```

-continued

```
                660                 665                 670
Val Ile Ile Leu Ala Phe Asp Leu Ile Phe Glu Arg Arg Arg Val
            675                 680                 685
Arg Asp Val Tyr Glu Ser Arg His Ile Ile Ala Arg Ile Arg Met
        690                 695                 700
Arg Gly Lys Glu Arg Leu Asn Val Ile Ala Glu Phe Phe Pro Thr Tyr
705                 710                 715                 720
Gly Gly Leu Leu Asn Gly Leu Asn Ser Ala Thr Val Val Gln Asp Ile
                725                 730                 735
Met Tyr Leu Asn Phe Leu Pro Leu Tyr Phe Leu Val Gly Asp Asn Met
            740                 745                 750
Ile Tyr Ser His Arg Gln Trp Ser Ile Pro Leu Leu Leu Tyr Thr His
        755                 760                 765
Glu Val Met Val Val Pro Leu Glu Val Gly Ser Tyr Asn Asp Arg Cys
    770                 775                 780
Gly Leu Ile Ala Tyr Leu Glu Tyr Met Val Phe Phe Pro Ser Lys Ala
785                 790                 795                 800
Ile Arg Phe Ser Lys Leu Asn Glu Ala Gln Pro Lys Ile Ala Arg Glu
                805                 810                 815
Met Leu Lys Tyr Tyr Ala Asn Thr Thr Val Tyr Asp Gly Gly Val Asn
            820                 825                 830
Tyr Asn Val Val Thr Thr Lys Gln Leu Leu Tyr Glu Thr Tyr Leu Ala
        835                 840                 845
Ser Leu Cys Gly Gly Ile Ser Asp Gly Ile Val Trp Tyr Leu Pro Ile
    850                 855                 860
Thr His Pro Asn Lys Cys Ile Val Ala Ile Glu Val Ser Asp Glu Arg
865                 870                 875                 880
Val Pro Ala Ser Ile Arg Ala Gly Arg Ile Arg Leu Arg Phe Pro Leu
                885                 890                 895
Ser Ala Arg His Leu Lys Gly Val Val Ile Gln Ile Asp Glu Glu
            900                 905                 910
Gly Glu Phe Thr Val Tyr Ser Glu Gly Ile Val Ser His Arg Val Cys
        915                 920                 925
Lys Lys Asn Leu Leu Lys Tyr Met Cys Asp Ile Ile Leu Leu Lys Phe
    930                 935                 940
Ser Gly His Val Phe Gly Asn Asp Glu Met Leu Thr Lys Leu Leu Asn
945                 950                 955                 960
Val

<210> SEQ ID NO 12
<211> LENGTH: 961
<212> TYPE: PRT
<213> ORGANISM: artificial sequence
<220> FEATURE:
<223> OTHER INFORMATION: BTV VP2 protein ACF37215

<400> SEQUENCE: 12

Met Asp Glu Leu Gly Ile Pro Val Tyr Lys Arg Gly Phe Pro Glu His
1               5                   10                  15
Leu Leu Arg Gly Tyr Glu Phe Ile Ile Asp Val Gly Thr Lys Ile Glu
            20                  25                  30
Ser Val Gly Gly Arg His Asp Val Thr Lys Ile Pro Glu Met Asn Ala
        35                  40                  45
Tyr Asp Ile Lys Gln Glu Ser Ile Arg Thr Ala Leu Trp Tyr Asn Pro
    50                  55                  60
```

```
Ile Arg Asn Asp Gly Phe Val Leu Pro Arg Val Leu Asp Ile Thr Leu
 65                  70                  75                  80

Arg Gly Tyr Asp Glu Arg Arg Ala Val Val Glu Ser Thr Arg His Lys
                 85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
210                 215                 220

Thr Met Asn His Asn Ser Tyr Asp Lys Met Val Glu Gly Leu Ala His
225                 230                 235                 240

Leu Val Ile Arg Gly Lys Ile Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270

Gly Glu Ile Lys Ala Tyr Glu Leu Cys Lys Ile Leu Ser Thr Ile Gly
        275                 280                 285

Arg Lys Val Leu Asp Arg Glu Lys Glu Pro Glu Asp Glu Ala Ser Leu
290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Arg Asp Glu
                325                 330                 335

Asp Arg Phe Tyr Ile Leu Leu Met Ile Ala Ala Ser Asp Thr Phe Asn
            340                 345                 350

Thr Arg Val Trp Trp Ser Asn Pro Tyr Pro Cys Leu Arg Gly Thr Leu
        355                 360                 365

Ile Ala Ser Glu Thr Lys Leu Gly Asp Val Tyr Ser Met Met Arg Ser
370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                405                 410                 415

Val Ala Glu Pro Gly Ile Lys Ile Val His Trp Glu Tyr Arg Leu Asn
            420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Ala Ala
450                 455                 460

Tyr Gly Gln Met Ile Asn Glu Met Ile Asn Gly Gly Trp Asn Gln Glu
465                 470                 475                 480
```

```
Gln Phe Lys Met His Lys Ile Leu Lys Ser Glu Gly Asn Val Leu Thr
                485                 490                 495
Ile Asp Phe Glu Lys Asp Ala Lys Leu Thr Thr Asn Glu Gly Val Thr
            500                 505                 510
Met Pro Glu Tyr Phe Asn Lys Trp Ile Ile Ala Pro Met Phe Asn Ala
        515                 520                 525
Lys Leu Arg Ile Lys His Glu Glu Ile Ala Gln Arg Gln Ser Asp Asp
    530                 535                 540
Pro Met Val Lys Arg Thr Leu Ser Pro Ile Thr Ala Asp Pro Ile Glu
545                 550                 555                 560
Leu Gln Arg Leu Thr Leu Ala Arg Phe Tyr Asp Ile Arg Pro Ala Leu
                565                 570                 575
Arg Gly Gln Ala Leu Ser Arg Gln Gln Ala Gln Ser Thr Tyr Asp Glu
            580                 585                 590
Glu Ile Ser Lys Arg Gln Asp Tyr Ala Glu Ile Leu Lys Arg Arg Gly
        595                 600                 605
Ile Val Gln Ile Pro Lys Lys Pro Cys Pro Thr Val Thr Ala Gln Tyr
    610                 615                 620
Thr Leu Glu Arg Tyr Ala Leu Phe Ile Ile Asn Ile Leu Gln Gln His
625                 630                 635                 640
Val Val Arg Asp Cys Asp Glu Glu Ala Val Tyr Glu His Pro Lys Ala
                645                 650                 655
Asp His Glu Leu Glu Ile Phe Gly Glu Ser Ile Val Asp Ile Ser Gln
            660                 665                 670
Val Ile Ile Leu Ala Phe Asp Leu Ile Phe Glu Arg Arg Arg Arg Val
        675                 680                 685
Arg Asp Val Tyr Glu Ser Arg His Ile Ile Ala Arg Ile Arg Arg Met
    690                 695                 700
Arg Gly Lys Glu Arg Leu Asn Val Ile Ala Glu Phe Phe Pro Thr Tyr
705                 710                 715                 720
Gly Gly Leu Leu Asn Gly Leu Asn Ser Ala Thr Val Val Gln Asp Ile
                725                 730                 735
Met Tyr Leu Asn Phe Leu Pro Leu Tyr Phe Leu Val Gly Asp Asn Met
            740                 745                 750
Ile Tyr Ser His Arg Gln Trp Ser Ile Pro Leu Leu Leu Tyr Thr His
        755                 760                 765
Glu Val Met Val Val Pro Leu Glu Val Gly Ser Tyr Asn Asp Arg Cys
    770                 775                 780
Gly Leu Ile Ala Tyr Leu Glu Tyr Met Val Phe Phe Pro Ser Lys Ala
785                 790                 795                 800
Ile Arg Phe Ser Lys Leu Asn Glu Ala Gln Pro Lys Ile Ala Arg Glu
                805                 810                 815
Met Leu Lys Tyr Tyr Ala Asn Thr Thr Val Tyr Asp Gly Gly Val Asn
            820                 825                 830
Tyr Asn Val Val Thr Thr Lys Gln Leu Leu Tyr Glu Thr Tyr Leu Ala
        835                 840                 845
Ser Leu Cys Gly Gly Ile Ser Asp Gly Ile Val Trp Tyr Leu Pro Ile
    850                 855                 860
Thr His Pro Asn Lys Cys Ile Val Ala Ile Glu Val Ser Asp Glu Arg
865                 870                 875                 880
Val Pro Ala Ser Ile Arg Ala Gly Arg Ile Arg Leu Arg Phe Pro Leu
                885                 890                 895
Ser Ala Arg His Leu Lys Gly Val Val Ile Ile Gln Ile Asp Glu Glu
```

```
                900             905             910
Gly Glu Phe Thr Val Tyr Ser Glu Gly Ile Val Ser His Arg Val Cys
            915             920             925

Lys Lys Asn Leu Leu Lys Tyr Met Cys Asp Ile Ile Leu Leu Lys Phe
        930             935             940

Ser Gly His Val Phe Gly Asn Asp Glu Met Leu Thr Lys Leu Leu Asn
945             950             955             960

Val

<210> SEQ ID NO 13
<211> LENGTH: 961
<212> TYPE: PRT
<213> ORGANISM: artificial sequence
<220> FEATURE:
<223> OTHER INFORMATION: BTV VP2 with ACF37216

<400> SEQUENCE: 13

Met Asp Glu Leu Gly Ile Pro Val Tyr Lys Arg Gly Phe Pro Val His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
    210                 215                 220

Thr Met Asn His Asn Ser Tyr Asp Lys Met Val Glu Gly Leu Ala His
225                 230                 235                 240

Leu Val Ile Arg Gly Lys Ile Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270

Gly Glu Ile Lys Ala Tyr Glu Leu Cys Lys Ile Leu Ser Thr Ile Gly
        275                 280                 285

Arg Lys Val Leu Asp Arg Glu Lys Glu Pro Glu Asp Glu Ala Ser Leu
    290                 295                 300
```

```
Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Arg Asp Glu
            325                 330                 335

Asp Arg Phe Tyr Ile Leu Leu Met Ile Ala Ala Ser Thr Phe Asn
        340                 345                 350

Thr Arg Val Trp Trp Ser Asn Pro Tyr Pro Cys Leu Arg Gly Thr Leu
            355                 360                 365

Ile Ala Ser Glu Thr Lys Leu Gly Asp Val Tyr Ser Met Met Arg Ser
    370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                405                 410                 415

Val Ala Glu Pro Gly Ile Lys Ile Val His Trp Glu Tyr Arg Leu Asn
                420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Ala Ala
    450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Ser Glu Gly Asn Val Leu Thr
                485                 490                 495

Ile Asp Phe Glu Lys Asp Ala Lys Leu Thr Thr Asn Glu Gly Val Thr
                500                 505                 510

Met Pro Glu Tyr Phe Asn Lys Trp Ile Ile Ala Pro Met Phe Asn Ala
            515                 520                 525

Lys Leu Arg Ile Lys His Glu Glu Ile Ala Gln Arg Gln Ser Asp Asp
    530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                565                 570                 575

Arg Gly Gln Ala Leu Ser Arg Gln Gln Ala Gln Ser Thr Tyr Asp Glu
            580                 585                 590

Glu Ile Ser Lys Arg Gln Asp Tyr Ala Glu Ile Leu Lys Arg Arg Gly
        595                 600                 605

Ile Val Gln Ile Pro Lys Lys Pro Cys Pro Thr Val Thr Ala Gln Tyr
    610                 615                 620

Thr Leu Glu Arg Tyr Ala Leu Phe Ile Ile Asn Ile Leu Gln Gln His
625                 630                 635                 640

Val Val Arg Asp Cys Asp Glu Glu Ala Val Tyr Glu His Pro Lys Ala
                645                 650                 655

Asp His Glu Leu Glu Ile Phe Gly Glu Ser Ile Val Asp Ile Ser Gln
            660                 665                 670

Val Ile Ile Leu Ala Phe Asp Leu Ile Phe Glu Arg Arg Arg Val
    675                 680                 685

Arg Asp Val Tyr Glu Ser Arg His Ile Ile Ala Arg Ile Arg Arg Met
        690                 695                 700

Arg Gly Lys Glu Arg Leu Asn Val Ile Ala Glu Phe Phe Pro Thr Tyr
705                 710                 715                 720
```

```
Gly Gly Leu Leu Asn Gly Leu Asn Ser Ala Thr Val Val Gln Asp Ile
                725                 730                 735

Met Tyr Leu Asn Phe Leu Pro Leu Tyr Phe Leu Val Gly Asp Asn Met
            740                 745                 750

Ile Tyr Ser His Arg Gln Trp Ser Ile Pro Leu Leu Leu Tyr Thr His
        755                 760                 765

Glu Val Met Val Val Pro Leu Glu Val Gly Ser Tyr Asn Asp Arg Cys
    770                 775                 780

Gly Leu Ile Ala Tyr Leu Glu Tyr Met Val Phe Phe Pro Ser Lys Ala
785                 790                 795                 800

Ile Arg Ser Ser Lys Leu Asn Glu Ala Gln Pro Lys Ile Ala Arg Glu
                805                 810                 815

Met Leu Lys Tyr Tyr Ala Asn Thr Thr Val Tyr Asp Gly Gly Val Asn
            820                 825                 830

Tyr Asn Val Val Thr Thr Lys Gln Leu Leu Tyr Glu Thr Tyr Leu Ala
        835                 840                 845

Ser Leu Cys Gly Gly Ile Ser Asp Gly Ile Val Trp Tyr Leu Pro Ile
    850                 855                 860

Thr His Pro Asn Lys Cys Ile Val Ala Ile Glu Val Ser Asp Glu Arg
865                 870                 875                 880

Val Pro Ala Ser Ile Arg Ala Gly Arg Ile Arg Leu Arg Phe Pro Leu
                885                 890                 895

Ser Ala Arg His Leu Lys Gly Val Val Ile Ile Gln Ile Asp Glu Glu
            900                 905                 910

Gly Glu Phe Thr Val Tyr Ser Glu Gly Ile Val Ser His Arg Val Cys
        915                 920                 925

Lys Lys Asn Leu Leu Lys Tyr Met Cys Asp Ile Ile Leu Leu Lys Phe
    930                 935                 940

Ser Gly His Val Phe Gly Asn Asp Glu Met Leu Thr Lys Leu Leu Asn
945                 950                 955                 960

Val

<210> SEQ ID NO 14
<211> LENGTH: 961
<212> TYPE: PRT
<213> ORGANISM: artificial sequence
<220> FEATURE:
<223> OTHER INFORMATION: BTV VP2 with ACJ65032

<400> SEQUENCE: 14

Met Asp Glu Leu Gly Ile Pro Val Tyr Lys Arg Gly Phe Pro Glu His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
```

-continued

```
            115                 120                 125
Val Ala His Ser Leu His Asn Cys Val Val Lys Ile Asp Ser Lys Lys
130                 135                 140
Ala Asp Thr Met Ser Tyr His Val Glu Pro Ile Glu Asp Ala Ser Lys
145                 150                 155                 160
Gly Cys Leu His Thr Arg Thr Met Met Trp Asn His Leu Val Arg Ile
                    165                 170                 175
Glu Thr Phe His Ala Ala Gln Glu Val Ala Tyr Thr Leu Lys Pro Thr
                180                 185                 190
Tyr Asp Ile Val Val His Ala Glu Arg Arg Asp Arg Ser Gln Pro Phe
            195                 200                 205
Arg Pro Gly Asp Gln Thr Leu Ile Asn Phe Gly Arg Gly Gln Lys Val
210                 215                 220
Thr Met Asn His Asn Ser Tyr Asp Lys Met Val Glu Gly Leu Ala His
225                 230                 235                 240
Leu Val Ile Arg Gly Lys Ile Pro Glu Val Ile Arg Asp Asp Ile Ala
                    245                 250                 255
Ser Leu Asp Glu Ile Cys Asn Arg Trp Ile Gln Ser Arg His Asp Pro
                260                 265                 270
Gly Glu Ile Lys Ala Tyr Glu Leu Cys Lys Ile Leu Ser Thr Ile Gly
            275                 280                 285
Arg Lys Val Leu Asp Arg Glu Lys Glu Pro Glu Asp Glu Ala Ser Leu
290                 295                 300
Ser Ile Arg Phe Gln Glu Ala Ile Asp Asn Lys Phe Arg Gln His Asp
305                 310                 315                 320
Pro Glu Arg Leu Lys Ile Phe Glu His Arg Asn Gln Arg Arg Asp Glu
                    325                 330                 335
Asp Arg Phe Tyr Ile Leu Leu Met Ile Ala Ala Ser Asp Thr Phe Asn
                340                 345                 350
Thr Arg Val Trp Trp Ser Asn Pro Tyr Pro Cys Leu Arg Gly Thr Leu
            355                 360                 365
Ile Ala Ser Glu Thr Lys Leu Gly Asp Val Tyr Ser Met Met Arg Ser
370                 375                 380
Trp Tyr Asp Trp Ser Val Arg Pro Thr Tyr Thr Pro Tyr Glu Lys Thr
385                 390                 395                 400
Arg Glu Gln Glu Lys Tyr Ile Tyr Gly Arg Val Asn Leu Phe Asp Phe
                    405                 410                 415
Val Ala Glu Pro Gly Ile Lys Ile Val His Trp Glu Tyr Arg Leu Asn
                420                 425                 430
His Ser Thr Arg Glu Ile Thr Tyr Ala Gln Gly Asn Pro Cys Asp Leu
            435                 440                 445
Tyr Pro Glu Asp Asp Val Ile Val Thr Lys Phe Asp Asp Val Ala
450                 455                 460
Tyr Gly Gln Met Ile Asn Glu Met Ile Asn Gly Gly Trp Asn Gln Glu
465                 470                 475                 480
Gln Phe Lys Met His Lys Ile Leu Lys Ser Glu Gly Asn Val Leu Thr
                    485                 490                 495
Ile Asp Phe Glu Lys Asp Ala Lys Leu Thr Thr Asn Glu Gly Val Thr
                500                 505                 510
Met Pro Glu Tyr Phe Asn Lys Trp Ile Ile Ala Pro Met Phe Asn Ala
            515                 520                 525
Lys Leu Arg Ile Lys His Glu Glu Ile Ala Gln Arg Gln Ser Asp Asp
530                 535                 540
```

-continued

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
            565                 570                 575

Arg Gly Gln Ala Leu Ser Arg Gln Gln Ala Gln Ser Thr Tyr Asp Glu
        580                 585                 590

Glu Ile Ser Lys Arg Gln Asp Tyr Ala Glu Ile Leu Lys Arg Arg Gly
    595                 600                 605

Ile Val Gln Ile Pro Lys Lys Pro Cys Pro Thr Val Thr Ala Gln Tyr
610                 615                 620

Thr Leu Glu Arg Tyr Ala Leu Phe Ile Ile Ser Ile Leu Gln Gln His
625                 630                 635                 640

Val Val Arg Asp Cys Asp Glu Glu Ala Val Tyr Glu His Pro Lys Ala
            645                 650                 655

Asp His Glu Leu Glu Ile Phe Gly Glu Ser Ile Val Asp Ile Ser Gln
        660                 665                 670

Val Ile Ile Leu Ala Phe Asp Leu Ile Phe Glu Arg Arg Arg Arg Val
    675                 680                 685

Arg Asp Val Tyr Glu Ser Arg His Ile Ile Ala Arg Ile Arg Arg Met
690                 695                 700

Arg Gly Lys Glu Arg Leu Asn Val Ile Ala Glu Phe Phe Pro Thr Tyr
705                 710                 715                 720

Gly Gly Leu Leu Asn Gly Leu Asn Ser Ala Thr Val Val Gln Asn Ile
            725                 730                 735

Met Tyr Leu Asn Phe Leu Pro Leu Tyr Phe Leu Val Gly Asp Asn Met
        740                 745                 750

Ile Tyr Ser His Arg Gln Trp Ser Ile Pro Leu Leu Leu Tyr Thr His
    755                 760                 765

Glu Val Met Val Val Pro Leu Glu Val Gly Ser Tyr Asn Asp Arg Cys
770                 775                 780

Gly Leu Ile Ala Tyr Leu Glu Tyr Met Val Phe Phe Pro Ser Lys Ala
785                 790                 795                 800

Ile Arg Phe Ser Lys Leu Asn Glu Ala Gln Pro Lys Ile Ala Arg Glu
            805                 810                 815

Met Leu Lys Tyr Tyr Ala Asn Thr Thr Val Tyr Asp Gly Gly Val Asn
        820                 825                 830

Tyr Asn Val Val Thr Thr Lys Gln Leu Leu Tyr Glu Thr Tyr Leu Ala
    835                 840                 845

Ser Leu Cys Gly Gly Ile Ser Asp Gly Ile Val Trp Tyr Leu Pro Ile
850                 855                 860

Thr His Pro Asn Lys Cys Ile Val Ala Ile Glu Val Ser Asp Glu Arg
865                 870                 875                 880

Val Pro Ala Ser Ile Arg Ala Gly Arg Ile Arg Leu Arg Phe Pro Leu
            885                 890                 895

Ser Ala Arg His Leu Lys Gly Val Val Ile Ile Gln Ile Asp Glu Glu
        900                 905                 910

Gly Glu Phe Thr Val Tyr Ser Glu Gly Ile Val Ser His Arg Val Cys
    915                 920                 925

Lys Lys Asn Leu Leu Lys Tyr Met Cys Asp Ile Ile Leu Leu Lys Phe
930                 935                 940

Ser Gly His Val Phe Gly Asn Asp Glu Met Leu Thr Lys Leu Leu Asn
945                 950                 955                 960

Val

<210> SEQ ID NO 15
<211> LENGTH: 961
<212> TYPE: PRT
<213> ORGANISM: artificial sequence
<220> FEATURE:
<223> OTHER INFORMATION: BTV VP2 with ACR58459

<400> SEQUENCE: 15

```
Met Asp Glu Leu Gly Ile Pro Val Tyr Lys Arg Gly Phe Pro Glu His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Phe Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
            180                 185                 190

Tyr Asp Ile Val Val His Ala Glu Arg Arg Asp Arg Ser Gln Pro Phe
        195                 200                 205

Arg Pro Gly Asp Gln Thr Leu Ile Asn Phe Gly Arg Gly Gln Lys Val
    210                 215                 220

Ala Met Asn His Asn Ser Tyr Asp Lys Met Val Glu Gly Leu Thr His
225                 230                 235                 240

Leu Val Ile Arg Gly Lys Thr Pro Glu Val Ile Arg Asp Ile Ala
                245                 250                 255

Ser Leu Asp Glu Ile Cys Asn Arg Trp Ile Gln Ser Arg His Asp Pro
            260                 265                 270

Gly Glu Ile Lys Ala Tyr Glu Leu Cys Lys Ile Leu Ser Thr Ile Gly
        275                 280                 285

Arg Lys Val Leu Asp Arg Glu Lys Glu Pro Glu Asp Glu Ala Asn Leu
    290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Asp Glu
                325                 330                 335

Asp Arg Phe Tyr Ile Leu Leu Met Ile Ala Ala Ser Asp Thr Phe Asn
            340                 345                 350

Thr Arg Val Trp Trp Ser Asn Pro Tyr Pro Cys Leu Arg Gly Thr Leu
```

```
                355                 360                 365
Ile Ala Ser Glu Thr Lys Leu Gly Asp Val Tyr Ser Met Met Arg Ser
370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                405                 410                 415

Val Ala Glu Pro Gly Ile Lys Ile Val His Trp Glu Tyr Arg Leu Asn
                420                 425                 430

His Ser Thr Arg Glu Ile Thr Tyr Ala Gln Gly Asn Pro Cys Asp Leu
                435                 440                 445

Tyr Pro Glu Asp Asp Val Ile Val Thr Lys Phe Asp Asp Val Ala
                450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Ser Glu Gly Asn Val Leu Thr
                485                 490                 495

Ile Asp Phe Glu Lys Asp Ala Lys Leu Thr Thr Asn Glu Gly Val Thr
                500                 505                 510

Met Pro Glu Tyr Phe Asn Lys Trp Ile Ile Ala Pro Met Phe Asn Ala
                515                 520                 525

Lys Leu Arg Ile Lys His Glu Glu Ile Ala Gln Arg Gln Ser Asp Asp
530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                565                 570                 575

Arg Gly Gln Ala Leu Ser Arg Gln Gln Ala Gln Ser Thr Tyr Asp Glu
                580                 585                 590

Glu Ile Ser Lys Gln Arg Asp Tyr Ala Glu Ile Leu Lys Arg Arg Gly
                595                 600                 605

Ile Val Gln Ile Pro Lys Lys Pro Cys Pro Thr Val Thr Ala Gln Tyr
                610                 615                 620

Thr Leu Glu Arg Tyr Ala Leu Phe Ile Ile Asn Ile Leu Gln Gln His
625                 630                 635                 640

Val Ala Arg Asp Cys Asp Glu Glu Ala Ile Tyr Glu His Pro Lys Ala
                645                 650                 655

Asp Tyr Glu Leu Glu Ile Phe Gly Glu Ser Ile Val Asp Ile Ser Gln
                660                 665                 670

Val Ile Val Leu Val Phe Asp Leu Ile Phe Glu Arg Arg Arg Arg Val
                675                 680                 685

Arg Asp Val Tyr Glu Ser Arg Tyr Ile Ile Ala Arg Ile Arg Arg Met
                690                 695                 700

Arg Gly Lys Glu Arg Leu Asn Val Ile Ala Glu Phe Phe Pro Thr Tyr
705                 710                 715                 720

Gly Ser Leu Leu Asn Gly Leu Asn Ser Ala Thr Val Val Gln Asp Ile
                725                 730                 735

Met Tyr Leu Asn Phe Leu Pro Tyr Phe Leu Ala Gly Asp Asn Met
                740                 745                 750

Ile Tyr Ser His Arg Gln Trp Ser Ile Pro Leu Leu Leu Tyr Thr His
                755                 760                 765

Glu Val Met Val Val Pro Leu Glu Val Gly Ser Tyr Asn Asp Arg Cys
770                 775                 780
```

```
Gly Leu Ile Ala Tyr Leu Glu Tyr Met Val Phe Phe Pro Ser Lys Ala
785                 790                 795                 800

Ile Arg Leu Ser Lys Leu Asn Glu Ala Gln Pro Lys Ile Ala Arg Glu
            805                 810                 815

Met Leu Lys Tyr Tyr Ala Asn Thr Ala Val Tyr Asp Gly Gly Val Asn
            820                 825                 830

Tyr Asn Val Val Thr Thr Lys Gln Leu Leu Tyr Glu Thr Tyr Leu Ala
            835                 840                 845

Ser Leu Cys Gly Gly Ile Ser Asp Gly Ile Val Trp Tyr Leu Pro Ile
850                 855                 860

Thr His Pro Asn Lys Cys Ile Val Ala Ile Glu Val Ser Asp Glu Arg
865                 870                 875                 880

Val Pro Ala Ser Ile Arg Ala Gly Arg Ile Arg Leu Arg Phe Pro Leu
            885                 890                 895

Ser Ala Arg His Leu Lys Gly Val Val Ile Gln Ile Asp Glu Glu
            900                 905                 910

Gly Glu Phe Thr Val Tyr Ser Glu Gly Ile Val Ser His Arg Val Cys
            915                 920                 925

Lys Lys Asn Leu Leu Lys Tyr Met Cys Asp Ile Ile Leu Leu Lys Phe
930                 935                 940

Ser Gly His Val Phe Gly Asn Asp Glu Met Leu Thr Lys Leu Leu Asn
945                 950                 955                 960

Val

<210> SEQ ID NO 16
<211> LENGTH: 961
<212> TYPE: PRT
<213> ORGANISM: artificial sequence
<220> FEATURE:
<223> OTHER INFORMATION: BTV VP2 with CAA39322

<400> SEQUENCE: 16

Met Asp Glu Leu Gly Ile Pro Val Tyr Lys Arg Gly Phe Pro Glu His
1               5                   10                  15

Leu Leu Arg Gly Tyr Glu Phe Thr Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Ile Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
        115                 120                 125

Val Ala His Ser Leu His Asn Cys Val Val Lys Ile Asp Ser Lys Lys
    130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175
```

```
Glu Thr Phe His Thr Ala Gln Glu Val His Ile Leu Phe Lys Pro Thr
                180                 185                 190

Tyr Asp Ile Val Val His Ala Glu Arg Arg Asp Arg Ser Gln Pro Phe
            195                 200                 205

Arg Pro Gly Asp Gln Thr Leu Ile Asn Phe Gly Arg Gly Gln Lys Val
        210                 215                 220

His Met Asn His Asn Ser Tyr Asp Lys Met Val Glu Gly Leu Thr His
225                 230                 235                 240

Leu Val Met Arg Gly Lys Met Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270

Gly Glu Val Lys Ala Tyr Glu Leu Cys Lys Ile Leu Ser Thr Ile Gly
        275                 280                 285

Arg Lys Val Leu Asp Arg Glu Lys Glu Pro Glu Asp Glu Ala Asn Leu
    290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Gly Asn Gln Arg Arg Asp Glu
                325                 330                 335

Asp Arg Phe Tyr Ile Leu Leu Met Ile Ala Ala Ser Asp Thr Phe Asn
            340                 345                 350

Thr Arg Val Trp Trp Ser Asn Pro Tyr Pro Cys Leu Arg Gly Thr Leu
        355                 360                 365

Ile Ala Ser Glu Thr Lys Leu Gly Asp Val Tyr Ser Met Met Arg Ser
    370                 375                 380

Trp Tyr Asp Trp Ser Val Arg Pro Thr Tyr Thr Pro Tyr Glu Lys Thr
385                 390                 395                 400

Arg Glu Gln Glu Glu Tyr Ile Tyr Gly Arg Val Asn Leu Phe Asp Phe
                405                 410                 415

Val Ala Glu Pro Gly Ile Lys Ile Val His Trp Glu Tyr Arg Leu Asn
            420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Val Ala
    450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Thr Glu Gly Asn Val Leu Thr
                485                 490                 495

Ile Asp Phe Glu Lys Asp Ala Lys Leu Thr Thr Asn Glu Gly Val Thr
            500                 505                 510

Met Pro Glu Tyr Phe Asn Lys Trp Ile Ile Ala Pro Met Phe Asn Ala
        515                 520                 525

Asn Val Arg Ile Lys His Glu Gly Ile Ala Gln Arg Gln Ser Asp Asp
    530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                565                 570                 575

Arg Gly Gln Ala Leu Ser Arg Gln Gln Ala Gln Ser Thr Tyr Asp Glu
            580                 585                 590

Glu Ile Ser Lys Lys Ala Gly Tyr Ala Glu Val Leu Lys Arg Arg Gly
```

```
                 595                 600                 605
Ile Val Gln Ile Pro Lys Lys Pro Cys Pro Thr Val Thr Ala Gln Tyr
610                 615                 620

Thr Leu Glu Arg Tyr Ala Leu Phe Ile Ile Asn Tyr Leu Gln Gln His
625                 630                 635                 640

Val Ala Arg Asp Cys Asp Glu Glu Ala Ile Tyr Glu His Pro Lys Ala
                645                 650                 655

Asp His Glu Leu Glu Ile Phe Gly Ser Ile Val Asp Ile Ser Gln
                660                 665                 670

Val Ile Val Leu Val Phe Asp Leu Ile Phe Glu Arg Arg Arg Val
            675                 680                 685

Arg Asp Val Tyr Glu Ser Arg Tyr Ile Ile Ala Arg Ile Arg Glu Met
        690                 695                 700

Arg Gly Lys Glu Lys Leu Asn Val Ile Ala Glu Phe Phe Pro Thr Tyr
705                 710                 715                 720

Gly Ser Leu Leu Asn Gly Leu Ser Gly Ala Thr Val Val Gln Asp Ile
                725                 730                 735

Met Tyr Leu Asn Phe Leu Pro Leu Tyr Phe Leu Val Gly Asp Asn Met
                740                 745                 750

Ile Tyr Ser His Arg Gln Trp Ser Ile Pro Leu Leu Leu Tyr Thr His
            755                 760                 765

Glu Val Met Val Ile Pro Leu Glu Val Gly Ser Tyr Asn Asp Arg Cys
770                 775                 780

Gly Leu Ile Ala Tyr Leu Glu Tyr Met Val Phe Phe Pro Ser Lys Ala
785                 790                 795                 800

Ile Arg Leu Ser Lys Leu Asn Glu Ala His Ala Lys Ile Ala Arg Glu
                805                 810                 815

Met Leu Lys Tyr Tyr Ala Asn Thr Thr Val Tyr Asp Gly Gly Asp Asn
                820                 825                 830

Ser Asn Val Val Thr Thr Lys Gln Leu Leu Tyr Glu Thr Tyr Leu Ala
            835                 840                 845

Ser Leu Cys Gly Gly Phe Leu Asp Gly Ile Val Trp Tyr Leu Pro Ile
850                 855                 860

Thr His Pro Asn Lys Cys Ile Val Ala Ile Glu Val Ser Asp Glu Arg
865                 870                 875                 880

Val Pro Ala Ser Val Arg Ala Gly Arg Ile Arg Leu Arg Phe Pro Leu
                885                 890                 895

Ser Ala Arg His Leu Lys Gly Val Val Ile Gln Val Asp Leu Gly
                900                 905                 910

Gly Arg Phe Thr Val Tyr Ser Glu Gly Ile Val Ser His Arg Val Cys
            915                 920                 925

Lys Lys Asn Leu Leu Lys Tyr Met Cys Asp Ile Ile Leu Leu Lys Phe
        930                 935                 940

Ser Gly His Val Phe Gly Asn Asp Glu Met Leu Thr Lys Leu Leu Asn
945                 950                 955                 960

Val

<210> SEQ ID NO 17
<211> LENGTH: 961
<212> TYPE: PRT
<213> ORGANISM: artificial sequence
<220> FEATURE:
<223> OTHER INFORMATION: BTV VP2 with CAE51088

<400> SEQUENCE: 17
```

```
Met Asp Glu Leu Gly Ile Pro Val Tyr Lys Arg Gly Phe Pro Glu His
1               5                   10                  15

Leu Leu Arg Gly Tyr Glu Phe Ile Ile Asp Val Gly Thr Lys Ile Glu
            20                  25                  30

Ser Val Gly Gly Arg His Asp Val Thr Lys Ile Pro Glu Met Asn Ala
        35                  40                  45

Tyr Asp Ile Lys Gln Glu Ser Ile Arg Thr Ala Leu Trp Tyr Asn Pro
    50                  55                  60

Ile Arg Asn Asp Gly Ile Val Leu Pro Arg Val Leu Asp Ile Thr Leu
65                  70                  75                  80

Arg Gly Tyr Asp Glu Arg Arg Ala Val Val Glu Ser Thr Arg His Lys
                85                  90                  95

Ser Phe His Thr Asn Asp Gln Trp Val Gln Trp Met Met Lys Asp Ser
            100                 105                 110

Met Asp Ala Gln Pro Leu Lys Val Gly Leu Asp Asp Gln Ser Arg Asn
            115                 120                 125

Val Ala His Ser Leu His Asn Cys Val Val Lys Ile Asp Ser Lys Lys
            130                 135                 140

Ala Asp Thr Met Ser Tyr His Val Glu Pro Ile Glu Asp Ala Ser Lys
145                 150                 155                 160

Gly Cys Leu His Thr Arg Thr Met Met Trp Asn His Leu Val Arg Ile
                165                 170                 175

Glu Thr Phe His Ala Ala Gln Glu Val Ala Tyr Thr Leu Lys Pro Thr
                180                 185                 190

Tyr Asp Ile Val Val His Ala Glu Arg Arg Asp Arg Ser Gln Pro Phe
                195                 200                 205

Arg Pro Gly Asp Gln Thr Leu Ile Asn Phe Gly Arg Gly Gln Lys Val
            210                 215                 220

Ala Met Asn His Asn Ser Tyr Asp Lys Met Val Glu Gly Leu Thr His
225                 230                 235                 240

Leu Val Ile Arg Gly Lys Thr Pro Glu Val Ile Arg Asp Asp Ile Ala
                245                 250                 255

Ser Leu Asp Glu Ile Cys Asn Arg Trp Ile Gln Ser Arg His Asp Pro
            260                 265                 270

Gly Glu Ile Lys Ala Tyr Glu Leu Cys Lys Ile Leu Ser Thr Ile Gly
            275                 280                 285

Arg Lys Val Leu Asp Arg Glu Lys Glu Pro Glu Asp Glu Ala Asn Leu
            290                 295                 300

Ser Ile Arg Phe Gln Glu Ala Ile Asp Asn Lys Phe Arg Gln His Asp
305                 310                 315                 320

Pro Glu Arg Leu Lys Ile Phe Glu His Arg Asn Gln Arg Arg Asp Glu
            325                 330                 335

Asp Arg Phe Tyr Ile Leu Leu Met Ile Ala Ala Ser Asp Thr Phe Asn
            340                 345                 350

Thr Arg Val Trp Trp Ser Asn Pro Tyr Pro Cys Leu Arg Gly Thr Leu
            355                 360                 365

Ile Ala Ser Glu Thr Lys Leu Gly Asp Val Tyr Ser Met Met Arg Ser
            370                 375                 380

Trp Tyr Asp Trp Ser Val Arg Pro Thr Tyr Thr Pro Tyr Glu Lys Thr
385                 390                 395                 400

Arg Glu Gln Glu Lys Tyr Ile Tyr Gly Arg Val Asn Leu Phe Asp Phe
                405                 410                 415
```

```
Val Ala Glu Pro Gly Ile Lys Ile Val His Trp Glu Tyr Arg Leu Asn
            420                 425                 430

His Ser Thr Arg Glu Ile Thr Tyr Ala Gln Gly Asn Pro Cys Asp Leu
        435                 440                 445

Tyr Pro Glu Asp Asp Val Ile Val Thr Lys Phe Asp Asp Val Ala
    450                 455                 460

Tyr Gly Gln Met Ile Asn Glu Met Ile Asn Gly Gly Trp Asn Gln Glu
465                 470                 475                 480

Gln Phe Lys Met His Lys Ile Leu Lys Thr Glu Gly Asn Val Leu Thr
                485                 490                 495

Ile Asp Phe Glu Lys Asp Ala Lys Leu Thr Thr Asn Glu Gly Val Thr
            500                 505                 510

Met Pro Glu Tyr Phe Asn Lys Trp Ile Ile Ala Pro Met Phe Asn Ala
        515                 520                 525

Lys Leu Arg Ile Lys His Glu Glu Ile Ala Gln Arg Gln Ser Asp Asp
    530                 535                 540

Pro Met Val Lys Arg Thr Leu Ser Pro Ile Thr Ala Asp Pro Ile Glu
545                 550                 555                 560

Leu Gln Arg Leu Thr Leu Ala Arg Phe Tyr Asp Ile Arg Pro Ala Leu
                565                 570                 575

Arg Gly Gln Ala Leu Ser Arg Gln Gln Ala Gln Ser Thr Tyr Asp Glu
            580                 585                 590

Glu Ile Ser Lys Lys Ala Gly Tyr Ala Glu Ile Leu Lys Arg Arg Gly
        595                 600                 605

Ile Val Gln Ile Pro Lys Lys Pro Cys Pro Thr Val Thr Ala Gln Tyr
    610                 615                 620

Thr Leu Glu Arg Tyr Ala Leu Phe Ile Ile Asn Tyr Leu Gln Gln His
625                 630                 635                 640

Val Ala Arg Asp Cys Asp Glu Glu Ala Ile Tyr Glu His Pro Lys Ala
                645                 650                 655

Asp Tyr Glu Leu Glu Ile Phe Gly Glu Ser Ile Val Asp Ile Ser Gln
            660                 665                 670

Val Ile Val Leu Val Phe Asp Leu Ile Phe Glu Arg Arg Arg Arg Val
        675                 680                 685

Arg Asp Val Tyr Glu Ser Arg Tyr Ile Ile Ala Arg Ile Arg Arg Met
    690                 695                 700

Arg Gly Lys Glu Arg Leu Asn Val Ile Ala Glu Phe Phe Pro Thr Tyr
705                 710                 715                 720

Gly Ser Leu Leu Asn Gly Leu Asn Ser Ala Thr Val Val Gln Asp Ile
                725                 730                 735

Met Tyr Leu Asn Phe Leu Pro Leu Tyr Phe Leu Ala Gly Asp Asn Met
            740                 745                 750

Ile Tyr Ser His Arg Gln Trp Ser Ile Pro Leu Leu Leu Tyr Thr His
        755                 760                 765

Glu Val Met Val Ile Pro Leu Glu Val Gly Ser Tyr Asn Asp Arg Cys
    770                 775                 780

Gly Leu Ile Ala Tyr Leu Glu Tyr Met Val Phe Phe Pro Ser Lys Ala
785                 790                 795                 800

Ile Arg Leu Ser Lys Leu Asn Glu Ala His Ala Lys Ile Ala Arg Glu
                805                 810                 815

Met Leu Lys Tyr Tyr Ala Asn Thr Thr Val Tyr Asp Gly Gly Asp Asn
            820                 825                 830

Tyr Asn Val Val Thr Thr Lys Gln Leu Leu Tyr Glu Thr Tyr Leu Ala
```

```
                    835                 840                 845
Ser Leu Cys Gly Gly Ile Ser Asp Gly Ile Val Trp Tyr Leu Pro Ile
850                 855                 860

Thr His Pro Asn Lys Cys Ile Val Ala Ile Glu Val Ser Asp Glu Arg
865                 870                 875                 880

Val Pro Ala Ser Ile Arg Ala Gly Arg Ile Arg Leu Arg Phe Pro Leu
                    885                 890                 895

Ser Ala Arg His Leu Lys Gly Val Val Ile Ile Gln Ile Asp Arg Gly
                900                 905                 910

Gly Arg Phe Thr Val Tyr Ser Glu Gly Ile Val Ser His Arg Val Cys
            915                 920                 925

Lys Lys Asn Leu Leu Lys Tyr Met Cys Asp Ile Ile Leu Leu Lys Phe
930                 935                 940

Ser Gly His Val Phe Gly Asn Asp Glu Met Leu Thr Lys Leu Leu Asn
945                 950                 955                 960

Val
```

<210> SEQ ID NO 18
<211> LENGTH: 526
<212> TYPE: PRT
<213> ORGANISM: artificial sequence
<220> FEATURE:
<223> OTHER INFORMATION: BTV VP5 with ACB59233

<400> SEQUENCE: 18

```
Met Gly Lys Val Ile Arg Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
                20                  25                  30

Lys Ala Ala Glu Arg Phe Ala Glu Ser Glu Ile Gly Ser Ala Ala Ile
            35                  40                  45

Asp Gly Leu Val Gln Gly Ser Val His Ser Ile Thr Gly Glu Ser
        50                  55                  60

Tyr Gly Glu Ser Val Lys Gln Ala Val Leu Leu Asn Val Leu Gly Ser
65                  70                  75                  80

Gly Glu Glu Ile Pro Asp Pro Leu Ser Pro Gly Glu Arg Gly Ile Gln
                85                  90                  95

Ala Lys Leu Lys Glu Leu Glu Asp Glu Gln Arg Asn Glu Leu Val Arg
            100                 105                 110

Leu Lys Tyr Asn Asp Lys Ile Lys Glu Lys Phe Gly Lys Glu Leu Glu
        115                 120                 125

Glu Val Tyr Asn Phe Met Asn Gly Glu Ala Asn Ala Glu Ile Glu Asp
    130                 135                 140

Glu Lys Gln Phe Asp Ile Leu Asn Arg Ala Val Thr Ser Tyr Asn Lys
145                 150                 155                 160

Ile Leu Thr Glu Glu Asp Leu Gln Met Arg Arg Leu Ala Thr Ala Leu
                165                 170                 175

Gln Lys Glu Ile Gly Glu Arg Thr His Ala Glu Thr Val Met Val Lys
            180                 185                 190

Glu Tyr Arg Asp Lys Ile Asp Ala Leu Lys Asn Ala Ile Glu Val Glu
        195                 200                 205

Arg Asp Gly Met Gln Glu Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240
```

-continued

```
Gly Met Ala Thr Ala Val Ala Thr Gly Arg Ala Ile Glu Gly Ala Tyr
            245                 250                 255

Lys Leu Lys Lys Val Ile Asn Ala Leu Ser Gly Ile Asp Leu Thr His
        260                 265                 270

Leu Arg Thr Pro Lys Ile Glu Pro Ser Val Val Ser Thr Ile Leu Glu
        275                 280                 285

Tyr Arg Thr Lys Glu Ile Pro Asp Asn Ala Leu Ala Val Ser Val Leu
        290                 295                 300

Ser Lys Asn Arg Ala Ile Gln Glu Asn His Lys Glu Leu Met His Ile
305                 310                 315                 320

Lys Asn Glu Ile Leu Pro Arg Phe Lys Lys Ala Met Asp Glu Glu Lys
                325                 330                 335

Glu Ile Cys Gly Ile Glu Asp Lys Val Ile His Pro Lys Val Met Met
            340                 345                 350

Lys Phe Lys Ile Pro Arg Ala Gln Gln Pro Gln Ile His Val Tyr Ser
        355                 360                 365

Ala Pro Trp Asp Ser Asp Val Phe Phe His Cys Ile Ser His
        370                 375                 380

His His Ala Asn Glu Ser Phe Phe Leu Gly Phe Asp Leu Ser Ile Asp
385                 390                 395                 400

Leu Val His Tyr Glu Asp Leu Thr Ala His Gly His Ala Leu Gly Ala
                405                 410                 415

Ala Gln Ala Ala Ala Gly Arg Thr Leu Thr Glu Ala Tyr Arg Glu Phe
            420                 425                 430

Leu Asn Leu Ala Ile Ser Asn Ala Phe Gly Thr Gln Met His Thr Arg
        435                 440                 445

Arg Leu Val Arg Ser Lys Thr Val His Pro Ile Tyr Leu Gly Ser Leu
    450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525
```

<210> SEQ ID NO 19
<211> LENGTH: 526
<212> TYPE: PRT
<213> ORGANISM: artificial sequence
<220> FEATURE:
<223> OTHER INFORMATION: BTV VP5 with ACB59234

<400> SEQUENCE: 19

```
Met Gly Lys Val Ile Arg Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
            20                  25                  30

Lys Ala Ala Glu Arg Phe Ala Glu Ser Glu Ile Gly Ser Ala Ala Ile
        35                  40                  45

Asp Gly Leu Val Gln Gly Ser Val His Ser Ile Ile Thr Gly Glu Ser
    50                  55                  60

Tyr Gly Glu Ser Val Lys Gln Ala Val Leu Leu Asn Val Leu Gly Ser
65                  70                  75                  80
```

```
Gly Glu Glu Ile Pro Asp Pro Leu Ser Pro Gly Arg Gly Ile Gln
                85                  90                  95

Ala Lys Leu Lys Glu Leu Glu Asp Glu Gln Arg Asn Glu Leu Val Arg
100                 105                 110

Leu Lys Tyr Asn Asp Lys Ile Lys Glu Lys Phe Gly Lys Glu Leu Glu
    115                 120                 125

Glu Val Tyr Asn Phe Met Asn Gly Glu Ala Asn Ala Glu Ile Glu Asp
130                 135                 140

Glu Lys Gln Phe Asp Ile Leu Asn Arg Ala Gly Thr Ser Tyr Asn Lys
145                 150                 155                 160

Ile Leu Thr Glu Glu Asp Leu Gln Met Arg Arg Leu Ala Thr Ala Leu
                165                 170                 175

Gln Lys Glu Ile Gly Glu Arg Thr His Ala Glu Thr Val Met Val Lys
                180                 185                 190

Glu Tyr Arg Asp Lys Ile Asp Ala Leu Lys Asn Ala Ile Glu Val Glu
    195                 200                 205

Arg Asp Gly Met Gln Glu Glu Ala Ile Gln Glu Ile Ala Gly Met Thr
210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
                260                 265                 270

Leu Arg Thr Pro Lys Ile Glu Pro Ser Val Val Ser Thr Ile Leu Glu
    275                 280                 285

Tyr Arg Thr Lys Glu Ile Pro Asp Asn Ala Leu Ala Val Ser Val Leu
    290                 295                 300

Ser Lys Asn Arg Ala Ile Gln Glu Asn His Lys Glu Leu Met His Ile
305                 310                 315                 320

Lys Asn Glu Ile Leu Pro Arg Phe Lys Lys Ala Met Asp Glu Glu Lys
                325                 330                 335

Glu Ile Cys Gly Ile Glu Asp Lys Val Ile His Pro Lys Val Met Met
                340                 345                 350

Lys Phe Lys Ile Pro Arg Ala Gln Gln Pro Gln Ile His Val Tyr Ser
    355                 360                 365

Ala Pro Trp Asp Ser Asp Val Phe Ser Phe His Cys Ile Ser His
    370                 375                 380

His His Ala Asn Glu Ser Phe Phe Ile Gly Phe Glu Ser Ser Ile Asp
385                 390                 395                 400

Leu Val His Tyr Glu Asp Leu Thr Ala His Gly His Ala Leu Gly Ala
                405                 410                 415

Ala Gln Ala Ala Ala Gly Arg Thr Leu Thr Glu Ala Tyr Arg Glu Phe
                420                 425                 430

Leu Asn Leu Ala Ile Ser Asn Ala Phe Gly Thr Gln Met His Thr Arg
                435                 440                 445

Arg Leu Val Arg Ser Lys Thr Val His Pro Ile Tyr Leu Gly Ser Leu
450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495
```

```
Phe Gln Arg Arg Ala Ile Leu Gly Ala Leu Lys Phe Gly Cys Lys Val
                500                 505                 510
Leu Gly Asp Arg Leu Asp Val Pro Leu Phe Leu Arg Asn Ala
        515                 520                 525

<210> SEQ ID NO 20
<211> LENGTH: 526
<212> TYPE: PRT
<213> ORGANISM: artificial sequence
<220> FEATURE:
<223> OTHER INFORMATION: BTV VP5 with ACR58462

<400> SEQUENCE: 20

Met Gly Lys Val Ile Arg Ser Leu Asn Arg Phe Gly Lys Lys Val Gly
1               5                   10                  15
Asn Ala Leu Thr Ser Asn Thr Ala Lys Lys Ile Tyr Ser Thr Ile Gly
            20                  25                  30
Lys Ala Ala Glu Arg Phe Ala Glu Ser Glu Ile Gly Ser Ala Ala Ile
        35                  40                  45
Asp Gly Leu Val Gln Gly Ser Val His Ser Ile Ile Thr Gly Glu Ser
    50                  55                  60
Tyr Gly Glu Ser Val Lys Gln Ala Val Leu Leu Asn Val Leu Gly Ser
65                  70                  75                  80
Gly Glu Glu Ile Pro Asp Pro Leu Ser Pro Gly Glu Arg Gly Ile Gln
                85                  90                  95
Ala Lys Leu Lys Glu Leu Glu Asp Glu Gln Arg Asn Glu Leu Val Arg
            100                 105                 110
Leu Lys Tyr Asn Asp Lys Ile Lys Glu Lys Phe Gly Lys Glu Leu Glu
        115                 120                 125
Glu Val Tyr Asn Phe Met Asn Gly Glu Ala Asn Ala Glu Ile Glu Asp
    130                 135                 140
Glu Lys Gln Phe Asp Ile Leu Asn Lys Ala Val Thr Ser Tyr Asn Lys
145                 150                 155                 160
Ile Leu Thr Glu Glu Asp Leu Gln Met Arg Arg Leu Ala Thr Ala Leu
                165                 170                 175
Gln Lys Glu Ile Gly Glu Arg Thr His Ala Glu Thr Val Met Val Lys
            180                 185                 190
Glu Tyr Arg Asp Lys Ile Asp Ala Leu Lys Asn Ala Ile Glu Val Glu
        195                 200                 205
Arg Asp Gly Met Gln Glu Ala Ile Gln Glu Ile Ala Gly Met Thr
    210                 215                 220
Ala Asp Val Leu Glu Ala Ala Ser Glu Val Pro Leu Ile Gly Ala
225                 230                 235                 240
Gly Met Ala Thr Ala Val Ala Thr Gly Arg Ala Ile Glu Gly Ala Tyr
                245                 250                 255
Lys Leu Lys Lys Val Ile Asn Ala Leu Ser Gly Ile Asp Leu Thr His
            260                 265                 270
Leu Arg Thr Pro Lys Ile Glu Pro Ser Val Val Ser Thr Ile Leu Glu
        275                 280                 285
Tyr Arg Ala Lys Glu Ile Pro Asp Asn Ala Leu Ala Val Ser Val Leu
    290                 295                 300
Ser Lys Asn Arg Ala Ile Gln Glu Asn His Lys Glu Leu Met His Ile
305                 310                 315                 320
Lys Asn Glu Ile Leu Pro Arg Phe Lys Lys Ala Met Asp Glu Glu Lys
                325                 330                 335
```

```
Glu Ile Cys Gly Ile Glu Asp Lys Val Ile His Pro Lys Val Met Met
                340                 345                 350

Lys Phe Lys Ile Pro Arg Ala Gln Gln Pro Gln Ile His Val Tyr Ser
            355                 360                 365

Ala Pro Trp Asp Ser Asp Val Phe Phe His Cys Ile Ser His
        370                 375                 380

His His Ala Asn Glu Ser Phe Phe Leu Gly Phe Asp Leu Ser Ile Asp
385                 390                 395                 400

Leu Val His Tyr Glu Asp Leu Thr Ala His Trp His Ala Leu Gly Ala
                405                 410                 415

Ala Gln Thr Ala Ala Gly Arg Thr Leu Thr Glu Ala Tyr Arg Glu Phe
            420                 425                 430

Leu Asn Leu Ala Ile Ser Asn Ala Phe Gly Thr Gln Met His Thr Arg
        435                 440                 445

Arg Leu Val Arg Ser Lys Thr Val His Pro Ile Tyr Leu Gly Ser Leu
    450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 21
<211> LENGTH: 526
<212> TYPE: PRT
<213> ORGANISM: artificial sequence
<220> FEATURE:
<223> OTHER INFORMATION: BTV VP5 with CAE52973

<400> SEQUENCE: 21

Met Gly Lys Val Ile Arg Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
            20                  25                  30

Lys Ala Ala Glu Arg Phe Ala Glu Ser Glu Ile Gly Ser Ala Ala Ile
        35                  40                  45

Asp Gly Leu Val Gln Gly Ser Val His Ser Ile Ile Thr Gly Glu Ser
    50                  55                  60

Tyr Gly Glu Ser Val Lys Gln Ala Val Leu Leu Asn Val Leu Gly Ser
65                  70                  75                  80

Gly Glu Glu Ile Pro Asp Pro Leu Ser Pro Gly Glu Arg Gly Ile Gln
                85                  90                  95

Ala Lys Leu Lys Glu Leu Glu Asp Glu Gln Arg Asn Glu Leu Val Arg
            100                 105                 110

Leu Lys Tyr Asn Asp Lys Ile Lys Glu Lys Phe Gly Lys Glu Leu Glu
        115                 120                 125

Glu Val Tyr Asn Phe Met Asn Gly Glu Ala Asn Ala Glu Ile Glu Asp
    130                 135                 140

Glu Lys Gln Phe Asp Ile Leu Asn Lys Ala Val Thr Ser Tyr Asn Lys
145                 150                 155                 160

Ile Leu Thr Glu Glu Asp Leu Gln Met Arg Arg Leu Ala Thr Ala Leu
                165                 170                 175
```

```
Gln Lys Glu Ile Gly Glu Arg Thr His Ala Glu Thr Val Met Val Lys
            180                 185                 190

Glu Tyr Arg Asp Lys Ile Asp Ala Leu Lys Asn Ala Ile Glu Val Glu
        195                 200                 205

Arg Asp Gly Met Gln Glu Ala Ile Gln Glu Ile Ala Gly Met Thr
    210                 215                 220

Ala Asp Val Leu Glu Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
                260                 265                 270

Leu Arg Thr Pro Lys Ile Glu Pro Ser Val Val Ser Thr Ile Leu Glu
        275                 280                 285

Tyr Arg Thr Lys Glu Ile Pro Asp Asn Ala Leu Ala Val Ser Val Leu
        290                 295                 300

Ser Lys Asn Arg Ala Ile Gln Glu Asn His Lys Glu Leu Met His Ile
305                 310                 315                 320

Lys Asn Glu Ile Leu Pro Arg Phe Lys Lys Ala Met Asp Glu Lys
                325                 330                 335

Glu Ile Cys Gly Ile Glu Asp Lys Val Ile His Pro Lys Val Met Met
                340                 345                 350

Lys Phe Lys Ile Pro Arg Ala Gln Gln Pro Gln Ile His Val Tyr Ser
                355                 360                 365

Ala Pro Trp Asp Ser Asp Val Phe Phe Phe His Cys Ile Ser His
    370                 375                 380

His His Ala Asn Glu Ser Phe Phe Leu Gly Phe Asp Leu Ser Ile Asp
385                 390                 395                 400

Leu Val His Tyr Glu Asp Leu Thr Ala His Trp His Ala Leu Gly Ala
                405                 410                 415

Ala Gln Thr Ala Ala Gly Arg Thr Leu Thr Glu Ala Tyr Arg Glu Phe
                420                 425                 430

Leu Asn Leu Ala Ile Ser Asn Ala Phe Gly Thr Gln Met His Thr Arg
            435                 440                 445

Arg Leu Val Arg Ser Lys Thr Val His Pro Ile Tyr Leu Gly Ser Leu
450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
                500                 505                 510

Leu Gly Asp Arg Leu Asp Val Pro Leu Phe Leu Arg Asn Ala
                515                 520                 525

<210> SEQ ID NO 22
<211> LENGTH: 526
<212> TYPE: PRT
<213> ORGANISM: artificial sequence
<220> FEATURE:
<223> OTHER INFORMATION: BTV VP5 with CAE52974

<400> SEQUENCE: 22

Met Gly Lys Val Ile Arg Ser Leu Ser Arg Phe Gly Lys Lys Val Gly
1               5                   10                  15
```

```
Asn Ala Leu Thr Ser Asn Thr Ala Lys Lys Ile Tyr Ser Thr Ile Gly
             20                  25                  30
Lys Ala Ala Glu Arg Phe Ala Glu Ser Glu Ile Gly Ser Ala Ala Ile
         35                  40                  45
Asp Gly Leu Val Gln Gly Ser Val His Ser Ile Thr Gly Glu Ser
 50                  55                  60
Tyr Gly Glu Ser Val Lys Gln Ala Val Leu Leu Asn Met Leu Gly Asn
 65                  70                  75                  80
Gly Glu Glu Ile Pro Asp Pro Leu Ser Pro Gly Glu Arg Gly Ile Gln
                 85                  90                  95
Ala Lys Leu Lys Glu Leu Glu Asp Glu Gln Arg Asn Glu Leu Val Arg
         100                 105                 110
Leu Lys Tyr Asn Asp Lys Ile Lys Glu Lys Phe Gly Lys Glu Leu Glu
         115                 120                 125
Glu Val Tyr Asn Phe Met Asn Gly Glu Ala Asn Ala Glu Ile Glu Asp
         130                 135                 140
Glu Lys Gln Phe Asp Ile Leu Asn Lys Ala Val Thr Ser Tyr Asn Lys
145                 150                 155                 160
Ile Leu Thr Glu Glu Asp Leu Gln Met Arg Arg Leu Ala Thr Ala Leu
                 165                 170                 175
Gln Lys Glu Ile Gly Glu Arg Thr His Ala Glu Thr Val Met Val Lys
         180                 185                 190
Glu Tyr Arg Asp Lys Ile Asp Ala Leu Lys Asn Ala Ile Glu Val Glu
         195                 200                 205
Arg Asp Gly Met Gln Glu Glu Ala Ile Gln Glu Ile Ala Gly Met Thr
210                 215                 220
Ala Asp Val Leu Glu Ala Ala Ser Glu Glu Val Pro Leu Ile Gly Ala
225                 230                 235                 240
Gly Met Ala Thr Ala Val Ala Thr Gly Arg Ala Ile Glu Gly Ala Tyr
                 245                 250                 255
Lys Leu Lys Lys Val Ile Asn Ala Leu Ser Gly Ile Asp Leu Thr His
         260                 265                 270
Leu Arg Thr Pro Lys Ile Glu Pro Ser Val Val Ser Thr Ile Leu Glu
         275                 280                 285
Tyr Arg Thr Lys Glu Ile Pro Asp Asn Ala Leu Ala Val Ser Val Leu
         290                 295                 300
Ser Lys Asn Arg Ala Ile Gln Glu Asn His Lys Glu Leu Met His Ile
305                 310                 315                 320
Lys Asn Glu Ile Leu Pro Arg Phe Lys Lys Ala Met Asp Glu Glu Lys
                 325                 330                 335
Glu Ile Cys Gly Ile Glu Asp Lys Val Ile His Pro Lys Val Met Met
         340                 345                 350
Lys Phe Lys Ile Pro Arg Ala Gln Gln Pro Gln Ile His Val Tyr Ser
         355                 360                 365
Ala Pro Trp Asp Ser Asp Val Phe Phe His Cys Ile Ser His
370                 375                 380
His His Ala Asn Glu Ser Phe Leu Gly Phe Asp Leu Ser Ile Asp
385                 390                 395                 400
Leu Val His Tyr Glu Asp Leu Thr Ala His Trp His Ala Leu Gly Ala
                 405                 410                 415
Ala Gln Thr Ala Ala Gly Arg Thr Leu Thr Glu Ala Tyr Arg Glu Phe
         420                 425                 430
Leu Asn Leu Ala Ile Ser Asn Ala Phe Gly Thr Gln Met His Thr Arg
```

```
                  435                 440                 445
Arg Leu Val Arg Ser Lys Thr Val His Pro Ile Tyr Leu Gly Ser Leu
        450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 23
<211> LENGTH: 526
<212> TYPE: PRT
<213> ORGANISM: artificial sequence
<220> FEATURE:
<223> OTHER INFORMATION: BTV VP5 with CAE52979

<400> SEQUENCE: 23

Met Gly Lys Val Ile Arg Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
            20                  25                  30

Lys Ala Ala Glu Arg Phe Ala Glu Ser Glu Ile Gly Ser Ala Ala Ile
        35                  40                  45

Asp Gly Leu Val Gln Gly Ser Val His Ser Ile Leu Thr Gly Glu Ser
    50                  55                  60

Tyr Gly Glu Ser Val Lys Gln Ala Val Leu Leu Asn Val Leu Gly Ser
65                  70                  75                  80

Gly Glu Glu Ile Pro Asp Pro Leu Ser Pro Gly Glu Arg Gly Ile Gln
                85                  90                  95

Ala Lys Leu Arg Glu Leu Glu Asp Glu Gln Arg Asn Glu Leu Val Arg
            100                 105                 110

Leu Lys Tyr Asn Asp Lys Ile Lys Glu Lys Phe Gly Glu Glu Leu Glu
        115                 120                 125

Glu Val Tyr Glu Phe Met Asn Gly Ala Ala Lys Ala Glu Val Glu Asp
    130                 135                 140

Glu Lys Gln Phe Asp Ile Leu Asn Lys Ala Val Thr Ser Tyr Asn Lys
145                 150                 155                 160

Ile Leu Thr Glu Glu Asp Leu Gln Met Arg Arg Leu Ala Asn Ala Leu
                165                 170                 175

Gln Lys Glu Ile Gly Glu Arg Thr His Ala Glu Thr Val Met Val Lys
            180                 185                 190

Glu Tyr Arg Asn Lys Ile Asp Ala Leu Lys Asn Ala Ile Glu Ile Glu
        195                 200                 205

Arg Asp Gly Met Gln Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
            260                 265                 270

Leu Arg Thr Pro Lys Ile Glu Pro Ser Val Val Ser Thr Ile Leu Glu
```

```
                   275                 280                 285
Tyr Arg Thr Lys Asp Ile Pro Asp Ser Ala Leu Ala Val Ser Val Leu
            290                 295                 300

Ser Lys Asn Arg Ala Ile Gln Glu Asn His Lys Glu Leu Val His Ile
305                 310                 315                 320

Gln Asp Glu Ile Leu Pro Arg Phe Lys Lys Ala Met Asp Glu Glu Lys
                325                 330                 335

Glu Ile Cys Gly Ile Glu Asp Lys Val Ile His Pro Lys Val Met Met
            340                 345                 350

Arg Phe Lys Ile Pro Arg Ala Gln Gln Pro Gln Ile His Val Tyr Ser
        355                 360                 365

Ala Pro Trp Asp Ser Asp Val Phe Phe His Cys Ile Ser His
370                 375                 380

His His Ala Asn Glu Ser Phe Phe Leu Gly Phe Asp Leu Ser Ile Asp
385                 390                 395                 400

Leu Val His Tyr Glu Asp Leu Thr Ala His Trp His Ala Leu Gly Ala
                405                 410                 415

Ala Gln Met Ala Met Gly Arg Thr Leu Ser Glu Ala Tyr Lys Glu Phe
            420                 425                 430

Leu Asn Met Ala Ile Ser Asn Ser Tyr Gly Thr Gln Met His Thr Arg
        435                 440                 445

Arg Leu Val Arg Ser Lys Thr Val His Pro Ile Tyr Leu Gly Ser Leu
    450                 455                 460

His Tyr Asp Ile Ser Phe Pro Asp Leu Arg Gly Asn Ala Gln Lys Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 24
<211> LENGTH: 526
<212> TYPE: PRT
<213> ORGANISM: artificial sequence
<220> FEATURE:
<223> OTHER INFORMATION: BTV VP5 with CAE52991

<400> SEQUENCE: 24

Met Gly Lys Val Ile Arg Ser Leu Ser Arg Phe Gly Lys Lys Val Gly
1               5                   10                  15

Ser Ala Leu Thr Ser Asn Thr Ala Lys Lys Ile Tyr Ser Thr Ile Gly
            20                  25                  30

Lys Ala Ala Glu Arg Phe Ala Glu Ser Glu Ile Gly Ser Ala Ala Ile
        35                  40                  45

Asp Gly Leu Val Gln Gly Ser Val His Ser Ile Leu Thr Gly Glu Ser
    50                  55                  60

Tyr Gly Gln Ser Val Lys Gln Ala Val Leu Leu Asn Val Leu Gly Asn
65                  70                  75                  80

Gly Glu Glu Leu Pro Asp Pro Leu Ser Pro Gly Glu Arg Gly Met Gln
                85                  90                  95

Val Lys Leu Lys Glu Leu Glu Asp Glu Gln Arg Asn Glu Leu Val Arg
            100                 105                 110

Leu Lys Tyr Asn Asp Lys Ile Lys Glu Lys Phe Gly Lys Glu Leu Glu
```

```
            115                 120                 125
Glu Ile Tyr Glu Phe Met Asn Gly Glu Ala Lys Val Glu Ala Glu Asp
    130                 135                 140

Glu Lys Gln Phe Asp Ile Leu Asn Lys Ala Val Thr Ser Tyr Asn Lys
145                 150                 155                 160

Ile Leu Thr Glu Glu Asp Leu Gln Met Arg Arg Leu Ala Thr Ala Leu
                165                 170                 175

Gln Lys Glu Val Ser Glu Arg Thr His Ala Glu Thr Val Met Val Lys
            180                 185                 190

Glu Tyr Arg Asn Lys Ile Asp Ala Leu Lys Ser Ala Ile Glu Ile Glu
        195                 200                 205

Arg Asp Gly Met Gln Glu Glu Ala Ile Gln Glu Ile Ala Gly Met Thr
    210                 215                 220

Ala Asp Val Leu Glu Ala Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Thr His
            260                 265                 270

Leu Arg Thr Pro Lys Ile Glu Pro Ser Val Val Ser Thr Ile Leu Glu
        275                 280                 285

Tyr Arg Thr Lys Glu Ile Pro Asp Asn Ala Leu Ala Val Ser Ile Leu
    290                 295                 300

Ser Lys Asn Arg Ala Ile Gln Glu Asn His Lys Glu Leu Met His Ile
305                 310                 315                 320

Lys Asp Glu Ile Leu Pro Arg Phe Lys Lys Ala Met Asp Glu Glu Lys
                325                 330                 335

Glu Ile Cys Gly Ile Glu Asp Lys Thr Ile His Pro Lys Val Met Met
            340                 345                 350

Lys Phe Lys Ile Pro Arg Ala Gln Gln Pro Gln Ile His Val Tyr Ser
        355                 360                 365

Ala Pro Trp Asp Ser Asp Val Phe Phe His Cys Ile Ser His
    370                 375                 380

His His Ala Asn Glu Ser Phe Phe Leu Gly Phe Asp Leu Ser Ile Asp
385                 390                 395                 400

Leu Val His Tyr Glu Asp Leu Thr Ala His Trp His Ala Leu Gly Ala
                405                 410                 415

Ala Gln Met Ala Ala Gly Arg Thr Leu Thr Glu Ala Tyr Lys Glu Phe
            420                 425                 430

Leu Asn Met Ala Ile Ser Asn Val Leu Gly Thr Gln Met His Thr Arg
        435                 440                 445

Arg Leu Val Arg Ser Lys Thr Val His Pro Ile Tyr Leu Gly Ser Met
    450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 25
```

```
<211> LENGTH: 526
<212> TYPE: PRT
<213> ORGANISM: artificial sequence
<220> FEATURE:
<223> OTHER INFORMATION: BTV VP5 with CAE53011

<400> SEQUENCE: 25
```

| | | | | | | | | | | | | | | |
|---|---|---|---|---|---|---|---|---|---|---|

His His Ala Asn Glu Ser Phe Phe Leu Gly Phe Asp Leu Ser Ile Asp
385                 390                 395                 400

Leu Val His Tyr Glu Asp Leu Thr Ala His Trp His Ala Leu Gly Ala
            405                 410                 415

Ala Gln Thr Ala Ala Gly Arg Thr Leu Thr Glu Ala Tyr Arg Glu Phe
        420                 425                 430

Leu Asn Leu Ala Ile Ser Asn Ala Phe Gly Thr Gln Met His Thr Arg
    435                 440                 445

Arg Leu Val Arg Ser Lys Thr Val His Pro Ile Tyr Leu Gly Ser Leu
450                 455                 460

His Tyr Asp Ile Ser Phe Ser Asp Leu Arg Gly Asn Ala Gln Arg Ile
465                 470                 475                 480

Val Tyr Asp Asp Glu Leu Gln Met His Ile Leu Arg Gly Pro Ile His
                485                 490                 495

Phe Gln Arg Arg Ala Ile Leu Gly Ala Leu Lys Phe Gly Cys Lys Val
            500                 505                 510

Leu Gly Asp Arg Leu Asp Val Pro Leu Phe Leu Arg Asn Ala
        515                 520                 525

<210> SEQ ID NO 26
<211> LENGTH: 21
<212> TYPE: DNA
<213> ORGANISM: artificial sequence
<220> FEATURE:
<223> OTHER INFORMATION: alpha amylase leader sequence

<400> SEQUENCE: 26
atgcaggtcc tgaacacgat g                                          21

<210> SEQ ID NO 27
<211> LENGTH: 63
<212> TYPE: DNA
<213> ORGANISM: artificial sequence
<220> FEATURE:
<223> OTHER INFORMATION: RbcS (lemna gibba RbcS (SSU5B)) leader sequence

<400> SEQUENCE: 27
gaaactcccg aggtgagcaa ggatccggag tcgagcgcga agaagagaaa gagggaaagc   60
gcg                                                              63

<210> SEQ ID NO 28
<211> LENGTH: 213
<212> TYPE: DNA
<213> ORGANISM: artificial sequence
<220> FEATURE:
<223> OTHER INFORMATION: Aocs promoter

<400> SEQUENCE: 28
ctgaaagcga cgttggatgt taacatctac aaattgcctt ttcttatcga ccatgtacgt   60
aagcgcttac gtttttggtg gaccettgag gaaactggta gctgttgtgg gcctgtggtc  120
tcaagatgga tcattaattt ccaccttcac ctacgatggg gggcatcgca ccggtgagta  180
atattgtacg gctaagagcg aatttggcct gta                              213

<210> SEQ ID NO 29
<211> LENGTH: 392
<212> TYPE: DNA
<213> ORGANISM: artificial sequence
<220> FEATURE:
<223> OTHER INFORMATION: AmasPmas promoter

<400> SEQUENCE: 29

```
gcgagctggt caatcccatt gcttttgaag cagctcaaca ttgatctctt tctcgatcga      60
gggagatttt tcaaatcagt gcgcaagacg tgacgtaagt atccgagtca gttttttattt   120
ttctactaat ttggtcgttt atttcggcgt gtaggacatg gcaaccgggc ctgaatttcg    180
cgggtattct gtttctattc caactttttc ttgatccgca gccattaacg acttttgaat    240
agatacgctg acacgccaag cctcgctagt caaaagtgta ccaaacaacg ctttacagca    300
agaacggaat gcgcgtgacg ctcgcggtga cgccatttcg ccttttcaga aatggataaa    360
tagccttgct tcctattata tcttccccca aa                                   392
```

<210> SEQ ID NO 30
<211> LENGTH: 976
<212> TYPE: DNA
<213> ORGANISM: artificial sequence
<220> FEATURE:
<223> OTHER INFORMATION: LmUBQ promoter (Lemna minor ubiquitin)

<400> SEQUENCE: 30

```
cgatctgcac aaaaaaaaaa aaaaaaaact tgagaagag ccgcgaaatt accctagaat      60
cctcagaact ggccggacga gagaagcgct cgatcgaaac ccaacataaa accccttcca   120
acggcaaatt actccgcaaa acccgaaaaa taaacaaaat caacgatcac gagaaggtgc   180
aagggcaaaa agaggcagtg cgatcgagag tctacctgaa tcgtcggcgc aaaaggcgag   240
cccaccgacg aacgctccct ctagaacctg gagatgcggc gagagagaag gaaagatctt   300
cggtgggtga tgctcgctat ttatcgcaag agagttagag agatcttctt cggcggcgga   360
tttctggcat ctagcgttta acctcaccgc ccagtgctca catccttctt ctcatatttg   420
aatatttaat taacaaatga atcagtcatt tttctttaat ttttaattcc cggagagggc   480
aatgttggta tcaaaaatta tttaggaaaa attaattaca cgaataatcg gattttcccc   540
ttttttaat taatttctaa ttttggaaaa ggaaagaaaa attttagggg tatggagggc    600
aagaatgaaa tattacaaat tagggggtttt tgcgtaattt attatattta ataaagaaag   660
tcgaatattc ccatccgatt ggtagttgaa aggggccgaa aggcctcggg gtttctagag   720
atttctacat tattctcgtt tttgtcgcca agaaggtggg caattatgtt tcatgcctta   780
acttcttctt tttgtgggaa tactcttatt cttagtacaa agaaaagag tatatgcata   840
aataagatga aaatggggtt tattcgagat ttctacgtca tgtgtgactc gcttaggaaa    900
tatcgccgaa acctaacaaa ggcggtacgc tcctctcccc cgacctataa atagagacct   960
ttgcctcgtc tttctc                                                    976
```

<210> SEQ ID NO 31
<211> LENGTH: 542
<212> TYPE: DNA
<213> ORGANISM: artificial sequence
<220> FEATURE:
<223> OTHER INFORMATION: ADH1 intron

<400> SEQUENCE: 31

```
gtccgccttg tttctcctct gtctcttgat ctgactaatc ttggtttatg attcgttgag      60
taattttggg gaaagctagc ttcgtccaca gttttttttt cgatgaacag tgccgcagtg   120
gcgctgatct tgtatgctat cctgcaatcg tggtgaactt atttcttta tatccttcac    180
tcccatgaaa aggctagtaa tctttctcga tgtaacatcg tccagcactg ctattaccgt    240
```

```
gtggtccatc cgacagtctg gctgaacaca tcatacgata ttgagcaaag atcgatctat    300
cttccctgtt ctttaatgaa agacgtcatt ttcatcagta tgatctaaga atgttgcaac    360
ttgcaaggag gcgtttcttt ctttgaattt aactaactcg ttgagtggcc ctgtttctcg    420
gacgtaaggc ctttgctgct ccacacatgt ccattcgaat tttaccgtgt ttagcaaggg    480
cgaaaagttt gcatcttgat gatttagctt gactatgcga ttgctttcct ggacccgtgc    540
ag                                                                  542

<210> SEQ ID NO 32
<211> LENGTH: 535
<212> TYPE: DNA
<213> ORGANISM: artificial sequence
<220> FEATURE:
<223> OTHER INFORMATION: LmUBQ intron (Ubi intron 1)

<400> SEQUENCE: 32
gtatgcgtct ttcctccttg tgattcgatc tttctgttgg ctagatctgg tctattgatc     60
tgctctattg atctggtcta tttatcgctg catcgggatc tattgatccg tatgttgatt    120
tgggatccgt aggttggttt ggatcggaga ctgcgatttg attcttgtga tttcgcttgg    180
atttcggaaa tcggtgtggt tgaagtcgtg cgatctttta gatctgctcc tttttttatt    240
tgctatttta tatttacgtt gtttatgatc gcggattatt ttgattcgtt tattcgagat    300
ccatgccgtt taactcgttc tttgtgctcc gatctttgcg atacgtcggt cgttctagat    360
ccgttcacta ggttagtttt aagttctttg agcttgattt atatggattt gctgttttcc    420
aggaaaaatt tatgcgcgat tcttacgccc gtttccccat tttactttag gtcgtgaatt    480
cttttgatct gagaatgatg aatctgacat gtaccttccg gtttgtaatt tgcag         535
```

BLUETONGUE VIRUS RECOMBINANT VACCINES AND USES THEREOF

CROSS-REFERENCE TO RELATED APPLICATIONS

This application claims benefit of U.S. provisional application Ser. No. 61/313,164 filed Mar. 12, 2010 and U.S. provisional application Ser. No. 61/366,363 filed Jul. 21, 2010.

FIELD OF THE INVENTION

The present invention relates to compositions for combating Bluetongue Virus (BTV) infection in animals. The present invention provides pharmaceutical compositions comprising a BTV antigen, methods of vaccination against the BTV, and kits for use with such methods and compositions.

BACKGROUND OF THE INVENTION

Bluetongue (BT) is an arthropod-borne infectious viral disease of ruminants. Cattle and goats may be readily infected with the causative Bluetongue Virus (BTV) but without extensive vascular injury and therefore these species generally fail to show pronounced clinical signs. In contrast, the disease in sheep is characterized by catarrhal inflammation of the mucous membranes of the mouth, nose and forestomachs, and by inflammation of the coronary bands and laminae of the hoofs. There is an excoriation of the epithelium, and ultimately necrosis of the buccal mucosa; the swollen and inflamed tongue and mouth can take on a blue color from which the disease is named (Spreull 1905). The mortality rate in sheep is estimated at 1-30%.

BTV is the prototype virus of the *Orbivirus* genus (Reoviridae family) and is made up of at least 24 different serotypes (Wilson and Mecham 2000). Different strains of BTV have been identified world-wide throughout tropical and temperate zones. BTV infection has occurred as far as 45° N in Europe, as far as 50° N in Asia and North America, and as far South as 35°. BTV is not contagious between ruminants thus the distribution of BTV is dependent on the presence of arthropod vector species of *coides* sp. (biting midges), with different vector species occurring in different regions of the world. Recent data suggests that genetic drift and founder effect contribute to diversification of individual gene segments of field strains of BTV (Bonneau, Mullens et al. 2001).

BTV infection of ruminants is transient, while infection of the *Culicoides* insect vector is persistent. The duration of viremia depends on the animal species and the strain of BTV. It has been reported that viremia can be very transient in sheep and may last for up to 41 days in BTV-infected individuals, up to 42 days in goats, and up to 100 days in cattle. Since BTV infection of cattle often results in prolonged but not persistent viremia, cattle serve as a reservoir from which virus may be ingested by the *Culicoides* vector and then transmitted to other ruminants (Anderson, Stott et al. 1985; MacLachlan 1994; MacLachlan and Pearson 2004). The ecology of many species of *Culicoides* vectors is poorly understood and their breeding sites are largely uncharacterized, and their rates of dispersal unknown. *Culicoides sonorensis* is the principal vector of BTV in North America. Female *Culicoides* insects become persistently infected with BTV and can transmit the virus after an extrinsic incubation period of up to 14 days (Mullens, Tabachnick et al. 1995). BTV overwintering in temperate zones may occur through vertically infected insect vectors, although recent data indicates that there is reduced expression of the outer capsid genes during persistent BTV infection in larval stages of the insect vectors (White, Wilson et al. 2005).

The virions of BTV have a diameter of ~69 nm with a double-shelled coat (capsid) that sometimes is surrounded by a lipoprotein "pseudo-envelope" derived from the cell membranes of infected cells. The BTV genome includes 10 distinct segments of double-stranded RNA that collectively encode seven structural (VP1 through VP7) and four non-structural (NS1, NS2, NS3 and NS3a) proteins (Roy 1996); Nine of the genome segments are monocistronic whereas segment 10 encodes both NS3 and NS3A using a second, inframe initiation codon. Genomic RNA is encapsidated in the icosahedral virion particle by a double layered protein capsid (Verwoerd, Els et al. 1972). The icosahedral core consists of two major (VP3 and VP7) and three minor proteins (VP1, VP4, VP6) and is surrounded by the outer capsid which consists of VP2 and VP5 that respectively are encoded by genomic segments 2 and 5 (Roy 1996). VP2 is responsible for binding and entry of BTV into cells, neutralization, serotype-specificity and hemagglutination. Multimeric forms of VP2 (dimers and trimers) decorate much of the surface of a VP5 scaffold on the outer surface of viral particles (Hassan and Roy 1999). VP2 varies most amongst the 24 BTV serotypes, and levels of anti-VP2 antibody correlate with virus neutralization in vitro and in vivo (Huismans and Erasmus 1981). VP5 also varies markedly between different serotypes and strains of BTV (de Mattos, de Mattos et al. 1994; DeMaula, Bonneau et al. 2000) and although no VP5-specific neutralizing MAb's have been identified to date, data suggests that this protein has a role in neutralization and serotype determination through its conformational influence on VP2 (Huismans and Erasmus 1981; Roy, Urakawa et al. 1990; DeMaula et al., 2000). Purified VP2 immunoadsorbed with BTV anti-core serum to remove trace amounts of VP7 provided protection against same BTV serotype infection in sheep (Huismans, van der Walt et al. 1987). Recent results show that VP2 and NS1 express epitopes recognized by cytotoxic T-lymphocytes (CTL) (Andrew, Whiteley et al. 1995) while it is unlikely that VP7 and VP5 have CTL epitopes. So far, VP3, VP4, VP6, NS2 and NS3 have not stimulated a CTL response in sheep (Lobato, Coupar et al. 1997).

Lobato and Coupar (Lobato, Coupar et al. 1997) developed vaccinia virus-based expression vectors containing various inserts corresponding to nucleotide sequences encoding for structural proteins VP2, VP5 and VP7 of BTV for both in vivo and in vitro studies. These expression vectors were administered to rabbits and sheep to evaluate the immune response with respect to ELISA and neutralizing antibody titer, and the protective efficacy of the VP2 and VP5 constructs was tested in sheep. Vaccinia virus-expressed VP2, VP5 and VP2+VP5 were protective, with the most reproducible protection occurring in animals immunized with both VP2 and VP5 however protection even with this construct was variable and not fully effective. Efforts at developing recombinant BTV vaccine compositions can be found, for example, in published US patent application US 2007/280960. Still others have described BTV immunological compositions containing various BTV antigens, produced for example, by baculovirus (see for example U.S. Pat. Nos. 5,833,995 and 5,690,938).

Thus, it would be advantageous to provide improved immunogenic and vaccine compositions against BTV, and methods for making and using such compositions, including such compositions that provide for differential diagnostic methods, assays and kits.

Recently, plants have been investigated as a source for the production of therapeutic agents such as vaccines, antibodies, and biopharmaceuticals. However, the production of vaccines, antibodies, proteins, and biopharmaceuticals from plants is far from a remedial process, and there are numerous obstacles that are commonly associated with such vaccine production. Limitations to successfully producing plant vaccines include low yield of the bioproduct or expressed antigen (Chargelegue et al., Trends in Plant Science 2001, 6, 495-496), protein instability, inconsistencies in product quality (Schillberg et al., Vaccine 2005, 23, 1764-1769), and insufficient capacity to produce viral-like products of expected size and immunogenicity (Arntzen et al., Vaccine 2005, 23, 1753-1756). In order to address these problems, codon optimization, careful approaches to harvesting and purifying plant products, use of plant parts such as chloroplasts to increase uptake of the material, and improved subcellular targeting are all being considered as potential strategies (Koprowski, Vaccine 2005, 23, 1757-1763).

Considering the susceptibility of animals to BTV, a method of preventing BTV infection and protecting animals is essential. Accordingly, there is a need for an effective vaccine against BTV.

SUMMARY OF THE INVENTION

Compositions comprising an antigenic BTV polypeptide and fragments and variants thereof are provided. The BTV antigens and fragments and variants thereof possess immunogenic and protective properties. The BTV antigens may be produced in a plant or algae.

The antigenic polypeptides and fragments and variants thereof can be formulated into vaccines and/or pharmaceutical compositions. Such vaccines can be used to vaccinate an animal and provide protection against at least one BTV strain.

Methods of the invention include methods for making the antigenic polypeptides in plant or algae. Methods also include methods of use including administering to an animal an effective amount of an antigenic polypeptide or fragment or variant thereof to produce a protective immunogenic response. After production in plant or algae, the antigenic polypeptide can be partially or substantially purified for use as a vaccine.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 depicts a table summarizing the SEQ ID NO assigned to the DNA and Protein sequences.

FIG. 4 depicts the pCG101 plasmid encoding the BTV1 VP2-c-myc (SEQ ID NO:6) used as positive control for screening.

FIG. 5 is a Western blot of CHO cell lysates indicating the AHSV VP5 10AE12 antibody selectively detects pCG102 expressed BTV1 VP5 protein (SEQ ID NO:10).

FIGS. 7a and 7b are Western blots of the lysates of CHO cells that were transfected with the indicated constructs. Both the L167 and L168 polyclonal BTV1 VP2 antibodies selectively detected the VP2 protein (SEQ ID NO:4) expressed in cells transfected with pCG100.

FIG. 8 shows the sequence alignment of the polynucleotides encoding BTV VP2 and the sequence identity percentage.

FIG. 9 shows the sequence alignment of the polynucleotides encoding BTV VP5 and the sequence identity percentage.

FIG. 10 depicts the identity and placement of the Duckweed-optimized BTV1 antigens for the 4 Duckweed expression constructs.

FIG. 11 depicts the pMerD01 plasmid containing the cytoplasmically localized VP2 and VP5 in tandem.

FIG. 12 depicts the MerD02 plasmid containing the cytoplasmically localized VP2 with optimized 5'UTR and VP5 in tandem.

FIG. 13 depicts the MerD03 plasmid, cytoplasmically localized VP2 alone.

FIG. 14 depicts the MerD04 plasmid, cytoplasmically localized VP2 with optimized 5'UTR alone.

FIG. 15 depicts representative Western blots of lysates from Duckweed expressing various MerD constructs using the VP2 antibody.

FIG. 16 depicts representative Western blots of lysates from Duckweed expressing MerD01 construct using the VP2 and the VP5 antibodies.

FIG. 17 depicts a VP2 Western blot of lysates from Duckweed expressing MerD01, MerD02, MerD03, and Mer04.

FIG. 18 depicts a VP5 monoclonal antibody clone #10AE12 Western blot of lysates from Duckweed expressing MerD01 and MerD02.

FIG. 20 depicts the mean size of local reactions at injection sites.

FIG. 21 depicts rectal temperature following first BTV vaccination.

FIG. 22 depicts rectal temperature following second BTV vaccination.

FIG. 24 depicts clinical signs following BTV challenge.

FIG. 25 depicts BTV1 antibody titer by seroneutralization.

FIG. 26 depicts mean viraemia titre measured by qRT-PCR in each treatment group.

FIG. 27 shows the protein sequence alignment of BTV1 VP2 and the sequence identity percentage.

FIG. 28 shows the protein sequence alignment of seven BTV1 VP5 and one BTV2 VP5 sequences and the sequence identity percentage.

DETAILED DESCRIPTION

Figure 2:
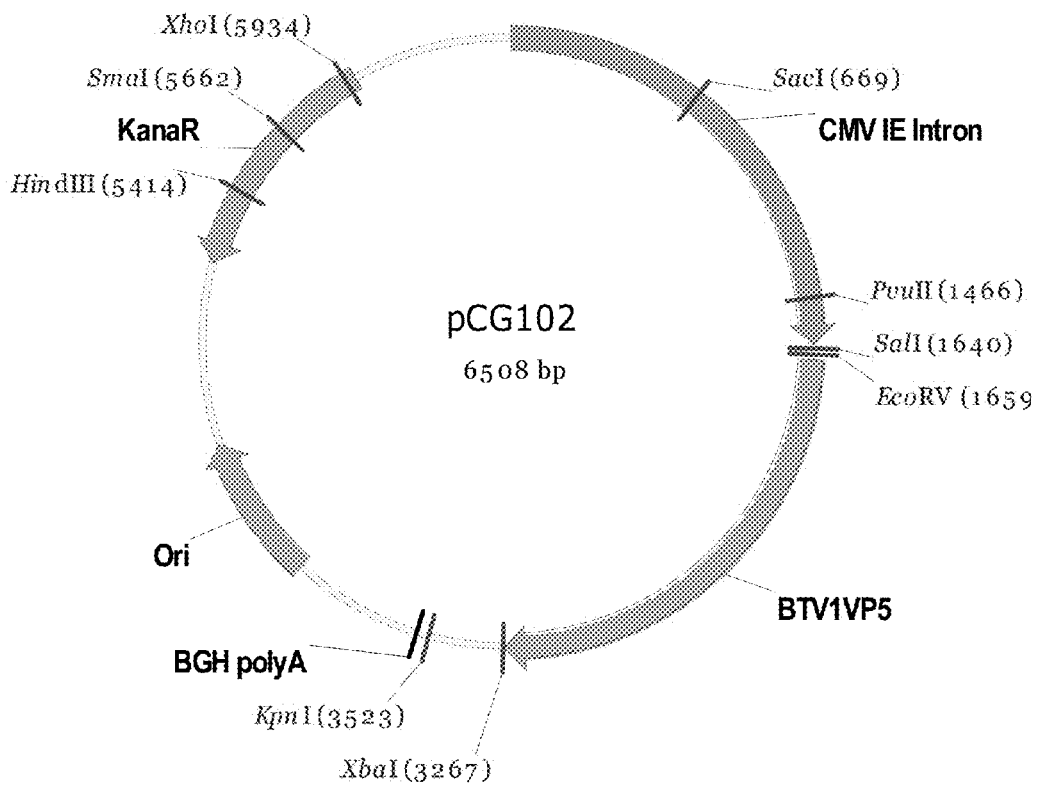
FIG. 2 depicts the pCG102 plasmid encoding the BTV1 VP5 (SEQ ID NO:10) used as positive control for screening.
Figure 3:
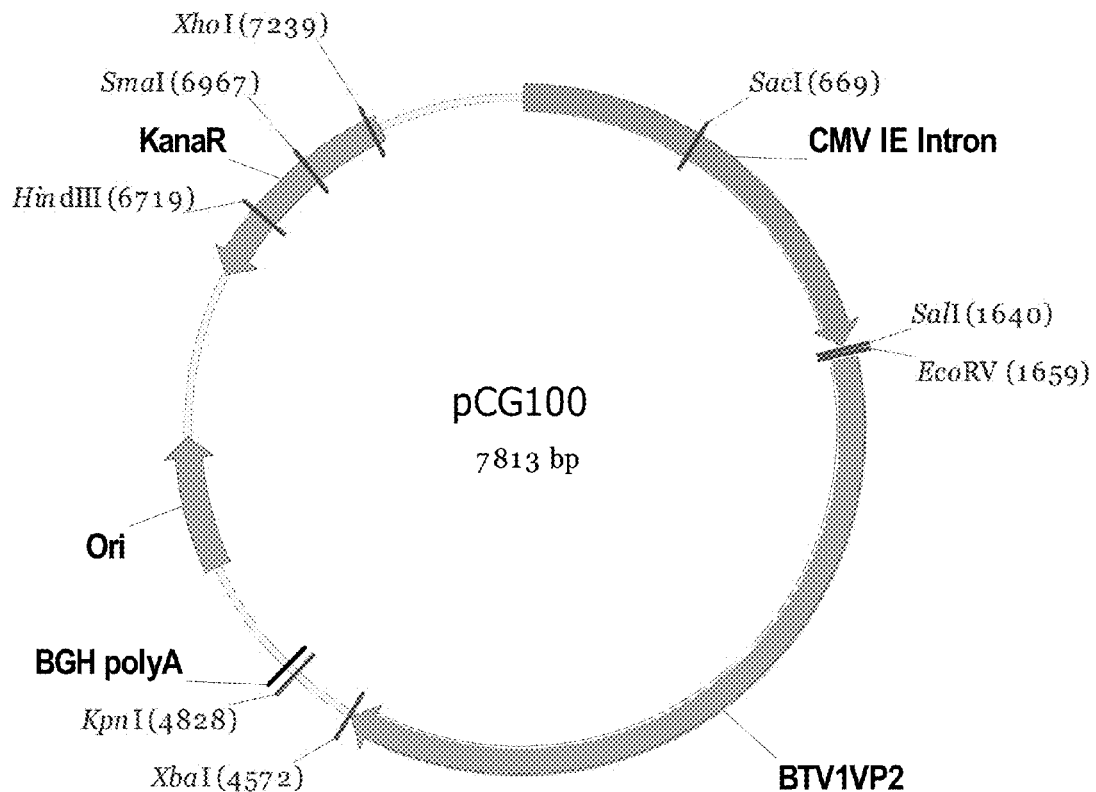
FIG. 3 depicts the pCG100 plasmid encoding the BTV1 VP2 (SEQ ID NO:4) used as positive control for screening.
Figure 6:
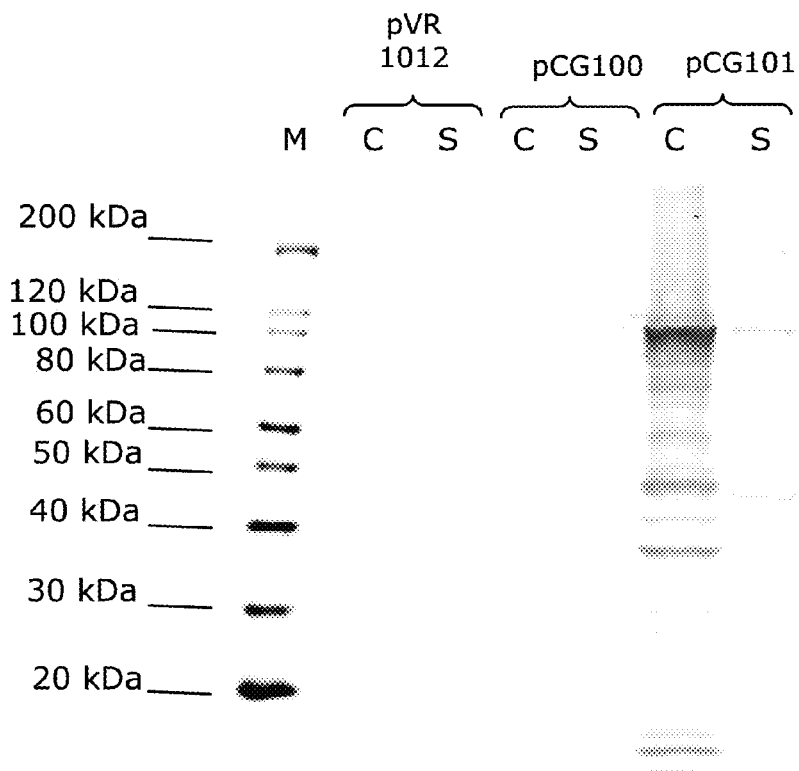
FIG. 6 is a Western blot of CHO cell lysates indicating the mouse anti-c-Myc antibody selectively detects the c-Myc-tagged pCG101 expressed BTV1 VP2 protein (SEQ ID NO:6), but does not detect the untagged pCG100 expressed BTV1 VP2 protein (SEQ ID NO:4).
Figure 19:
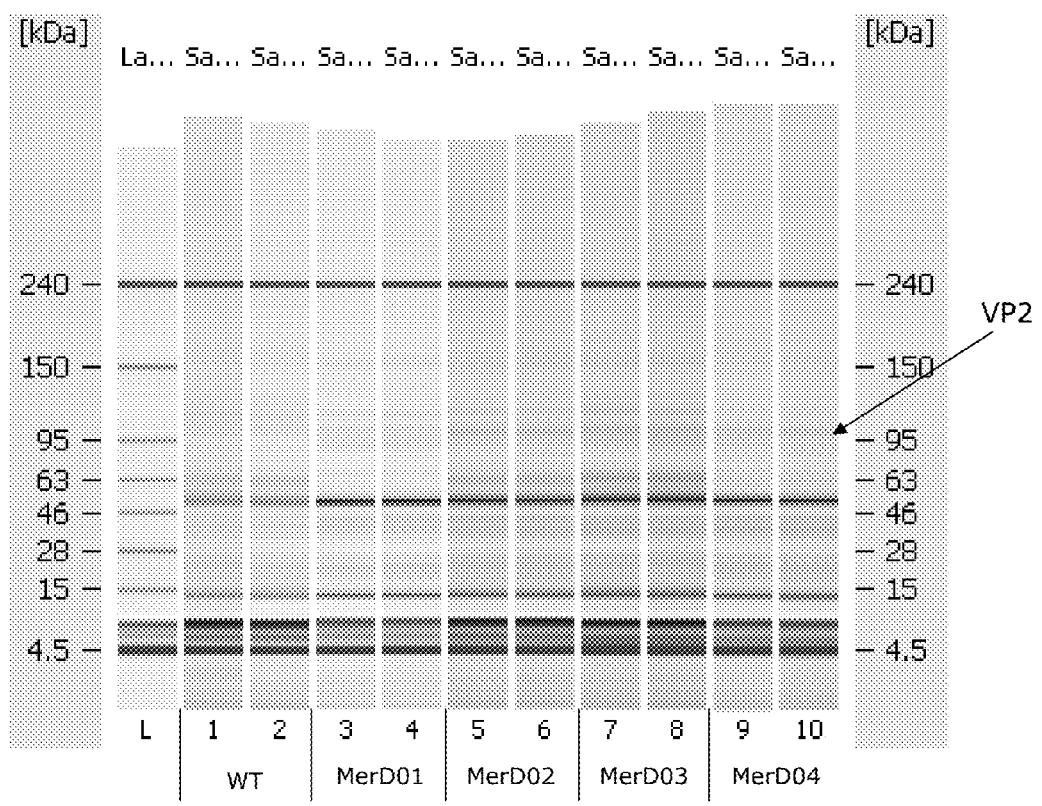
FIG. 19 depicts a representative image used for Agilent 2100 Bioanalyzer densitometry analysis of VP2.

Compositions comprising a BTV polypeptide, antigen and fragments and variants thereof that elicit an immunogenic response in an animal are provided. The antigenic polypeptides or fragments or variants thereof are produced in a plant or algae. The antigenic polypeptides or fragments or variants may be formulated into vaccines or pharmaceutical compositions and used to elicit or stimulate a protective response in an animal. In one embodiment the polypeptide antigen is a BTV VP2 or BTV VP5 polypeptide or active fragment or variant thereof.

It is recognized that the antigenic polypeptides of the invention may be full length polypeptides or active fragments or variants thereof. By "active fragments" or "active variants" is intended that the fragments or variants retain the antigenic nature of the polypeptide. Thus, the present invention encompasses any BTV polypeptide, antigen, epitope or immunogen that elicits an immunogenic response in an animal. The BTV polypeptide, antigen, epitope or immunogen may be any BTV polypeptide, antigen, epitope or immunogen, such as, but not limited to, a protein, peptide or fragment or variant thereof, that elicits, induces or stimulates a response in an animal, such as an ovine, bovine, or caprine.

The present invention relates to bovine, ovine, or caprine vaccines or compositions which may comprise an effective amount of a recombinant BTV antigen and a pharmaceutically or veterinarily acceptable carrier, excipient, adjuvant, or vehicle.

In some embodiments, the vaccines further comprise adjuvants, such as the oil-in-water (O/W) emulsions described in U.S. Pat. No. 7,371,395.

In still other embodiments, the adjuvants include EMULSIGEN®, Aluminum Hydroxide and Saponin, CpG, or combinations thereof.

In some embodiments, the response in the animal is a protective immune response.

By "animal" it is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The term "plants" as used herein includes both dicotyledonous (dicot) plants and monocotyledonous (monocot) plant. Dicot plants include, but are not limited to, legumes such as pea, alfalfa and soybean, carrot, celery, tomato, potato, tobacco, pepper, oilseed rape, beet, cabbage, cauliflower, broccoli, lettuce, peanut, and the like. Monocot plants include, but are not limited to, cereals such as wheat, barley, sorghum and millet, rye, triticale, maize, rice or oats, sugarcane, duckweed, grasses, and the like. The term "plant" also includes non-flowering plants including, but not limited to, ferns, horsetails, club mosses, mosses, liverworts, hornworts, algae. The term "algae" and "alga" as used herein includes any strain of algae capable of producing a polypeptide or fragment or variant thereof. The algae may include red, brown, and green algae, gametophytes, and the like. The algae may be microalgae. The microalgae may be Thraustochytriaceae, for example, *Schizochytrium, Thraustochytrium, Labyrinthuloides*, and *Japonochytrium*.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The antigenic polypeptides of the invention are capable of protecting against BTV. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein, polypeptide, or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed the invention encompasses active fragments and variants of the antigenic polypeptide. Thus, the term "immunogenic protein, polypeptide, or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a BTV polypeptide. A polynucleotide encoding a fragment of a BTV polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin™ Peptide Synthesis Kits de Chiron) and algorithms (De Groot et al., 1999; PCT/US2004/022605) can be used in the practice of the invention.

The term "nucleic acid" or "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a BTV antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" it is intended that such that the polypeptide represents several embodiments at least 60%, at least 70%, at least 80%, at least 90%, at least 95%, or at least 98%, or more of the cellular components or materials have been removed. Likewise, the polypeptide may be partially purified. By "partially purified"

is intended that less than 60% of the cellular components or material is removed. The same applies to polynucleotides. The polypeptides disclosed herein can be purified by any of the means known in the art.

As noted above, the antigenic polypeptides or fragments or variants thereof are BTV antigenic polypeptides that are produced in plant or algae. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

In one aspect, the present invention provides BTV polypeptides from ovine, bovine, or caprine. In another aspect, the present invention provides a polypeptide having a sequence as set forth in SEQ ID NO:4, 6, 10, 11, 12, 13, 14, 15, 16, 17, 18, 19, 20, 21, 22, 23, 24, or 25, and variant or fragment thereof.

Moreover, homologs of BTV polypeptides from ovine, bovine, or caprine are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type BTV polypeptide can differ from the wild-type BTV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type BTV polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the BTV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for BTV polypeptides, the DNA sequence of the BTV protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of BTV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the BTV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention further encompasses the BTV polynucleotides contained in a vector molecule or an expression vector and operably linked to a promoter element and optionally to an enhancer.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to ovine, bovine, and caprine vaccines or pharmaceutical or immunological compositions which may comprise an effective amount of a recombinant BTV antigens and a pharmaceutically or veterinarily acceptable carrier, excipient, or vehicle.

The subject matter described herein is directed in part, to compositions and methods related to the BTV antigen prepared in a plant or alga expression system that was highly immunogenic and protected animals against challenge from BTV strains.

Compositions

The present invention relates to a BTV vaccine or composition which may comprise an effective amount of a recombinant BTV antigen and a pharmaceutically or veterinarily acceptable carrier, excipient, or vehicle. In one embodiment, the recombinant BTV antigen is expressed in a plant or alga.

In an embodiment, the subject matter disclosed herein is directed to a composition comprising a BTV antigen produced by a duckweed expression system and plant material from duckweed, including the genus Lemna, and a pharmaceutical or veterinarily acceptable carrier, excipient or vehicle.

In one embodiment, the recombinant BTV antigen is expressed in algae. In yet another embodiment, the algae are selected from Schizochytrium. In one embodiment, the recombinant BTV antigen may be expressed in a Schizochytrium protein expression system, as described, for example, in U.S. Pat. No. 7,001,772 and US patent application publication No. 2008/0022422.

In an embodiment, the subject matter disclosed herein is directed to a protein produced by a plant or alga expression system comprising a BTV antigen and material from the plant or alga.

In an embodiment, the subject matter disclosed herein is directed to a vaccine or composition comprising a BTV antigen produced by a duckweed expression system and plant material from duckweed.

In an embodiment, the subject matter disclosed herein is directed to a stably transformed plant or plant culture that expresses a BTV antigen wherein the plant or plant culture is duckweed.

The present invention encompasses any BTV polypeptide, antigen, epitope or immunogen that elicits an immunogenic response in an animal, such as an ovine, bovine, or caprine. The BTV polypeptide, antigen, epitope or immunogen may be any BTV polypeptide, antigen, epitope or immunogen, such as, but not limited to, a protein, peptide or fragment thereof, that elicits, induces or stimulates a response in an animal, such as an ovine, bovine, or caprine.

In an embodiment wherein the BTV immunological composition or vaccine is a recombinant immunological composition or vaccine, the composition or vaccine comprising a recombinant vector and a pharmaceutical or veterinary acceptable excipient, carrier or vehicle; the recombinant vector is plant expression vector which may comprise a polynucleotide encoding a polypeptide, antigen, epitope or immunogen. The BTV polypeptide, antigen, epitope or immunogen, may be VP1, VP2, VP3, VP4, VP5, NS1, VP7, NS2, VP6, NS3, NS3a, or any fragment thereof.

In another embodiment, the BTV polypeptide, antigen, epitope or immunogen may be derived from an ovine, bovine, or caprine infected with a BTV strain. In one embodiment, the BTV antigen, epitope or immunogen is an RNA polymerase (VP1), an outer capsid protein (VP2, VP5), an inner capsid protein (VP3), a capping enzyme (VP4), a tubule forming protein (NS1), an outer core surface protein (VP7), a matrix protein (NS2), a helicase (VP6), and glycoproteins (NS3 and NS3a). Table 1 (modified from Wilson and Mecham 2000) below summarizes the genes of BTV and their protein function.

TABLE 1

Bluetongue virus genes and encoded proteins with location, properties, and function of proteins

| Genome Segment | Protein | Location | Properties & Function |
|---|---|---|---|
| L1 (3954 bp) (150 kDa) | VP1 | Within the sub-core at the 5-fold axis | RNA dependent RNA polymerase |
| L2 (2926 bp) (111 kDa) | VP2 | Outer capsid (trimer) | Outer capsid, serotype specific antigen, mammalian cell attachment protein, neutralizing epitopes |
| L3 (2770 bp) (103 kDa) | VP3 | Sub-core capsid layer (T = 2 symmetry) | Innermost protein capsid shell, sub-core capsid layer, self assembles, retains icosahedral symmetry, RNA binding, interacts with internal minor proteins |
| M4 (2011 bp) (76 kDa) | VP4 | Within the sub-core at the 5-fold axis (dimer) | Capping enzyme. guanylyltransferase |
| M5 (1638 bp) (59 kDa) | VP5 | Outer capsid (trimer) | Inner outer capsid protein, can affect virus serotype characteristics |
| M6 (1769 bp) (64 kDa) | NS1 | Cytoplasm | Forms tubules in the cell cytoplasm |
| S7 (1156 bp) (38 kDa) | VP7 | Outer core (T = 13 symmetry, trimer) | Outer core surface protein, immuno-dominant major serogroup specific antigen, attachment protein for vector insect cells, reacts with 'core neutralizing' antibodies |
| S8 (1124 bp) (41 kDa) | NS2 | Cytoplasm, viral inclusion bodies (VIB) | Important viral inclusion body matrix protein, ssRNA binding, phosphorylated, can be associated with outer capsid |
| S9 (1046 bp) (36 kDa) | VP6 | Within the sub-core at the 5-fold axis | ssRNA and dsRNA binding, helicase, NTPase |
| S10 (822 bp) (24 kDa) | NS3, NS3a | Cell membranes | Glycoproteins, membrane proteins, involved in cell exit |

In an embodiment wherein the BTV immunological composition or vaccine is a recombinant immunological composition or vaccine, the composition or vaccine comprising a recombinant vector and a pharmaceutical or veterinary acceptable excipient, carrier or vehicle; the recombinant vector is plant expression vector which may comprise a polynucleotide encoding a BTV polypeptide, antigen, epitope or immunogen. The BTV polypeptide, antigen, epitope or immunogen, may be a BTV outer capsid polypeptide (VP2, VP5), core or sub-core capsid protein (V1, VP3, or VP4), or other polypeptides such as NS1, NS2, NS3, VP6, or VP7.

In one embodiment, the BTV antigen, epitope or immunogen is VP2 or VP5. In another embodiment, the VP2 may be modified such that it is localized to the cytoplasm when expressed in duckweed. In another embodiment, the VP2 may have a 5'UTR optimized for expression in duckweed.

In yet another embodiment, the BTV antigen may be derived from BTV1. In one embodiment, the BTV1 sequences are optimized to express in duckweed.

In another embodiment, the BTV antigen may be VP2 or VP5. In yet another embodiment, the BTV antigen may be VP2 or VP5 of BTV serotype 1, 2, 3, 4, 5, 6, 7, 8, 9, 10, 11, 12, 13, 14, 15, 16, 17, 18, 19, 20, 21, 22, 23, or 24. In another embodiment, the VP2 or VP5 is isolated from the French isolate.

The present invention relates to a BTV composition or vaccine which may comprise an effective amount of a recombinant BTV antigen and a pharmaceutically or veterinarily acceptable carrier, excipient, adjuvant, or vehicle. In one embodiment, the BTV antigen may be BTV VP2 or VP5.

In another embodiment, the recombinant BTV antigen is expressed in a plant or alga. In yet another embodiment, the plant is a duckweed plant, including a *Lemna* plant. In yet another embodiment, the plant is *Lemna minor*. In one embodiment, the recombinant BTV antigen may be expressed in a proprietary *Lemna minor* protein expression system, advantageously Biolex's LEX system[SM].

In another embodiment, pharmaceutically or veterinarily acceptable carrier, excipient, adjuvant, or vehicle may be a water-in-oil emulsion. In yet another embodiment, the water-in-oil emulsion may be a water/oil/water (W/O/W) triple emulsion. In still another embodiment, the adjuvants include EMULSIGEN®, Aluminum Hydroxide and Saponin, CpG, or combinations thereof.

The invention further encompasses the BTV polynucleotides contained in a vector molecule or an expression vector and operably linked to a promoter element and optionally to an enhancer.

In one aspect, the present invention provides BTV polypeptides having a sequence as set forth in SEQ ID NO:4, 6, 10, 11, 12, 13, 14, 15, 16, 17, 18, 19, 20, 21, 22, 23, 24, or 25, and variant or fragment thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptides having a sequence as set forth in SEQ ID NO: 4, 6, 10, 11, 12, 13, 14, 15, 16, 17, 18, 19, 20, 21, 22, 23, 24, or 25, In yet another aspect, the present invention provides fragments and variants of the BTV polypeptides identified above (SEQ ID NO: 4, 6, 10, 11, 12, 13, 14, 15, 16, 17, 18, 19, 20, 21, 22, 23, 24, or 25) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 4, 6, 10, 11, 12, 13, 14, 15, 16, 17, 18, 19, 20, 21, 22, 23, 24, or 25.

An immunogenic fragment of a BTV polypeptide includes at least 8, 10, 15, or 20 consecutive amino acids, at least 21 amino acids, at least 23 amino acids, at least 25 amino acids, or at least 30 amino acids of a BTV polypeptide having a sequence as set forth in SEQ ID NO: 4, 6, 10, 11, 12, 13, 14, 15, 16, 17, 18, 19, 20, 21, 22, 23, 24, or 25, or variants thereof. In another embodiment, a fragment of a BTV polypeptide includes a specific antigenic epitope found on a full-length BTV polypeptide.

In another aspect, the present invention provides a polynucleotide encoding a BTV polypeptide, such as a polynucleotide encoding a polypeptide having a sequence as set forth in SEQ ID NO: 4, 6, 10, 11, 12, 13, 14, 15, 16, 17, 18, 19, 20, 21, 22, 23, 24, or 25. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 4, 6, 10, 11, 12, 13, 14, 15, 16, 17, 18, 19, 20, 21, 22, 23, 24, or 25, or a conservative variant, an allelic variant, a homolog or an immunogenic fragment comprising at least eight or at least ten consecutive amino acids of one of these polypeptides, or a combination of these polypeptides.

In another aspect, the present invention provides a polynucleotide having a nucleotide sequence as set forth in SEQ ID NO: 1, 2, 3, 5, 6, 7, 8, or 9, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 2, 3, 5, 6, 7, 8, or 9, or a variant thereof.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a BTV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. a BTV peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more BTV polypeptides, antigens, epitopes or immunogens. In one embodiment, the vector contains and expresses a polynucleotide that comprises, consists essentially of, or consists of a polynucleotide coding for (and advantageously expressing) a BTV antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a BTV polypeptide, antigen, epitope or immunogen, or a fragment thereof.

According to another embodiment, the vector or vectors in the preparation comprise, or consist essentially of, or consist of polynucleotide(s) encoding one or more proteins or fragment(s) thereof of a BTV polypeptide, antigen, epitope or immunogen, the vector or vectors expressing the polynucleotide(s). In another embodiment, the preparation comprises one, two, or more vectors comprising polynucleotides encoding and expressing, advantageously in vivo, a BTV polypeptide, antigen, fusion protein or an epitope thereof. The invention is also directed at mixtures of vectors that comprise polynucleotides encoding and expressing different BTV polypeptides, antigens, epitopes or immunogens, e.g., a BTV polypeptide, antigen, epitope or immunogen from different animal species such as, but not limited to, ovine, bovine, or caprine.

According to a yet further embodiment of the invention, the expression vector is a plasmid vector or a DNA plasmid vector, in particular an in vivo expression vector. In a specific, non-limiting example, the pVR1020 or 1012 plasmid (VI-CAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) of the sequence having Genbank accession number HUMTPA14. In another specific, non-limiting example, the plasmid utilized as a vector for the insertion of a polynucleotide sequence can contain the signal peptide sequence of equine IGF1 from amino acid M(24) to amino acid A(48) of the sequence having Genbank accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or consists essentially of, in addition to the polynucleotide encoding a BTV antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995.). The CMV-IE promoter can comprise the actual promoter part, which may or may not be associated with the enhancer part. Reference can be made to EP-A-260

148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter has either a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Any of constitutive, regulatable, or stimulus-dependent promoters may be used. For example, constitutive promoters may include the mannopine synthase promoter from *Agrobacterium tumefaciens*. Alternatively, it may be advantageous to use heat shock gene promoters, drought-inducible gene promoters, pathogen-inducible gene promoters, wound-inducible gene promoters, and light/dark-inducible gene promoters. It may be useful to use promoters that are controlled by plant growth regulators, such as abscissic acid, auxins, cytokinins, and gibberellic acid. Promoters may also be chosen that give tissue-specific expression (e.g., root, leaf, and floral-specific promoters).

The plasmids may comprise other expression control elements. It is particularly advantageous to incorporate stabilizing sequence(s), e.g., intron sequence(s), for example, maize alcohol dehydrogenase intron (Callis et al. Genes & Dev.1 (10):1183-1200, December 1987), the first intron of the hCMV-IE (PCT Application No. WO1989/01036), the intron II of the rabbit β-globin gene (van Ooyen et al., 1979). In another embodiment, the plasmids may comprise 3' UTR. The 3' UTR may be, but not limited to, *agrobacterium* nopaline synthase (Nos) 3' UTR (Nopaline synthase: transcript mapping and DNA sequence. Depicker, A. et al. J. Mol. Appl. Genet., 1982; Bevan, NAR, 1984, 12(22): 8711-8721).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant BTV antigen is expressed in a transgenic plant or alga. In another embodiment, the transgenic plant is a *Lemna* plant. In yet another embodiment, the transgenic plant is *Lemna minor* (duckweed). In yet another embodiment, the recombinant BTV antigen may be expressed in the *Lemna minor* (duckweed) protein expression system, the Biolex's LEX system$^{SM}$. Details of the *Lemna minor* (duckweed) protein expression system may be found, for example, in U.S. Pat. Nos. 6,815,184, 7,022,309, 7,160,717, 7,176,024, 6,040,498, and 7,161,064. In yet another embodiment, the transgenic alga is *Schizochytrium*. Details of the algal protein expression system may be found, for example, in U.S. Pat. No. 7,001,772, US 2008/0022422. The BTV antigen in the embodiments may be any polypeptide disclosed herein, or a polypeptide encoded by any polynucleotide disclosed herein.

Methods for Expressing BTV Polypeptides in Duckweed or Microalga

Thus, in some embodiments of the invention, antigenic BTV polypeptides, or fragments or variants thereof, are expressed in duckweed or microalga. These methods comprise the use of expression cassettes that are introduced into a duckweed plant or microalga using any suitable transformation method known in the art. Polynucleotides within these expression cassettes can be modified for enhanced expression of the antigenic BTV polypeptide, or fragment or variant thereof, in duckweed or microalga, as follows.

Cassettes for Duckweed or Microalga Expression of Antigenic BTV Polypeptides

Transgenic duckweed or microalga expressing a BTV polypeptide, or fragment or variant thereof, is obtained by transformation of duckweed or microalga with an expression cassette comprising a polynucleotide encoding the antigenic BTV polypeptide, or fragment or variant thereof. In this manner, a polynucleotide encoding the BTV polypeptide of interest, or fragment or variant thereof, is constructed within an expression cassette and introduced into a duckweed plant or microalga culture by any suitable transformation method known in the art.

In some embodiments, the duckweed plant or microalga that is transformed with an expression cassette comprising polynucleotide encoding the BTV polypeptide of interest, or fragment or variant thereof, has also been transformed with an expression cassette that provides for expression of another heterologous polypeptide of interest, for example, another BTV polypeptide, fragment, or variant thereof. The expression cassette providing for expression of another heterologous polypeptide of interest can be provided on the same polynucleotide (for example, on the same transformation vector) for introduction into a duckweed plant or microalga, or on a different polynucleotide (for example, on different transformation vectors) for introduction into the duckweed plant or microalga at the same time or at different times, by the same or by different methods of introduction, for example, by the same or different transformation methods.

The expression cassettes for use in transformation of duckweed or microalga comprise expression control elements that at least comprise a transcriptional initiation region (e.g., a promoter) operably linked to the polynucleotide of interest, i.e., a polynucleotide encoding a BTV polypeptide, fragment, or variant thereof "Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame. Such an expression cassette is provided with a plurality of restriction sites for insertion of the polynucleotide or polynucleotides of interest (e.g., one polynucleotide of interest, two polynucleotides of interest, etc.) to be under the transcriptional regulation of the promoter and other expression control elements. In particular embodiments of the invention, the polynucleotide to be transferred contains two or more expression cassettes, each of which contains at least one polynucleotide of interest.

By "expression control element" is intended a regulatory region of DNA, usually comprising a TATA box, capable of directing RNA polymerase II, or in some embodiments, RNA polymerase III, to initiate RNA synthesis at the appropriate transcription initiation site for a particular coding sequence. An expression control element may additionally comprise other recognition sequences generally positioned upstream or 5' to the TATA box, which influence (e.g., enhance) the transcription initiation rate. Furthermore, an expression control element may additionally comprise sequences generally positioned downstream or 3' to the TATA box, which influence (e.g., enhance) the transcription initiation rate.

The transcriptional initiation region (e.g., a promoter) may be native or homologous or foreign or heterologous to the duckweed or microalga host, or could be the natural sequence or a synthetic sequence. By foreign, it is intended that the transcriptional initiation region is not found in the wild-type duckweed or microalga host into which the transcriptional initiation region is introduced. By "functional promoter" is intended the promoter, when operably linked to a sequence encoding a BTV polypeptide of interest, or fragment or variant thereof, is capable of driving expression (i.e., transcription and translation) of the encoded polypeptide, fragment, or variant. The promoters can be selected based on the desired outcome. Thus the expression cassettes of the invention can comprise constitutive, inducible, tissue-preferred, or other promoters for expression in duckweed.

Any suitable promoter known in the art can be employed in the expression cassettes according to the present invention, including bacterial, yeast, fungal, insect, mammalian, and plant promoters. For example, plant promoters, including duckweed or microalga promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) *Plant Mol. Biol.* 15:49). Other promoters from viruses that infect plants or microalgae are also suitable, including, but not limited to, promoters isolated from Dasheen mosaic virus, *Chlorella* virus (e.g., the *Chlorella* virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Expression control elements, including promoters, can be chosen to give a desired level of regulation. For example, in some instances, it may be advantageous to use a promoter that confers constitutive expression (e.g., the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646). In the present invention, the expression cassette can contain activating nucleotide sequences inserted upstream of the promoter sequence to enhance the expression of the antigenic BTV polypeptide of interest, or fragment or variant thereof. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646).

The expression cassette thus includes in the 5'-3' direction of transcription, an expression control element comprising a transcriptional and translational initiation region, a polynucleotide of encoding an antigenic BTV polypeptide of interest (or fragment or variant thereof), and a transcriptional and translational termination region functional in plants. Any suitable termination sequence known in the art may be used in accordance with the present invention. The termination region may be native with the transcriptional initiation region, may be native with the coding sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence.

Generally, the expression cassette will comprise a selectable marker gene for the selection of transformed duckweed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al. (1989) *Plant Physiol.* 91:691; Fromm et al. (1990) *Bio Technology* 8:833; Gordon-Kamm et al. (1990) *Plant Cell* 2:603. For example, resistance to glyphosate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1); cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.*

221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (e.g., aacC1, Wohlleben et al. (1989) *Mol. Gen. Genet.* 217:202-208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) EMBO J. 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes is not meant to be limiting. Any selectable marker gene can be used in the present invention.

Modification of Nucleotide Sequences for Enhanced Expression in a Plant or Microalga Host Where the BTV polypeptide or fragment or variant thereof is expressed within duckweed or microalga, the expressed polynucleotide sequence encoding the BTV polypeptide or fragment or variant thereof can be modified to enhance its expression in duckweed or microalga, respectively. One such modification is the synthesis of the polynucleotide using plant-preferred codons, particularly duckweed-preferred codons, or using microalga-preferred codons, such as *Schizochytrium*-prefered codons. Methods are available in the art for synthesizing nucleotide sequences with plant-preferred codons. See, e.g., U.S. Pat. Nos. 5,380,831 and 5,436,391; EP 0 359 472; EP 0 385 962; WO 91/16432; Perlak et al. (1991) *Proc. Natl. Acad. Sci. USA* 15:3324; Iannacome et al. (1997) *Plant Mol. Biol.* 34:485; and Murray et al. (1989) *Nucleic Acids. Res.* 17:477. Synthesis can be accomplished using any method known to one of skill in the art. The preferred codons may be determined from the codons of highest frequency in the proteins expressed in duckweed or microalga. For example, the frequency of codon usage for *Lemna minor* is found in Table A, the frequency of codon usage for *Schizochytrium* is found in Table B.

TABLE A

*Lemna minor* [gbpln]: 4 CDS's (1597 codons)
fields: [triplet] [frequency: per thousand] ([number])

| | | | | | | | |
|---|---|---|---|---|---|---|---|
| UUU | 17.5 (28) | UCU | 13.8 (22) | UAU | 8.8 (14) | UGU | 5.0 (8) |
| UUC | 36.3 (58) | UCC | 17.5 (28) | UAC | 15.7 (25) | UGC | 14.4 (23) |
| UUA | 5.6 (9) | UCA | 14.4 (23) | UAA | 0.0 (0) | UGA | 1.9 (3) |
| UUG | 13.8 (22) | UCG | 13.8 (22) | UAG | 0.6 (1) | UGG | 16.3 (26) |
| CUU | 15.7 (25) | CCU | 11.9 (19) | CAU | 6.9 (11) | CGU | 4.4 (7) |
| CUC | 25.7 (41) | CCC | 15.7 (25) | CAC | 16.9 (27) | CGC | 18.2 (29) |
| CUA | 5.0 (8) | CCA | 11.3 (18) | CAA | 10.0 (16) | CGA | 6.3 (10) |
| CUG | 21.3 (34) | CCG | 14.4 (23) | CAG | 22.5 (36) | CGG | 10.6 (17) |
| AUU | 18.8 (30) | ACU | 9.4 (15) | AAU | 13.8 (22) | AGU | 10.0 (16) |
| AUC | 19.4 (31) | ACC | 17.5 (28) | AAC | 21.9 (35) | AGC | 15.0 (24) |
| AUA | 1.9 (3) | ACA | 5.0 (8) | AAA | 15.7 (25) | AGA | 20.7 (33) |
| AUG | 20.7 (33) | ACG | 10.0 (16) | AAG | 35.7 (57) | AGG | 17.5 (28) |
| GUU | 15.0 (24) | GCU | 25.0 (40) | GAU | 20.0 (32) | GGU | 8.1 (13) |
| GUC | 25.0 (40) | GCC | 22.5 (36) | GAC | 26.3 (42) | GGC | 21.9 (35) |
| GUA | 6.3 (10) | GCA | 14.4 (23) | GAA | 26.3 (42) | GGA | 16.9 (27) |
| GUG | 30.7 (49) | GCG | 18.2 (29) | GAG | 40.1 (64) | GGG | 18.2 (29) |

TABLE B

*Schizochytrium* sp. ATCC_20888 [gbpln]: 3 CDS's (6473 codons)
fields: [triplet] [frequency: per thousand] ([number])

| | | | | | | | |
|---|---|---|---|---|---|---|---|
| UUU | 12.2 (79) | UCU | 7.0 (45) | UAU | 1.1 (7) | UGU | 0.8 (5) |
| UUC | 19.9 (129) | UCC | 23.8 (154) | UAC | 21.5 (139) | UGC | 15.3 (99) |

TABLE B-continued Schizochytrium sp. ATCC_20888 [gbpln]: 3 CDS's (6473 codons)
fields: [triplet] [frequency: per thousand] ([number])

| | | | | | | | |
|---|---|---|---|---|---|---|---|
| UUA | 0.0 (0) | UCA | 0.5 (3) | UAA | 0.5 (3) | UGA | 0.0 (0) |
| UUG | 0.6 (4) | UCG | 18.8 (122) | UAG | 0.0 (0) | UGG | 8.3 (54) |
| CUU | 12.7 (82) | CCU | 11.7 (76) | CAU | 2.3 (15) | CGU | 7.1 (46) |
| CUC | 61.2 (396) | CCC | 23.8 (154) | CAC | 12.8 (83) | CGC | 42.9 (278) |
| CUA | 0.0 (0) | CCA | 1.5 (10) | CAA | 2.3 (15) | CGA | 0.3 (2) |
| CUG | 7.4 (48) | CCG | 16.2 (105) | CAG | 27.7 (179) | CGG | 0.8 (5) |
| AUU | 13.9 (90) | ACU | 9.1 (59) | AAU | 1.9 (12) | AGU | 1.5 (10) |
| AUC | 33.5 (217) | ACC | 29.2 (189) | AAC | 32.4 (210) | AGC | 15.6 (101) |
| AUA | 0.0 (0) | ACA | 1.5 (10) | AAA | 2.2 (14) | AGA | 0.2 (1) |
| AUG | 27.8 (180) | ACG | 9.6 (62) | AAG | 54.5 (353) | AGG | 0.0 (0) |
| GUU | 8.3 (54) | GCU | 24.4 (158) | GAU | 13.4 (87) | GGU | 13.0 (84) |
| GUC | 53.0 (343) | GCC | 86.0 (557) | GAC | 45.0 (291) | GGC | 54.5 (353) |
| GUA | 0.2 (1) | GCA | 4.0 (26) | GAA | 7.3 (47) | GGA | 3.9 (25) |
| GUG | 14.4 (93) | GCG | 15.9 (103) | GAG | 62.3 (403) | GGG | 0.5 (3) |

For purposes of the present invention, "duckweed-preferred codons" refers to codons that have a frequency of codon usage in duckweed of greater than 17%. "Lemna-preferred codons" as used herein refers to codons that have a frequency of codon usage in the genus *Lemna* of greater than 17%. "*Lemna minor*-preferred codons" as used herein refers to codons that have a frequency of codon usage in *Lemna minor* of greater than 17% where the frequency of codon usage in *Lemna minor* is obtained from the Codon Usage Database (GenBank Release 160.0, Jun. 15, 2007). "Microalgae-preferred codons" refers to codons that have a frequency of codon usage in microalgae of greater than 17%. "microalgae-preferred codons" as used herein refers to codons that have a frequency of codon usage in the family Thraustochytriaceae of greater than 17%. "*Schizochytrium*-preferred codons" as used herein refers to codons that have a frequency of codon usage in *schizochytrium* of greater than 17% where the frequency of codon usage in *schizochytrium* is obtained from the Codon Usage Database.

It is further recognized that all or any part of the polynucleotide encoding the BTV polypeptide of interest, or fragment or variant thereof, may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be duckweed-preferred or microalgae-preferred codons. In one embodiment, between 90 and 96% of the codons are duckweed-preferred or microalgae-preferred codons. The coding sequence of a polynucleotide sequence encoding a BTV polypeptide of interest, or fragment or variant thereof, may comprise codons used with a frequency of at least 17% in *Lemna gibba* or at least 17% in *Lemna minor*. In one embodiment, the BTV polypeptide is a VP2 or VP5 polypeptide, for example, the VP2 polypeptide as set forth in SEQ ID NO:4 or the VP5 polypeptide as set forth in SEQ ID NO:10, and the expression cassette comprises an optimized coding sequence for this VP2 polypeptide, where the coding sequence comprises duckweed-preferred codons, for example, *Lemna minor*-preferred or *Lemna gibba*-preferred codons. In one such embodiment, the expression cassette comprises SEQ ID NO:3, which contains *Lemna minor*-preferred codons encoding the VP2 polypeptide as set forth in SEQ ID NO:4. In another such embodiment, the expression cassette comprises SEQ ID NO:9, which contains *Lemna minor*-preferred codons encoding the VP5 polypeptide as set forth in SEQ ID NO:10.

Other modifications can also be made to the polynucleotide encoding the BTV polypeptide of interest, or fragment or variant thereof, to enhance its expression in duckweed or microalga. These modifications include, but are not limited to, elimination of sequences encoding spurious polyadenylation signals, exon-intron splice site signals, transposon-like repeats, and other such well characterized sequences that may be deleterious to gene expression. The G-C content of the sequence may be adjusted to levels average for duckweed, as calculated by reference to known genes expressed in this plant. When possible, the polynucleotide encoding the heterologous polypeptide of interest may be modified to avoid predicted hairpin secondary mRNA structures.

There are known differences between the optimal translation initiation context nucleotide sequences for translation initiation codons in animals, plants and algae. "Translation initiation context nucleotide sequence" as used herein refers to the identity of the three nucleotides directly 5' of the translation initiation codon. "Translation initiation codon" refers to the codon that initiates the translation of the mRNA transcribed from the nucleotide sequence of interest. The composition of these translation initiation context nucleotide sequences can influence the efficiency of translation initiation. See, for example, Lukaszewicz et al. (2000) *Plant Science* 154:89-98; and Joshi et al. (1997); *Plant Mol. Biol.* 35:993-1001. In the present invention, the translation initiation context nucleotide sequence for the translation initiation codon of the polynucleotide encoding the antigenic BTV polypeptide of interest, or fragment or variant thereof, may be modified to enhance expression in duckweed. In one embodiment, the nucleotide sequence is modified such that the three nucleotides directly upstream of the translation initiation codon are "ACC." In a second embodiment, these nucleotides are "ACA."

Expression of a BTV polypeptide in duckweed or alga can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325: 622); tobacco mosaic virus leader (TMV; Gallie (1989) *Molecular Biology of RNA*, 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) *Virology* 81:382). See also, Della-Cioppa et al. (1987) *Plant Physiology* 84:965. Leader sequence comprising plant intron sequence, including intron sequence from the maize alcohol dehydrogenase 1 (ADH1) gene, the castor bean catalase gene, or the *Arabidopsis* tryptophan pathway gene PAT1 has also been shown to increase translational efficiency in plants (Callis et al. (1987) *Genes Dev.* 1:1183-1200; Mascarenhas et al. (1990) *Plant Mol. Biol.* 15:913-920).

In some embodiments of the present invention, nucleotide sequence corresponding to nucleotides 1222-1775 of the maize alcohol dehydrogenase 1 gene (ADH1; GenBank Accession Number X04049) is inserted upstream of the polynucleotide encoding the BTV polypeptide of interest, or fragment or variant thereof, to enhance the efficiency of its translation. In another embodiment, the expression cassette contains the leader from the *Lemna gibba* ribulose-bis-phosphate carboxylase small subunit 5B gene (RbcS leader; see Buzby et al. (1990) *Plant Cell* 2:805-814).

It is recognized that any of the expression-enhancing nucleotide sequence modifications described above can be used in the present invention, including any single modification or any possible combination of modifications. The phrase "modified for enhanced expression" in duckweed, as used herein, refers to a polynucleotide sequence that contains any one or any combination of these modifications.

Transformed Duckweed Plants and Duckweed Nodule Cultures or Transformed Microalgae The present invention provides transformed duckweed plants expressing a BTV polypeptide of interest, or fragment or variant thereof. The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda, and Wl. neotropica*) and genus *Landoltia* (*L. punctata*). Any other genera or species of Lemnaceae, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* (Geobatanischen Institut ETH, Stiftung Rubel, Zurich).

As used herein, "plant" includes whole plants, plant organs (e.g., fronds (leaves), stems, roots, etc.), seeds, plant cells, and progeny of same. Parts of transgenic plants are to be understood within the scope of the invention to comprise, e.g., plant cells, plant protoplasts, plant cell tissue cultures from which plants can be regenerated, tissues, plant calli, embryos as well as flowers, ovules, stems, fruits, leaves, roots, root tips, nodules, and the like originating in transgenic plants or their progeny previously transformed with a polynucleotide of interest and therefore consisting at least in part of transgenic cells. As used herein, the term "plant cell" includes cells of seeds, embryos, ovules, meristematic regions, callus tissue, leaves, fronds, roots, nodules, shoots, anthers, and pollen.

As used herein, "duckweed nodule" means duckweed tissue comprising duckweed cells where at least about 50%, 55%, 60%, 65%, 70%, 75%, 80%, 85%, 90%, 95% or 100% of the cells are differentiated cells. As used herein, "differentiated cell," means a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connected to each other via plasmadesmata.

The growth habit of the duckweeds is ideal for culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20-24 hours (Landolt (1957) *Ber. Schweiz. Bot. Ges.* 67:271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62: 316). Intensive culture of duckweed results in the highest rates of biomass accumulation per unit time (Landolt and Kandeler (1987) *The Family of Lemnaceae—A Monographic Study Vol. 2: Phytochemistry, Physiology, Application, Bibliography* (Veroffentlichungen des Geobotanischen Institutes ETH, Stiftung Rubel, Zurich)), with dry weight accumulation ranging from 6-15% of fresh weight (Tillberg et al. (1979) *Physiol. Plant.* 46:5; Landolt (1957) *Ber. Schweiz. Bot. Ges.* 67:271; Stomp, unpublished data). Protein content of a number of duckweed species grown under varying conditions has been reported to range from 15-45% dry weight (Chang et al. (1977) *Bull. Inst. Chem. Acad. Sin.* 24:19; Chang and Chui (1978) *Z. Pflanzenphysiol.* 89:91; Porath et al. (1979) *Aquatic Botany* 7:272; Appenroth et al. (1982) *Biochem. Physiol. Pflanz.* 177:251). Using these values, the level of protein production per liter of medium in duckweed is on the same order of magnitude as yeast gene expression systems.

The present invention also provides transformed microalgae plants expressing a BTV polypeptide of interest, or fragment or variant thereof. The term "microalgae" or "microalga" refers to members of the family Thraustochytriaceae. This family currently is divided into four genera: *Schizochytrium, Thraustochytrium, Labyrinthuloides*, and *Japonochytrium*.

The transformed duckweed plants or microalgae of the invention can be obtained by introducing an expression construct comprising a polynucleotide encoding a BTV polypeptide, or fragment or variant thereof, into the duckweed plant or microalga of interest.

The term "introducing" in the context of a polynucleotide, for example, an expression construct comprising a polynucleotide encoding a BTV polypeptide, or fragment or variant thereof, is intended to mean presenting to the duckweed plant or microalga the polynucleotide in such a manner that the polynucleotide gains access to the interior of a cell of the duckweed plant or microalga. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the duckweed or microalga host cell of interest in a single transformation event, in separate transformation events, or, for example, as part of a breeding protocol. The compositions and methods of the invention do not depend on a particular method for introducing one or more polynucleotides into a duckweed plant or microalga, only that the polynucleotide(s) gains access to the interior of at least one cell of the duckweed plant or microalga. Methods for introducing polynucleotides into plants or algae are known in the art including, but not limited to, transient transformation methods, stable transformation methods, and virus-mediated methods.

"Transient transformation" in the context of a polynucleotide such as a polynucleotide encoding a BTV polypeptide, or fragment or variant thereof, is intended to mean that a polynucleotide is introduced into the duckweed plant or microalga and does not integrate into the genome of the duckweed plant or microalga.

By "stably introducing" or "stably introduced" in the context of a polynucleotide (such as a polynucleotide encoding a BTV polypeptide, or fragment or variant thereof) introduced into a duckweed plant or microalga is intended the introduced polynucleotide is stably incorporated into the duckweed or microalga genome, and thus the duckweed plant or microalga is stably transformed with the polynucleotide.

"Stable transformation" or "stably transformed" is intended to mean that a polynucleotide, for example, a polynucleotide encoding a BTV polypeptide, or fragment or variant thereof, introduced into a duckweed plant or microalga integrates into the genome of the plant or alga and is capable of being inherited by the progeny thereof, more particularly, by the progeny of multiple successive generations. In some embodiments, successive generations include progeny produced vegetatively (i.e., asexual reproduction), for example, with clonal propagation. In other embodiments, successive generations include progeny produced via sexual reproduction.

An expression construct comprising a polynucleotide encoding a BTV polypeptide, or fragment or variant thereof, can be introduced into a duckweed plant or microalga of interest using any transformation protocol known to those of skill in art. Suitable methods of introducing nucleotide sequences into duckweed plants or plant cells or nodules or microalgae include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563,055 and 5,981,840, both of which are herein incorporated by reference), direct gene transfer (Paszkowski et al. (1984) *EMBO J.* 3:2717-2722), ballistic particle acceleration (see, e.g., U.S. Pat. Nos. 4,945,050; 5,879,918; 5,886,244; and 5,932,782 (each of which is herein incorporated by reference); and Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926). The cells that have been transformed may be grown into plants in accordance with conventional ways.

As noted above, stably transformed duckweed or microalgae can be obtained by any gene transfer method known in the art, such as one of the gene transfer methods disclosed in U.S. Pat. No. 6,040,498 or U.S. Patent Application Publication Nos. 2003/0115640, 2003/0033630 or 2002/0088027. Duckweed plant or nodule cultures or microalga can be efficiently transformed with an expression cassette containing a nucleic acid sequence as described herein by any one of a number of methods including *Agrobacterium*-mediated gene transfer, ballistic bombardment or electroporation. The *Agrobacterium* used can be *Agrobacterium tumefaciens* or *Agrobacterium rhizogenes*. Stable duckweed or microalga transformants can be isolated by transforming the duckweed or microalga cells with both the nucleic acid sequence of interest and a gene that confers resistance to a selection agent, followed by culturing the transformed cells in a medium containing the selection agent. See, for example, U.S. Pat. No. 6,040,498, the contents of which are herein incorporated by reference in their entirety.

The stably transformed duckweed plants or microalgae utilized in these methods should exhibit normal morphology and be fertile by sexual reproduction and/or able to reproduce vegetatively (i.e., asexual reproduction), for example, with clonal propagation. Preferably, transformed duckweed plants or microalgae of the present invention contain a single copy of the transferred nucleic acid comprising a polynucleotide encoding a BTV polypeptide, or fragment or variant thereof, and the transferred nucleic acid has no notable rearrangements therein. It is recognized that the transformed duckweed plants or microalgae of the invention may contain the transferred nucleic acid present in low copy numbers (i.e., no more than twelve copies, no more than eight copies, no more than five copies, alternatively, no more than three copies, as a further alternative, fewer than three copies of the nucleic acid per transformed cell).

Transformed plants or microalgae expressing a BTV polypeptide, or fragment or variant thereof, can be cultured under suitable conditions for expressing the antigenic BTV polypeptide, or fragment or variant thereof. The BTV polypeptide, or fragment or variant thereof, can then be harvested from the duckweed plant or microalgae, the culture medium, or the duckweed plant or microalgae and the culture medium, and, where desired, purified using any conventional isolation and purification method known in the art, as described elsewhere herein. The antigenic BTV polypeptide, or fragment or variant thereof, can then be formulated as a vaccine for therapeutic applications, as described elsewhere herein.

Methods of Preparing a BTV Polypeptide

As described fully herein, in an embodiment, a method of producing a BTV polypeptide comprises: (a) culturing within a duckweed culture medium a duckweed plant or duckweed nodule, wherein the duckweed plant or duckweed nodule is stably transformed to express the polypeptide, and wherein the polypeptide is expressed from a nucleotide sequence comprising a coding sequence for said polypeptide; and (b) collecting the antigenic polypeptide from said duckweed plant or duckweed nodule. The term collecting includes, but is not limited to, harvesting from the culture medium or purifying.

After production of the recombinant polypeptide in duckweed or microalgae, any method available in the art may be used for protein purification. The various steps include freeing the protein from the nonprotein or plant or microalga material, followed by the purification of the protein of interest from other proteins. Initial steps in the purification process include centrifugation, filtration or a combination thereof. Proteins secreted within the extracellular space of tissues can be obtained using vacuum or centrifugal extraction. Minimal processing could also involve preparation of crude products. Other methods include maceration and extraction in order to permit the direct use of the extract.

Such methods to purify the protein of interest can exploit differences in protein size, physio-chemical properties, and binding affinity. Such methods include chromatography, including procainamide affinity, size exclusion, high pressure liquid, reversed-phase, and anion-exchange chromatography, affinity tags, filtration, etc. In particular, immobilized Ni-ion affinity chromatography can be used to purify the expressed protein. See, Favacho et al. (2006) Protein expression and purification 46:196-203. See also, Zhou et al. (2007) The Protein J 26:29-37; Wang et al. (2006) Vaccine 15:2176-2185; and WO/2009/076778. Protectants may be used in the purification process such as osmotica, antioxidants, phenolic oxidation inhibitors, protease inhibitors, and the like.

Methods of Use

In an embodiment, the subject matter disclosed herein is directed to a method of vaccinating an ovine, bovine, or caprine comprising administering to the ovine, bovine, or caprine an effective amount of a vaccine which may comprise an effective amount of a recombinant BTV polypeptide or antigen and a pharmaceutically or veterinarily acceptable carrier, excipient, adjuvant, or vehicle.

In one embodiment of the present invention, the method comprises a single administration of a vaccine composition formulated with an emulsion or a classical crystalline salt according to the invention. In an embodiment, the subject matter disclosed herein is directed to a method of vaccinating an ovine, bovine, or caprine comprising administering to the ovine, bovine, or caprine the BTV polypeptide or antigen produced in a plant or alga, and plant material from the genus *Lemna* or microalga material from *schizochytrium*.

In an embodiment, the subject matter disclosed herein is directed to a method of eliciting an immune response comprising administering to the ovine, bovine, or caprine a vaccine comprising the BTV polypeptide or antigen expressed in a plant or alga, wherein an immune response is elicited.

In an embodiment, the subject matter disclosed herein is directed to a method of preparing a stably transformed duckweed plant comprising, (a) introducing into the plant a genetic construct comprising a BTV antigen gene; and (b) cultivating the plant. Methods for transformation of duckweed are available in the art.

In an embodiment, the subject matter disclosed herein is directed to a method of preparing a vaccine or composition comprising isolating a BTV antigen produced by a duckweed or microalgal expression system and optionally combining with a pharmaceutically or veterinarily acceptable carrier, excipient, adjuvant, or vehicle.

In an embodiment, the subject matter disclosed herein is directed to a method of preparing a vaccine or composition comprising combining a BTV antigen produced by a *Lemna* expression system and plant material from the genus *Lemna* and optionally a pharmaceutically or veterinarily acceptable carrier, excipient, adjuvant, or vehicle.

In another embodiment, the subject matter disclosed herein is directed to a method of preparing a vaccine or composition comprising combining a BTV antigen produced by a *Schizochytrium* expression system and *Schizochytrium* material and optionally a pharmaceutically or veterinarily acceptable carrier, excipient, adjuvant, or vehicle.

The administering may be subcutaneously or intramuscularly. The administering may be needle free (for example Pigjet or Bioject).

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the boost. This administration protocol is called "prime-boost".

A prime-boost according to the present invention can include a recombinant viral vector used to express a BTV coding sequence or fragments thereof. Specifically, the viral vector can express a BTV gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, laryngotracheitis virus (ILTV), bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The BTV antigen of the invention to be expressed is inserted under the control of a specific poxvirus promoter, e.g., the entomopoxvirus *Amsacta moorei* 42K promoter (Barcena, Lorenzo et al. 2000), the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In another embodiment, the avipox expression vector may be a canarypox vector, such as, ALVAC. The BTV polypeptide, antigen, epitope or immunogen may be a BTV VP2 or BTV VP5. The viral vector may be vCP2289, which encodes BTV codon-optimized synthetic VP2 and VP5 (see US 2007/0280960).

In another aspect of the prime-boost protocol of the invention, a composition comprising the BTV antigen of the invention is administered followed by the administration of vaccine or composition comprising a recombinant viral vector that contains and expresses the BTV antigen in vivo, or an inactivated viral vaccine or composition comprising the BTV antigen, or a DNA plasmid vaccine or composition that contains or expresses the BTV antigen. Likewise, a prime-boost protocol may comprise the administration of vaccine or composition comprising a recombinant viral vector that contains and expresses a BTV antigen in vivo, or an inactivated viral vaccine or composition comprising a BTV antigen, or a DNA plasmid vaccine or composition that contains or expresses a BTV antigen, followed by the administration of a composition comprising the BTV antigen of the invention. It is further noted that both the primary and the secondary administrations may comprise the composition comprising the BTV antigen of the invention A prime-boost protocol comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of ovine, bovine, or caprine compositions, based on viral vectors, e.g., non-poxvirus-viral-vector-based compositions, is generally between about 0.1 to about 5.0 ml, between about 0.1 to about 3.0 ml, and between about 0.5 ml to about 2.5 ml.

The efficacy of the vaccines may be tested about 2 to 4 weeks after the last immunization by challenging animals, such as ovine, bovine, or caprine, with a virulent strain of BTV, such as the BTV-1/2/3/4/8/9/16 or 17 strains. For example, the BTV strain may be serotype 17, which was originally isolated from the blood of sheep from Tulare County, Calif. (see Bonneau, DeMaula et al. 2002; DeMaula, Leutenegger et al. 2002). The BTV strain may also be serotype 8, an inactivated vaccine for which is currently available from Merial Limited.

Other strains may include BTV1 (isolate French), BTV1 (isolate Australia), BTV1 (isolate South Africa), BTV2 (isolate USA), BTV3 (isolate South Africa), BTV4-9, BTV10 (isolate USA), BTV11 (isolate USA), BTV12, BTV13 (isolate USA), BTV14-17, BTV17 (isolate USA), BTV18, BTV19, BTV20 (isolate Australia), BTV21-24, or Corsican BTV.

Both homologous and heterologous strains are used for challenge to test the efficacy of the vaccine. The animal may be challenged intradermally, subcutaneously, spray, intra-nasally, intra-ocularly, intra-tracheally, and/or orally.

For BTV, bovines and caprines are evaluated for extensive vascular injury. Also for BTV, ovines are evaluated for catarrhal inflammation of the mucous membranes of the mouth, nose and forestomachs, inflammation of the coronary bands and laminae of the hoofs, excoriation of the epithelium, necrosis of the buccal mucosa, and swollen/inflamed/blue tongue and mouth. Swabs may be collected from all animals post challenge for virus isolation. The presence or absence of viral antigens in the above-indicated tissues may be evaluated by quantitative real time reverse transcriptase polymerase chain reaction (qRRT-PCR). Blood samples may be collected before and post-challenge and may be analyzed for the presence of anti-BTV specific antibody.

The prime-boost administrations may be advantageously carried out 2 to 6 weeks apart, for example, about 3 weeks apart. According to one embodiment, a semi-annual booster or an annual booster, advantageously using the viral vector-based vaccine, is also envisaged. The animals are advantageously at least 6 to 8 weeks old at the time of the first administration.

The compositions comprising the recombinant antigenic polypeptides of the invention used in the prime-boost protocols are contained in a pharmaceutically or veterinary acceptable vehicle, diluent, adjuvant, or excipient. The protocols of the invention protect the animal from ovine, bovine, or caprine BTV and/or prevent disease progression in an infected animal.

The various administrations are preferably carried out 1 to 6 weeks apart, and more particularly about 3 weeks apart. According to a preferred mode, an annual booster, preferably using the viral vector-based immunological composition of vaccine, is also envisaged. The animals are preferably at least one-day-old at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment.

In one embodiment, the invention provides for the administration of a therapeutically effective amount of a formulation for the delivery and expression of a BTV antigen or epitope in a target cell. Determination of the therapeutically effective amount is routine experimentation for one of ordinary skill in the art. In one embodiment, the formulation comprises an expression vector comprising a polynucleotide that expresses a BTV antigen or epitope and a pharmaceutically or veterinarily acceptable carrier, vehicle or excipient. In another embodiment, the pharmaceutically or veterinarily acceptable carrier, vehicle or excipient facilitates transfection or other means of transfer of polynucleotides to a host animal and/or improves preservation of the vector or protein in a host.

In one embodiment, the subject matter disclosed herein provides a detection method for differentiation between infected and vaccinated animals (DIVA).

Currently, there are several available BTV vaccines. Merial offers inactivated BTV1 and BTV8 vaccines. Intervet offers inactivated BTV8 vaccines. Pfizer offers inactivated BTV1, BTV4 and BTV8 vaccines. A method to distinguish between BTV-vaccinated and BTV-infected animals has recently been described (Anderson, J et al, J. Virol. Methods, 1993; Silvia C. Banos et al., Veterinary-Microbiology, 2009).

It is disclosed herein that the use of the vaccine or composition of the present invention allows the detection of BTV infection in an animal. It is disclosed herein that the use of the vaccine or composition of the present invention allows the detection of the infection in animals by differentiating between infected and vaccinated animals (DIVA). Diagonostic tests based on non-structural proteins, such as indirect NS3-ELISA and competitive ELISA using monoclonal antibody against NS1, have been developed. However, the inactivated vaccines may still induce low levels of antibodies against non-structual proteins if the vaccines are not sufficiently purified. This limitation will be overcome by the present invention expressing only outer capsid proteins VP2 and VP5.

Article of Manufacture

In an embodiment, the subject matter disclosed herein is directed to a kit for performing a method of eliciting or inducing an immune response which may comprise any one of the recombinant BTV immunological compositions or vaccines, or inactivated BTV immunological compositions or vaccines, recombinant BTV viral compositions or vaccines, and instructions for performing the method.

Another embodiment of the invention is a kit for performing a method of inducing an immunological or protective response against BTV in an animal comprising a composition or vaccine comprising a BTV antigen of the invention and a recombinant BTV viral immunological composition or vaccine, and instructions for performing the method of delivery in an effective amount for eliciting an immune response in the animal.

Another embodiment of the invention is a kit for performing a method of inducing an immunological or protective response against BTV in an animal comprising a composition or vaccine comprising a BTV antigen of the invention and an inactivated BTV immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional primo-vaccinations or additional boost-vaccinations.

The following embodiments are encompassed by the invention. In an embodiment, a composition comprising a BTV antigen or fragment or variant thereof and a pharmaceutical or veterinarily acceptable carrier, excipient, or vehicle is disclosed. In another embodiment, the composition described above wherein the BTV antigen or fragment or variant thereof comprises an immunogenic fragment comprising at least 15 amino acids of an ovine, bovine, or caprine BTV antigen is disclosed. In yet another embodiment, the above compositions wherein the BTV antigen or fragment or variant thereof is produced in duckweed or microalgae are disclosed. In an embodiment, the above compositions wherein the BTV antigen or fragment or variant thereof is partially purified are disclosed. In an embodiment, the above compositions wherein the BTV antigen or fragment or variant thereof is substantially purified are disclosed. In an embodiment, the above compositions wherein the BTV antigen or fragment or variant thereof is a BTV1 polypeptide are disclosed. In an embodiment, the above compositions wherein the BTV1 polypeptide is a VP2 or VP5 polypeptide are disclosed. In an embodiment, the above compositions wherein the BTV antigen or fragment or variant thereof has at least 80% sequence identity to the sequence as set forth in SEQ ID NO: 4, 6, 10, 11, 12, 13, 14, 15, 16, 17, 18, 19, 20, 21, 22, 23, 24, or 25 are disclosed. In one embodiment, the above compositions wherein the BTV antigen is encoded by a polynucleotide having at least 70% sequence identity to the sequence as set forth in SEQ ID NO: 1, 2, 3, 5, 7, 8, or 9 are disclosed.

In an embodiment, the above compositions wherein the pharmaceutical or veterinarily acceptable carrier, excipient, adjuvant, or vehicle is a water-in-oil emulsion or an oil-in-water emulsion are disclosed. In another embodiment, a method of vaccinating an animal susceptible to ovine, bovine, or caprine BTV comprising administering the compositions above to the animal is disclosed. In an embodiment, a method of vaccinating an animal susceptible to ovine, bovine, or caprine BTV comprising a prime-boost regime is disclosed. In an embodiment, a substantially purified antigenic polypeptide expressed in duckweed or microalga, wherein the polypeptide comprises: an amino acid sequence having at least 80% sequence identity to a polypeptide having the sequence as set forth in SEQ ID NO: 4, 6, 10, 11, 12, 13, 14, 15, 16, 17, 18, 19, 20, 21, 22, 23, 24, or 25 is disclosed. In any embodiment the animal is preferably an ovine, a bovine, or a caprine. In one embodiment, a method of diagnosing BTV infection in an animal is disclosed. In yet another embodiment, a kit for prime-boost vaccination comprising at least two vials, wherein a first vial containing the composition of the present invention, and a second vial containing a composition for the boost-vaccination comprising a composition comprising a recombinant viral vector, or a composition comprising an inactivated viral composition, or a DNA plasmid composition that contains or expresses the BTV antigen is disclosed.

The pharmaceutically or veterinarily acceptable carriers, vehicles, adjuvants, or excipients are well known to the one skilled in the art. For example, a pharmaceutically or veterinarily acceptable carrier, vehicle, adjuvant, or excipient can be a 0.9% NaCl (e.g., saline) solution or a phosphate buffer. Other pharmaceutically or veterinarily acceptable carrier, vehicle, adjuvant, or excipients that can be used for methods of this invention include, but are not limited to, poly-(L-glutamate) or polyvinylpyrrolidone. The pharmaceutically or veterinarily acceptable carrier, vehicle, adjuvant, or excipients may be any compound or combination of compounds facilitating the administration of the vector (or protein expressed from an inventive vector in vitro); advantageously, the carrier, vehicle, adjuvant, or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH(OR_1)-CH_2-\overset{+}{N}(CH_3)(CH_3)-R_2-X$$

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

In another embodiment, pharmaceutically or veterinarily acceptable carrier, excipient, vehicle or adjuvant may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly) ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084, e.g., Example 8. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more pharmaceutically or veterinarily acceptable carrier, excipient, vehicle, or adjuvant. Suitable carriers or adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

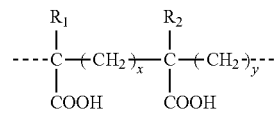

in which:
R1 and R2, which can be the same or different, represent H or CH3
x=0 or 1, preferably x=1
y=1 or 2, with x+y=2.
For EMA, x=0 and y=2 and for carbomers x=y=1.
These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a bovine cytokine for preparations to be administered to bovines).

Advantageously, the immunological composition and/or vaccine according to the invention comprise or consist essentially of or consist of an effective quantity to elicit a therapeutic response of one or more polypeptides as discussed herein; and, an effective quantity can be determined from this disclosure, including the documents incorporated herein, and the knowledge in the art, without undue experimentation.

In the case of immunological composition and/or vaccine based on the expressed polypeptides, a dose may include, about in 1 μg to about 2000 μg, advantageously about 50 μg to about 1000 μg and more advantageously from about 100 μg to about 500 μg of BTV antigen, epitope or immunogen. The dose volumes can be between about 0.1 and about 10 ml, advantageously between about 0.2 and about 5 ml.

The invention will now be further described by way of the following non-limiting examples.

EXAMPLES

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of BTV1 VP5 Expression Plasmid pCG102, BTV1 VP2 Expression Plasmid pCG100, and BTV1 VP2+c-Myc Expression Plasmid pCG101

The objective of these experiments is to produce pVR1012-based plasmid constructs containing the VP2 or VP5 gene from BTV serotype 1 and verify the expression in CHO-transfected cells. Details of pVR1012 may be found, for example, in VICAL Inc.; Luke et al., 1997; Hartikka et al., 1996; U.S. Pat. Nos. 5,846,946 and 6,451,769. These experiments were designed to produce appropriate controls to optimize detection/quantification of Duckweed-expressed BTV antigens.

The BTV1 VP2 ORF optimized for mammalian expression (SEQ ID NO:2), BTV1 VP2 optimized for mammalian expression containing c-myc tag (SEQ ID NO:5), and BTV1 VP5 ORF optimized for mammalian expression (SEQ ID NO:8) were cloned into plasmid pVR1012 using the EcoRV and XbaI sites of both the vector and insert to produce pCG100, pCG101, and pCG102, respectively. The in vitro expression of the BTV1 VP2 protein (SEQ ID NO:4) and BTV1 VP5 protein (SEQ ID NO:10) was measured after transient transfection of CHO-K1 cells, using Lipofectamine 2000 (Invitrogen, Carlsbad Calif.). CHO-K1 at 90% confluency in 6 cm diameter plates were transfected with 5 μg plasmid and 10 μl Lipofectamine each, according to manufacturer's instructions. After transfection, cells were cultivated in MEM-glutamaxmedium (Invitrogen, Carlsbad Calif.) containing 1% SVF for 24 hours. Culture supernatants were harvested and concentrated 50 times by TCA precipitation of proteins. Cells were washed with PBS, harvested by scraping, and lysed using Laemmli SDS-PAGE loading buffer. Recombinant protein production and secretion were analyzed by submitting whole cell extracts and concentrated (50×) culture supernatants to SDS-PAGE and western blotting either rabbit polyclonal antibody against VP2 protein (GENOVAC, Freiburg, Germany) or monoclonal antibody against VP5 protein (10AE12, Ingenasa, Spain).

The epitope of the monoclonal antibody used for the expression analysis (antibody AHSV10AE12 provided from Ingenasa, Spain) was mapped within amino acids 85 to 92 of VP5 protein, a highly conserved region among different orbiviruses as African Horse Sickness Virus (AHSV), Bluetongue Virus (BTV) and Epizootic haemorrhagic disease virus (EHDV) (Martinez-Torrecuadrada et al. Virology, 257, 449-459; 1999). These epitope mapping results suggested that the monoclonal antibody can be used as a group specific reagent, and our results indicated that this observation was correct. The secondary antibody was anti-mouse IRDye800 at a dilution of 1/10000.

Figure 8C:
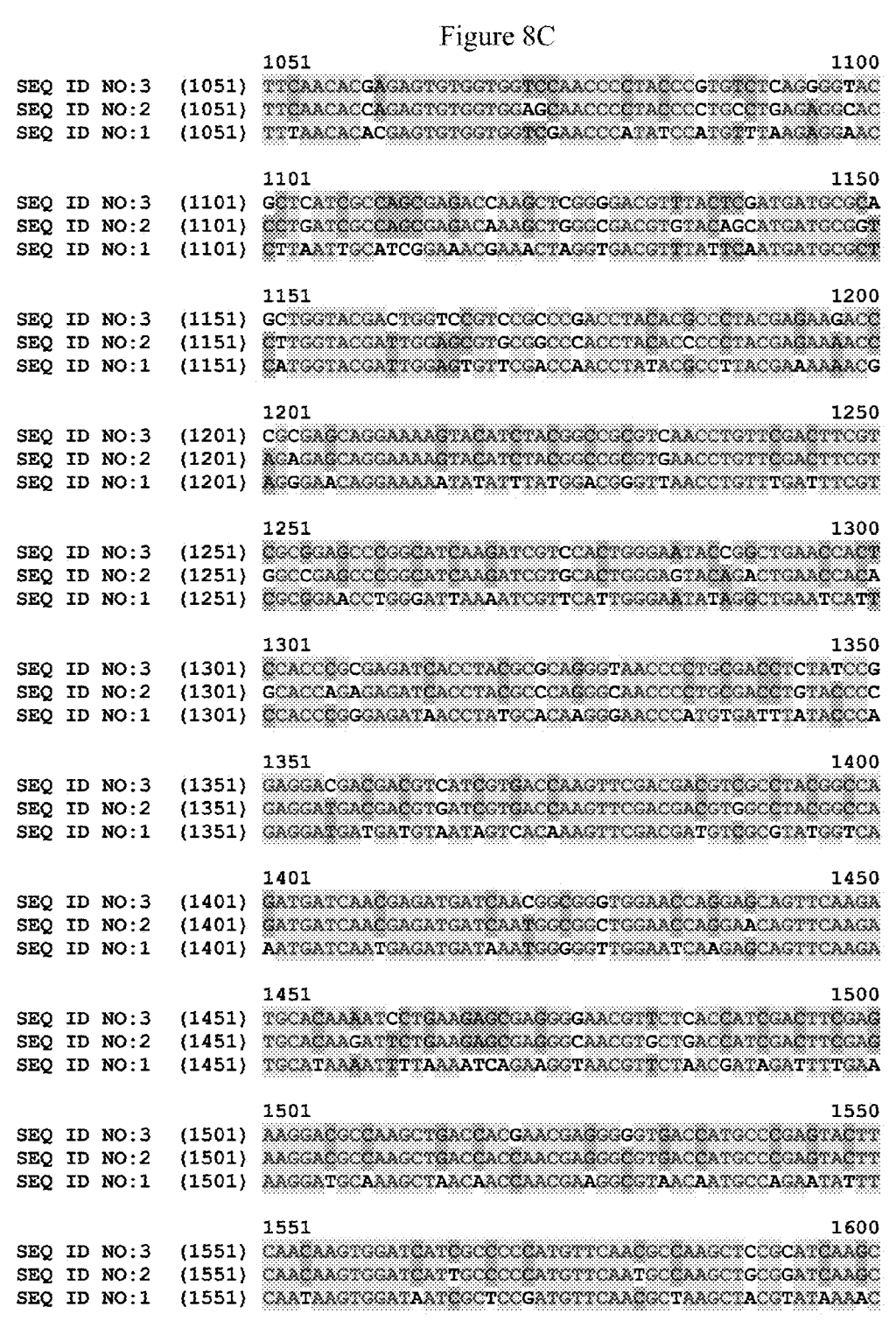

As shown in FIG. 5, BTV1 VP5 is specifically detected in the pCG102-transfected CHO cell fraction, but not the supernatant, by the AHSV10AE12 antibody. FIGS. 7 and 8 show the Western blot results for Pab L167 and Pab L168 on the VP2 from different BTV serotypes. Lane assignments were 1) marker, 2) pVR1012, 3) pCG100 (VP2 BTV1), 4) pIV001 (VP2 BTV2), 5) pIV002 (VP2 BTV4), 6) pKMR003 (VP2 BTV8), 7) pCG030 (VP2 BTV9), and 8) pIV003 (VP2 BTV16).

Example 2

Construction of BTV Duckweed Expression Vectors and Transformation of Plants

Duckweed-optimized BTV VP2 (SEQ ID NO:3) and BTV VP5 (SEQ ID NO:9) genes from the pathogenic BTV1 isolate were expressed using Biolex's LEX System™, a proprietary *Lemna minor* protein system. As shown in FIGS. 10, 11, 12, 13, and 14, several variants were produced, including vectors that express both VP2 and VP5 (MerD01 & MerD02) and vectors that express only VP2 (MerD03 & MerD04).

Transgenic lines were generated for screening (Table 2). After the transgenic lines were generated, they were screened for expression of BTV in the media and the tissue. In brief, the plants were grown for two weeks in small research vessels and the resulting media and tissue were collected for analysis. For the tissue analysis, frozen tissue was homogenized, centrifuged and the supernatant was removed for assay.

Crude tissue extraction from a line containing BTV antigens was prepared. All steps were taken place at 4° C. One hundred grams of frozen biomass (plant material harvested from the media) was mixed with 200 ml extraction buffer (50 mM NaPO$_4$, 0.3M NaCl, 10 mm EDTA, pH 7.4) and then homogenized in a Waring Blender with a 20 second burst for 4 times and 10-20 seconds cooling in between. The homogenate was centrifuged at 10,000×g for 30 min at 4° C., clarified by filtration through a cellulose acetate filter (0.22 μm). The resulting homogenate was stored at 4° C. or on ice for immediate testing. The remaining homogenate was frozen in aliquots at −80° C. for further analysis. Total soluble protein (TSP) was determined using the Bradford assay with bovine serum albumin as a standard.

Four Duckweed-BTV1 expressing lines were selected for scale-up after the initial screening step. Lines that expressed higher levels of VP2 were selected as the VP2 protein/antigen is considered to contribute significantly to the protective immune effect of vaccine compositions containing said protein/antigen. The highest duckweed optimized VP2-expressing lines as determined by western blot for BTV were grown in scale vessels to provide biomass for use in characterization and animal studies.

TABLE 2

BTV expressing Duckweed cell line generation and screening.

| Construct | Description | # of lines generated | # of lines screened |
|---|---|---|---|
| MerD01 | VP2 + VP5 | 188 | 114 |
| MerD02 | VP2 (Optimized 5' UTR) + VP5 | 159 | 54 |
| MerD03 | VP2 | 299 | 184 |
| MerD04 | VP2 (Optimized 5' UTR) | 134 | 56 |

Western blotting was used to determine the molecular weight (MW) of the Duckweed-expressed BTV antigens. See also US Patent Application Publication US2004/261148 for detailed description of preparation of recombinantly expressed polypeptides/antigens from Duckweed. Briefly, 100 mg of frozen plant tissue was homogenized in 1 ml of extraction buffer (1:10 ratio, w/v), centrifuged and the supernatant was removed for assay. The extraction buffer was 50 mM $NaPO_4$, 0.3M NaCl, 10 mm EDTA, pH 7.4. The 1.0% TWEEN 80, the 10% glycerol, and the 1.0% TWEEN 80/10% Glycerol buffers were obtained by adding the appropriate amounts of TWEEN 80 and/or glycerol to the standard extraction buffer. The extracted sample was mixed in SDS buffer immediately after extraction and then followed by 2 hour incubation on ice, followed by SDS buffer, 4 hour incubation on ice, followed by SDS buffer, 1×, 2×, and 3× freeze-thaw followed by SDS buffer. The samples were then resolved on 4-20% Tris-glycine gels under reducing conditions.

It was determined that 10% glycerol should be added to the extraction buffer when assaying VP5 protein. According to the data, aggregation of VP5 protein was likely and quantification using western blot likely underestimated the amount of VP5 protein present in the sample (i.e. since protein is not well separated on the gel, the residual aggregates are undetected). A VP5 monoclonal antibody clone #10AE12 was used in the Western blot for VP5 expression detection. The Western results are shown in FIG. 18.

VP2 antigen was quantified using both SDS/PAGE Coomassie densitometry (Table 3) and Agilent 2100 Bioanalyzer methods (Table 4). For Coomassie densitometry, the density of VP2 antigen bands on a standard Coomassie-stained SDS/PAGE gel was compared to a Bovine Serum Albumin (BSA) standard. The comparative densitometry then results in a VP2 protein concentration. The quantified SDS/Coomassie densitometry results are shown in Table 3.

TABLE 3

SDS/Coomassie Densitometry Results.

| Construct | SV | Description | Antigen Concentration (µg/ml) | % TSP |
|---|---|---|---|---|
| MerD01 | 53A | VP2 + VP5 | 78.2 | 3.36 |
| MerD02 | 3K | VP2 (Optimized 5' UTR) + VP5 | 48.1 | 2.72 |
| MerD03 | 80A | VP2 | 52.7 | 2.82 |
| MerD04 | 11D | VP2 (Optimized 5' UTR) | 65.8 | 2.82 |

In addition to SDS-PAGE Coomassie densitometry, BTV VP2 was quantified using the Agilent 2100 Bioanalyzer. This instrument is a chip-based system designed for measuring the size and quantifying proteins. Measurement was accomplished by comparing MW and band intensity to a standard protein ladder supplied by the manufacturer. The results are shown in Table 4.

TABLE 4

Expression Level of Duckweed-BTV1 VP2 Lines

| Duckweed line | Average VP2 Antigen Conc. (µg/ml) | Average % TSP [1, 2] |
|---|---|---|
| MerD01 | 69.4 | 1.78 |
| MerD02 | 59.0 | 3.16 |
| MerD03 | 56.3 | 3.49 |
| MerD04 | 60.2 | 2.67 |

[1] The Agilent Bioanalyzer 2100 documentation indicates +/−10% error.
[2] Average Total Soluble Protein was between 1.8 and 2.1 mg/ml.

Based on these results, all four of the Duckweed-BTV1 lines express VP2 antigen at a level near or above the 50 µg/ml target.

Example 3

Vaccination of Sheep

The vaccines/formulations to be tested are shown in Table 5 below.

TABLE 5

| Name | Vaccine dose | Antigen | Adjuvant |
|---|---|---|---|
| BTVPUR AlSap1* | 1 mL | Commercial BTV1 antigen | Aluminium hydroxide/ Saponin[1] |
| BTV-Duckweed 1 | 1.2 mL | Crude BTV1 VP2/VP5 (~50 µg) | Aluminium hydroxide/ Saponin |
| BTV-Duckweed 2 | 1.2 mL | Concentrated BTV1 VP2/VP5 (~200 µg) | Aluminium hydroxide/ Saponin |
| BTV-Duckweed 3 | 1.2 mL | Crude BTV1 VP2/VP5 (~50 µg) | Emulsigen/ CpG[2] |
| BTV-Duckweed 4 | 1.2 mL | Concentrated BTV1 VP2/VP5 (~200 µg) | Emulsigen/ CpG |

BTVPUR AlSap1*: commercial BTV vaccine containing inactivated BTV1 virus.
Aluminium hydroxide/Saponin[1]: a type of crystalline salt adjuvant.
Emulsigen/CpG[2]: EMULSIGEN ® is a commercial oil-in-water adjuvant.

Thirty-one female and male sheep between 4 and 6 months of age at D0 were used in the vaccination experiment. On D2, the 31 sheep were individually weighed and then randomly allocated to 5 groups of 5 sheep (G1 to G5) and 1 group of 6 sheep (G6). On D0 and D21, animals from group G1 received one dose of 1 mL of the commercial vaccine BTVPUR AlSap1 and served as positive control animals. Each animal from Groups G2, G3, G4 and G5 received one dose of 1.2 mL of the BTV-duckweed composition as described in Table 6. The animals from group G6 remained untreated and served as negative control animals. Vaccine injections were performed by sub-cutaneous route on the right lateral face of the thorax beside the elbow on D0, and on the left lateral face of the thorax on D21.

TABLE 6

| Group | Number of sheep | Treatment received D 0 | D 21 | BTV1* challenge on D 42 |
|---|---|---|---|---|
| G1 | 5 | BTVPUR AlSap1 | BTVPUR AlSap1 | Yes |
| G2 | 5 | BTV-Duckweed 1 | BTV-Duckweed 1 | Yes |
| G3 | 5 | BTV-Duckweed 2 | BTV-Duckweed 2 | Yes |
| G4 | 5 | BTV-Duckweed 3 | BTV-Duckweed 3 | Yes |
| G5 | 5 | BTV-Duckweed 4 | BTV-Duckweed 4 | Yes |
| G6 | 6 | none | none | Yes |

BTV1* challenge material consists of red blood cells (RBC) collected on infected sheep and stored at −70° C.

Example 4

Antibody Titration by Serum Neutralization

On D-29, before the beginning of the study, all sheep were negative against BTV based on ELISA titration and were thus included. Their negative serological status was confirmed on D0 before vaccination by SN (serumneutralization) test. The mean antibody titres (SN test) for each treatment group throughout the study are shown in FIG. 25.

Blood tests were performed after each rectal temperature was taken. At day 0 (before the 1st immunization), D21 (before the 2nd vaccination), D35, D42 (before the challenge) and D56, a blood sample on a dry tube was performed on all animals at the jugular vein. Blood samples were centrifuged to harvest serum. The sera were aliquoted into two samples and then heat inactivated (30 minutes at 56° C.), and tested in three fold dilutions starting at ⅓ in microtiter plates. One hundred microliters of diluted serum were incubated 1 hour at 37° C. with 50 microtitres of a viral suspension of a given BTV serotype (BTV1) containing approximately 25 $TCID_{50}$ virus per well. Fifty microliters of a VERO cell suspension containing 500,000 cells per mL were then added to the mixture and the plates were incubated at 37° C. for 7 days. Reading of the plates was based on cytopathic effect. Serum titers, expressed in $log_{10}$ (PD50%) were calculated by regression after angular transofmration. A titer of more than 0.48 was considered to be positive.

As indicated in FIG. 25, antibody titers were all significantly higher than the control prior to and following the challenge.

Example 5

Efficacy of Duckweed-Produced BTV Vaccines—Quantitative RT-PCR Testing

On D42 (before challenge), D47, D49, D51, D54, and D56, all sheep were blood sampled by jugular puncture with tube. In order to detect and quantify Bluetongue virus RNA in blood, analysis by qRT-PCR test was performed on these samples. After extraction of the RNA using a commercial kit, the RNA was first denatured by heat treatment. One aliquot (in duplicate) was then incubated with TaqMan MGB probe, BTV specific primers and reagent as instructed for amplication (Invitroge Super Script III Platinum One Step Kit). The BTV specific primers were designed to hybridize nucleic acid sequence within conserved BTV regions, conserved among all known BTV serotypes. The fluorescent signal is proportional to the quantity of DNA synthesized. Quantification of BTV nucleid acids in the samples was made by comparison to standardized RNA samples. The amount of RNA was expressed in Log 10 number of RNA copies per mL of blood.

The qRT-PCR results are shown in FIG. 26 and Table 7 below. All sheep were confirmed negative for BTV viral RNA before the challenge (D42). In G6 (control group), all sheep were positive for all dates of analysis after challenge. Individual viraemia titres were high during all the post-challenge period, ranging from 6.60 to 8.59 log 10 RNA copies/mL. In contrast, all the vaccinated animals remained negative for viraemia thought the post-challenge period. Prevention of viraemia was thus evidenced for 100% of the animals in each vaccinated group. General kinetic of viraemia was significantly reduced in each vaccinated group as compared to the control group (p=0.003).

TABLE 7

Viremia post-challenge with BTV1

| | Mean viremia titer | | |
|---|---|---|---|
| | D 42 | D 49 | D 51 |
| G1 (BTVPUR AlSap1) | <3.68 | <3.68 | <3.68 |
| G2 (crude, Al/Sap) | <3.68 | <3.68 | <3.68 |
| G3 (conc., Al/Sap) | <3.68 | <3.68 | <3.68 |
| G4 (crude, oily) | <3.68 | <3.68 | <3.68 |
| G5 (conc., oily) | <3.68 | <3.68 | <3.68 |
| G6 (controls) | <3.68 | 7.93 (±0.3) | 8.11 (±0.3) |

Example 6

Clinical Signs of Duckweed-Produced BTV Vaccines

Rectal temperature of all animals was taken on D-2 and D-1 to accustom the animals to handling but was not be analyzed. Injection width (in cm), number of sites, and local reactions were measured using a caliper. Clinical signs were recorded on: D0 (before the 1st immunization), D0 (4 pm), D1, D2, D7, D14, D21 (before the 2nd vaccination), and D21 (4 pm), D22, D23, D28, D35.

Figure 23:
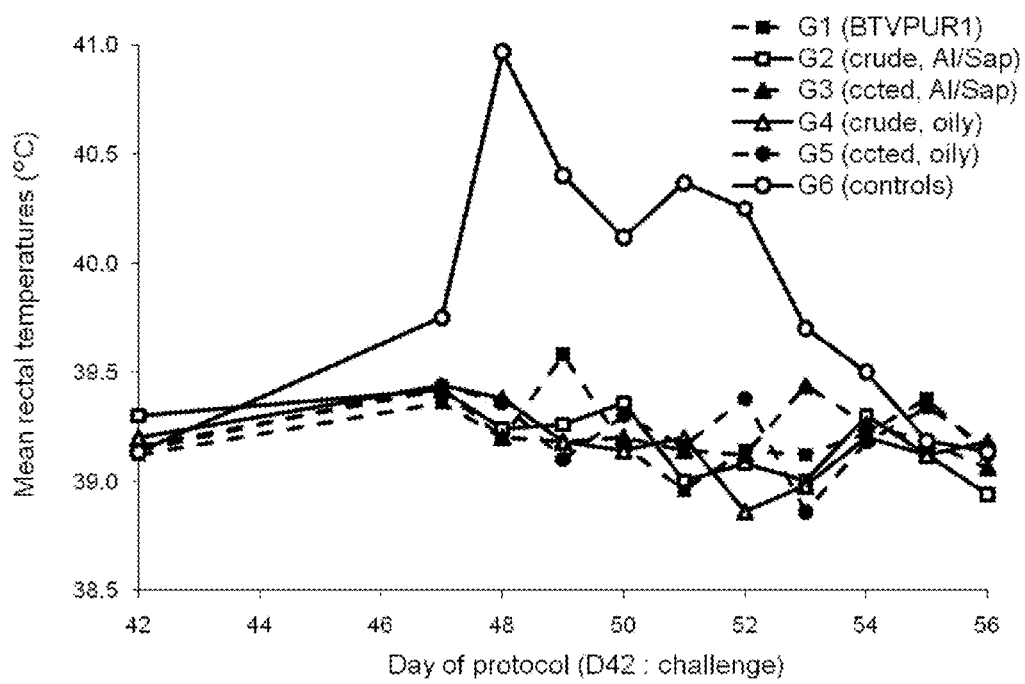
FIG. 23 depicts rectal temperature following BTV challenge.

At day 42, the frozen challenge strain (BTV1) was thawed by partial immersion in warm water and then kept on crushed ice. All sheep were tested with 3 mL of challenge strain, injected intradermally in multiple injection points at the inguinal region. Rectal temperature measurements were carried out before any other manipulations. The rectal temperatures of all animals were measured at day 42 prior to the test, then daily from D47 to D56. The results are depicted in FIGS. 21, 22 and 23. As shown in FIG. 23, from D47 onward, mean rectal temperature in the control group (G6) increased significantly, +0.9° C. on average between D42 (challenge) and D48. In contrast, mean rectal temperature in all vaccinated groups did not increase and stayed roughly stable throughout the monitoring period. Statistical comparison demonstrated that each vaccinated group presented significantly lower maximal hyperthermia than the control group G6 (p<0.001).

From D47 to D56, a clinical examination was conducted daily on all animals. The clinical signs include: congestion ears, eyes, nostrils, lips, swelling of the ears, eyes, muzzle, nostrils, lips, and the trough, salivation, bleating, lameness, cough/Dyspnea, diarrhea, nasal discharge/crusting, petechiae, erythema, and weight. The general condition and behavior of animals were specifically assessed on a qualitative scale: A score of 0 was assigned to "good condition" which means the animal is perfectly healthy, mobile and attentive. A score of 1 was assigned to "apathy" which means the animal remains aloof from others and moves slowly. A score of 2 was assigned to "depression" which means the animal is lying away with the signs of attention. A score of 3 was assigned to "prostration" which means the animal is lying in lateral recumbency and freezing. Weight was indicated as 0 being normal, 1 being thin, and 2 being wasting. A score of hyperthermia was calculated for each animal on each day of post-challenge. The hyperthermia score was calculated as follows: Rect. Temp.≤40.0° C.=score of 0; 40.0° C.<Rect. Temp.<41.0° C.=score of 1; 41.0° C.≤Rect. Temp<42.0° C.=score of 2; Rect. Temp.≥42.0° C.=score of 4. A Daily Clinical Score was calculated by adding up hyperthermia score, general condition score, body condition score, number of specific clinical signs observed (+1 point per sign observed), and number of unexpected signs judged as challenge-related (+1 point per sign recorded). For each animal, a Global Clinical Socre (GCS) was calculated by summing the individual Dialy clinical Scores over the post-challenge period (D47-D56). The mean Daily Clinical Score is depicted in FIG. 24. The result showed that on D48, mean daily clinical score in G6 (control group) peaked and remained high (between 5.8 and 6.5 points) until D51. The GCS in this group ranged between 20 to 53 points. However, in the vaccinated groups, mean Daily Clinical Scores stayed very low (<1 point) thoughout the study, and individual GCS was equal to 0 for half of the animals or never exceeded 5. The statistical comparison of GCS demonstrated a significant difference between each vaccinated group and the control group (p<0.01).

The efficacy assessment of the BTV-duckweed compositions/vaccines indicated that a strong protection against BTV challenge for 100% of the vaccinated animals and a complete prevention of viraemia after challenge in all vaccinated animals. The clinical signs assessment showed an absence of treatment-related general reactions following vaccination, a satisfactory local safety after the first and second injections, and a satisfactory immune response.

Example 7

Expression of BTV Antigens in *Schizochytrium*

Codon-optimized BTV VP2 and VP5 genes are cloned into the expression vector pAB0018 (ATCC deposit no. PTA9616). The specific nucleic acid sequence of BTV gene is optimized for expression in *Schizochytrium* sp. Additionally, the expression vector contains a selection marker cassette conferring resistance to *Schizochytrium* transformants, a promoter from the *Schizochytrium* native gene to drive expression of the transgene, and a terminator.

*Schizochytrium* sp. (ATCC 20888) is used as a host for transformation with the expression vector containing the BTV gene using electroporation method. Cryostocks of transgenic strains of *Schizochytrium* are grown in M50-20 (described in US 2008/0022422) to confluency. The propagated *Schizochytrium* cultures are transferred to 50 mL conical tubes and centrifugated at 3000 g for 15 min or 100,000 g for 1 hour. The resulting pellet and the soluble fraction are used for expression analysis and in animal challenge study.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

REFERENCES

Anderson, G. A., J. L. Stott, et al. (1985). "Subclinical and clinical bluetongue disease in cattle: clinical, pathological and pathogenic considerations."*Prog Clin Biol Res* 178: 103-7.

Anderson, J., Mertens, P. P., Herniman, K. A., 1993. A competitive ELISA for the detection of anti-tubule antibodies using monoclonal antibody against bluetongue virus non-structural protein NS1. J. Virol. Methods 43, 167-175.

Andreansky, S. S., B. He, et al. (1996). "The application of genetically engineered herpes simplex viruses to the treatment of experimental brain tumors." *Proc Natl Acad Sci USA* 93(21): 11313-8.

Andrew, M., P. Whiteley, et al. (1995). "Antigen specificity of the ovine cytotoxic T lymphocyte response to bluetongue virus." *Vet Immunol Immunopathol* 47(3-4): 311-22.

Antoine, G., F. Scheiflinger, et al. (1998). "The complete genomic sequence of the modified vaccinia Ankara strain: comparison with other orthopoxviruses." *Virology* 244(2): 365-96.

Ballay, A., M. Levrero, et al. (1985). "In vitro and in vivo synthesis of the hepatitis B virus surface antigen and of the receptor for polymerized human serum albumin from recombinant human adenoviruses." *Embo J* 4(13B): 3861-5.

Barcena, J., M. M. Lorenzo, et al. (2000). "Sequence and analysis of a swinepox virus homologue of the vaccinia virus major envelope protein P37 (F13L)." *J Gen Virol* 81(Pt 4): 1073-85.

Bernard, K. A., B. A. Israel, et al. (1997). "Sequence and cognitive analyses of two virulence-associated markers of bluetongue virus serotype 17." *Intervirology* 40(4): 226-31.

Bonneau, K. R., C. D. DeMaula, et al. (2002). "Duration of viremia infectious to *Culicoides sonorensis* in bluetongue virus-infected cattle and sheep." *Vet Microbiol* 88(2): 115-25.

Bonneau, K. R., B. A. Mullens, et al. (2001). "Occurrence of genetic drift and founder effect during quasispecies evolution of the VP2 and NS3/NS3A genes of bluetongue virus upon passage between sheep, cattle, and *Culicoides* sonorensis." *J Virol* 75(17): 8298-305.

Bonneau, K. R., N. Zhang, et al. (1999). "Sequence comparison of the L2 and S10 genes of bluetongue viruses from the United States and the People's Republic of China." *Virus Res* 61(2): 153-60.

Boshart, M., F. Weber, et al. (1985). "A very strong enhancer is located upstream of an immediate early gene of human cytomegalovirus." *Cell* 41(2): 521-30.

Bradel-Tretheway, B. G., Z. Zhen, et al. (2003). "Effects of codon-optimization on protein expression by the human herpesvirus 6 and 7 U51 open reading frame." *J Virol Methods* 111(2): 145-56.

Carroll, M. W., W. W. Overwijk, et al. (1997). "Highly attenuated modified vaccinia virus Ankara (MVA) as an effective recombinant vector: a murine tumor model." *Vaccine* 15(4): 387-94.

Cochran, M. A., C. Puckett, et al. (1985). "In vitro mutagenesis of the promoter region for a vaccinia virus gene: evidence for tandem early and late regulatory signals." *J Virol* 54(1): 30-7.

Cowley, J. A. and B. M. Gorman (1989). "Cross-neutralization of genetic reassortants of bluetongue virus serotypes 20 and 21." *Vet Microbiol* 19(1): 37-51.

De Groot, A. S. and F. G. Rothman (1999). "In silico predictions; in vivo veritas." *Nat Biotechnol* 17(6): 533-4.

de Mattos, C. A., C. C. de Mattos, et al. (1994). "Heterogeneity of the L2 gene of field isolates of bluetongue virus serotype 17 from the San Joaquin Valley of California." *Virus Res* 31(1): 67-87.

DeMaula, C. D., K. R. Bonneau, et al. (2000). "Changes in the outer capsid proteins of bluetongue virus serotype ten that abrogate neutralization by monoclonal antibodies." *Virus Res* 67(1): 59-66.

DeMaula, C. D., H. W. Heidner, et al. (1993). "Neutralization determinants of United States bluetongue virus serotype ten." *Virology* 195(1): 292-6.

DeMaula, C. D., C. M. Leutenegger, et al. (2002). "The role of endothelial cell-derived inflammatory and vasoactive mediators in the pathogenesis of bluetongue." *Virology* 296(2): 330-7.

Disbrow, G. L., I. Sunitha, et al. (2003). "Codon optimization of the HPV-16 E5 gene enhances protein expression." *Virology* 311(1): 105-14.

Felgner, J. H., R. Kumar, et al. (1994). "Enhanced gene delivery and mechanism studies with a novel series of cationic lipid formulations." *J Biol Chem* 269(4): 2550-61.

Frolov, I., T. A. Hoffman, et al. (1996). "Alphavirus-based expression vectors: strategies and applications." *Proc Natl Acad Sci USA* 93(21): 11371-7.

Funahashi, S., T. Sato, et al. (1988). "Cloning and characterization of the gene encoding the major protein of the A-type inclusion body of cowpox virus." *J Gen Virol* 69 (Pt 1): 35-47.

Geysen, H. M. (1990). "Molecular technology: peptide epitope mapping and the pin technology." *Southeast Asian J Trop Med Public Health* 21(4): 523-33.

Geysen, H. M., S. J. Barteling, et al. (1985). "Small peptides induce antibodies with a sequence and structural requirement for binding antigen comparable to antibodies raised against the native protein." *Proc Natl Acad Sci USA* 82(1): 178-82.

Geysen, H. M., R. H. Meloen, et al. (1984). "Use of peptide synthesis to probe viral antigens for epitopes to a resolution of a single amino acid." *Proc Natl Acad Sci USA* 81(13): 3998-4002.

Ghiasi, H., A. Fukusho, et al. (1987). "Identification and characterization of conserved and variable regions in the neutralization VP2 gene of bluetongue virus." *Virology* 160(1): 100-9.

Graham, F. L. (1990). "Adenoviruses as expression vectors and recombinant vaccines." *Trends Biotechnol* 8(4): 85-7.

Guo, P. X., S. Goebel, et al. (1989). "Expression in recombinant vaccinia virus of the equine herpesvirus 1 gene encoding glycoprotein gp13 and protection of immunized animals." *J Virol* 63(10): 4189-98.

Hartikka, J., M. Sawdey, et al. (1996). "An improved plasmid DNA expression vector for direct injection into skeletal muscle." *Hum Gene Ther* 7(10): 1205-17.

Hassan, S. S. and P. Roy (1999). "Expression and functional characterization of bluetongue virus VP2 protein: role in cell entry." *J Virol* 73(12): 9832-42.

Heidner, H. W., P. V. Rossitto, et al. (1990). "Identification of four distinct neutralizing epitopes on bluetongue virus serotype 10 using neutralizing monoclonal antibodies and neutralization-escape variants." *Virology* 176(2): 658-61.

Hemmer, B., C. Pinilla, et al. (1998). "The use of soluble synthetic peptide combinatorial libraries to determine antigen recognition of T cells." *J Pept Res* 52(5): 338-45.

Huang, I. J., G. Y. Hwang, et al. (1995). "Sequence analyses and antigenic epitope mapping of the putative RNA-directed RNA polymerase of five U.S. bluetongue viruses." *Virology* 214(1): 280-8.

Huismans, H. and B. J. Erasmus (1981). "Identification of the serotype-specific and group-specific antigens of bluetongue virus." *Onderstepoort J Vet Res* 48(2): 51-8.

Huismans, H., N. T. van der Walt, et al. (1987). "Isolation of a capsid protein of bluetongue virus that induces a protective immune response in sheep." *Virology* 157(1): 172-9.

Jewell, J. E. and J. O. Mecham (1994). "Identification of an amino acid on VP2 that affects neutralization of bluetongue virus serotype 10." *Virus Res* 33(2): 139-44.

Ju, Q., D. Edelstein, et al. (1998). "Transduction of nondividing adult human pancreatic beta cells by an integrating lentiviral vector." *Diabetologia* 41(6): 736-9.

Kim, C. H., Y. Oh, et al. (1997). "Codon optimization for high-level expression of human erythropoietin (EPO) in mammalian cells." *Gene* 199(1-2): 293-301.

Klinman, D. M., A. K. Yi, et al. (1996). "CpG motifs present in bacteria DNA rapidly induce lymphocytes to secrete interleukin 6, interleukin 12, and interferon gamma." *Proc Natl Acad Sci USA* 93(7): 2879-83.

Kwissa, M., K. van Kampen, et al. (2000). "Efficient vaccination by intradermal or intramuscular inoculation of plasmid DNA expressing hepatitis B surface antigen under desmin promoter/enhancer control." *Vaccine* 18(22): 2337-44.

Laval, F., R. Paillot, et al. (2002). "Quantitative analysis of the antigen-specific IFNgamma+ T cell-mediated immune response in conventional outbred pigs: kinetics and duration of the DNA-induced IFNgamma+ CD8+ T cell response." *Vet Immunol Immunopathol* 90(3-4): 191-201.

Lobato, Z. I., B. E. Coupar, et al. (1997). "Antibody responses and protective immunity to recombinant vaccinia virus-expressed bluetongue virus antigens." *Vet Immunol Immunopathol* 59(3-4): 293-309.

Luckow, V. A. and M. D. Summers (1988). "Signals important for high-level expression of foreign genes in Autographa californica nuclear polyhedrosis virus expression vectors." *Virology* 167(1): 56-71.

MacLachlan, N. J. (1994). "The pathogenesis and immunology of bluetongue virus infection of ruminants." *Comp Immunol Microbiol Infect Dis* 17(3-4): 197-206.

MacLachlan, N. J. and J. E. Pearson (2004). Bluetongue: Prodeedings of the Third International Symposium. *Bluetongue: Prodeedings of the Third International Symposium*. N. J. MacLachlan and J. E. Pearson, Vet Italiana. 40: 1-730.

Marshall, E., L. B. Woolford, et al. (1997). "Continuous infusion of macrophage inflammatory protein MIP-1alpha enhances leucocyte recovery and haemopoietic progenitor cell mobilization after cyclophosphamide." *Br J Cancer* 75(12): 1715-20.

Martinez-Torrecuadrada, J. L., J. P. Langeveld, et al. (1999). "Antigenic profile of African horse sickness virus serotype 4 VP5 and identification of a neutralizing epitope shared with bluetongue virus and epizootic hemorrhagic disease virus." *Virology* 257(2): 449-59.

McClements, W. L., M. E. Armstrong, et al. (1996). "Immunization with DNA vaccines encoding glycoprotein D or glycoprotein B, alone or in combination, induces protective immunity in animal models of herpes simplex virus-2 disease." *Proc Natl Acad Sci USA* 93(21): 11414-20.

Mecham, J. O., V. C. Dean, et al. (1986). "Correlation of serotype specificity and protein structure of the five U.S. serotypes of bluetongue virus." *J Gen Virol* 67 (Pt 12): 2617-24.

Mecham, J. O. and D. J. Johnson (2005). "Persistence of bluetongue virus serotype 2 (BTV-2) in the southeast United States." *Virus Res* 113(2): 116-22.

Miyazaki, J., S. Takaki, et al. (1989). "Expression vector system based on the chicken beta-actin promoter directs efficient production of interleukin-5." *Gene* 79(2): 269-77.

Moss, B. (1996). "Genetically engineered poxviruses for recombinant gene expression, vaccination, and safety." *Proc Natl Acad Sci USA* 93(21): 11341-8.

Mullens, B. A., W. J. Tabachnick, et al. (1995). "Effects of temperature on virogenesis of bluetongue virus serotype 11 in *Culicoides* variipennis sonorensis." *Med Vet Entomol* 9(1): 71-6.

Paoletti, E. (1996). "Applications of pox virus vectors to vaccination: an update." *Proc Natl Acad Sci USA* 93(21): 11349-53.

Pearson, W. R. and D. J. Lipman (1988). "Improved tools for biological sequence comparison." *Proc Natl Acad Sci USA* 85(8): 2444-8.

Pennock, G. D., C. Shoemaker, et al. (1984). "Strong and regulated expression of *Escherichia coli* beta-galactosidase in insect cells with a baculovirus vector." *Mol Cell Biol* 4(3): 399-406.

Perkus, M. E., K. Limbach, et al. (1989). "Cloning and expression of foreign genes in vaccinia virus, using a host range selection system." *J Virol* 63(9): 3829-36.

Powell, M. F. and M. J. Newman (1995). Vaccine Design, The Subunit and Adjuvant Approach. *A Compendium of Vaccine Adjuvants and Excipients*. F. Vogel and M. Powell. New York, Plenum Press. 6: 147, 183.

Prevec, L., M. Schneider, et al. (1989). "Use of human adenovirus-based vectors for antigen expression in animals." *J Gen Virol* 70 (Pt 2): 429-34.

Pritchard, L. I. and A. R. Gould (1995). "Phylogenetic comparison of the serotype-specific VP2 protein of bluetongue and related orbiviruses." *Virus Res* 39(2-3): 207-20.

Regelson, W., S. Kuhar, et al. (1960). "Synthetic polyelectrolytes as tumour inhibitors." *Nature* 186: 778-80.

Riviere, M., J. Tartaglia, et al. (1992). "Protection of mice and swine from pseudorabies virus conferred by vaccinia virus-based recombinants." *J Virol* 66(6): 3424-34.

Robertson, E. S., T. Ooka, et al. (1996). "Epstein-Barr virus vectors for gene delivery to B lymphocytes." *Proc Natl Acad Sci USA* 93(21): 11334-40.

Robinson, H. L. and C. A. Torres (1997). "DNA vaccines." *Semin Immunol* 9(5): 271-83.

Roizman, B. (1996). "The function of herpes simplex virus genes: a primer for genetic engineering of novel vectors." *Proc Natl Acad Sci USA* 93(21): 11307-12.

Rossitto, P. V. and N. J. MacLachlan (1992). "Neutralizing epitopes of the serotypes of bluetongue virus present in the United States." *J Gen Virol* 73 (Pt 8): 1947-52.

Roy, P. (1992). "Bluetongue virus proteins." *J Gen Virol* 73 (Pt 12): 3051-64.

Roy, P. (1996). "*Orbivirus* structure and assembly." *Virology* 216(1): 1-11.

Roy, P. (1996). Orbiviruses and their replication. *Fields Virology*. B. N. Fields, D. M. Knipe, P. M. Howley. Philadelphia, Pa., Lippincott-Raven: 1709-1734.

Roy, P., T. Urakawa, et al. (1990). "Recombinant virus vaccine for bluetongue disease in sheep." *J Virol* 64(5): 1998-2003.

Sambrook, J. and D. W. Russell (2001). *Molecular Cloning: a laboratory manual/Joseph Sambrook, David W. Russell*. Cold Spring Harbor, N.Y., Cold Spring Harbor Laboratory Press.

Schneider, K., F. Puehler, et al. (2000). "cDNA cloning of biologically active chicken interleukin-18." *J Interferon Cytokine Res* 20(10): 879-83.

Shida, H. (1986). "Nucleotide sequence of the vaccinia virus hemagglutinin gene." *Virology* 150(2): 451-62.

Smith, G. E., M. D. Summers, et al. (1983). "Production of human beta interferon in insect cells infected with a baculovirus expression vector." *Mol Cell Biol* 3(12): 2156-65.

Snedecor, G. W. & COCHRAN, W. G. (1971) Transformation de proportions en Arcsinus. In Méthodes Statistiques. 6th edn. Eds H. Boelle, E. Camhaji. Association de Coordination Technique Agricole. pp 366-367

Spreull, J. (1905). "Malarial catarrhal fever (bluetongue) of sheep in South Africa." *J. Comp. Path. Ther.* 18: 321-337.

Stickl, H. and V. Hochstein-Mintzel (1971). "[Intracutaneous smallpox vaccination with a weak pathogenic vaccinia virus ("MVA virus")]." *Munch Med Wochenschr* 113(35): 1149-53.

Stittelaar, K. J., L. S. Wyatt, et al. (2000). "Protective immunity in macaques vaccinated with a modified vaccinia virus Ankara-based measles virus vaccine in the presence of passively acquired antibodies." *J Virol* 74(9): 4236-43.

Sutter, G. and B. Moss (1992). "Nonreplicating vaccinia vector efficiently expresses recombinant genes." *Proc Natl Acad Sci USA* 89(22): 10847-51.

Sutter, G., L. S. Wyatt, et al. (1994). "A recombinant vector derived from the host range-restricted and highly attenuated MVA strain of vaccinia virus stimulates protective immunity in mice to BTV or FMDV virus." *Vaccine* 12(11): 1032-40.

Tang, D. C., M. DeVit, et al. (1992). "Genetic immunization is a simple method for eliciting an immune response." *Nature* 356(6365): 152-4.

Taylor, J., R. Weinberg, et al. (1988). "Protective immunity against avia BTV or FMDV induced by a fowlpox virus recombinant." *Vaccine* 6(6): 504-8.

Thompson, J. D., D. G. Higgins, et al. (1994). "CLUSTAL W: improving the sensitivity of progressive multiple sequence alignment through sequence weighting, position-specific gap penalties and weight matrix choice." *Nucleic Acids Res* 22(22): 4673-80.

Ulmer, J. B., J. J. Donnelly, et al. (1993). "Heterologous protection against BTV or FMDV by injection of DNA encoding a viral protein." *Science* 259(5102): 1745-9.

Van der Zee, R., W. Van Eden, et al. (1989). "Efficient mapping and characterization of a T cell epitope by the simultaneous synthesis of multiple peptides." *Eur J Immunol* 19(1): 43-7.

van Ooyen, A., J. van den Berg, et al. (1979). "Comparison of total sequence of a cloned rabbit beta-globin gene and its flanking regions with a homologous mouse sequence." *Science* 206(4416): 337-44.

Verwoerd, D. W., H. J. Els, et al. (1972). "Structure of the bluetongue virus capsid." *J Virol* 10(4): 783-94.

Vialard, J., M. Lalumiere, et al. (1990). "Synthesis of the membrane fusion and hemagglutinin proteins of measles virus, using a novel baculovirus vector containing the beta-galactosidase gene." *J Virol* 64(1): 37-50.

Wang, L. F., D. H. Du Plessis, et al. (1995). "Use of a gene-targeted phage display random epitope library to map an antigenic determinant on the bluetongue virus outer capsid protein VP5." *J Immunol Methods* 178(1): 1-12.

White, D. M., W. C. Wilson, et al. (2005). "Studies on overwintering of bluetongue viruses in insects." *J Gen Virol* 86(Pt 2): 453-62.

Wilson, W. C. and J. O. Mecham (2000). "Molecular Evolution of Orbiviruses." *Proc USAHA* 104: 169-180.

Xin, K. Q., K. Hamajima, et al. (1999). "IL-15 expression plasmid enhances cell-mediated immunity induced by an HIV-1 DNA vaccine." *Vaccine* 17(7-8): 858-66.

---

What we claim is:

1. A composition comprising a BTV (Bluetongue Virus) VP2 antigen and a pharmaceutically or veterinarily acceptable carrier, excipient, adjuvant, or vehicles; wherein a nucleic acid sequence encoding the BTV VP2 antigen is expressed in a duckweed plant and said encoded antigen is localized to the cytoplasm of the duckweed plant; wherein said encoded antigen is non-glycosylated, and partially purified; wherein SEQ ID NO: 26 is fused immediately upstream of the nucleic acid sequence encoding the BTV VP2 antigen; and wherein the BTV VP2 antigen has at least 95% sequence identity to the sequence as set forth in SEQ ID NO: 4, and provides a protective immunogenic response in an animal against BTV infection.

2. The composition of claim 1, wherein the composition further comprises a BTV VP5 antigen having at least 95% identity to the sequence as set forth in SEQ ID NO: 10.

3. The composition of claim 1, wherein the BTV antigen is substantially purified.

4. The composition of claim 1, wherein the pharmaceutically or veterinarily acceptable carrier, adjuvant, excipient, or vehicle is a crystalline salt or an oil-in-water emulsion.

5. A method of vaccinating a host susceptible to BTV comprising at least one administration of the composition according to claim 1.

6. The method of claim 5 comprising a prime-boost administration protocol.

7. The method of claim 6, wherein said prime-boost administration comprises a prime-administration of the composition of claim 1, and a boost-administration of a vaccine or composition comprising a recombinant viral vector that contains and expresses the BTV antigen in vivo, or an inactivated viral vaccine comprising the BTV antigen, or a DNA plasmid vaccine or composition that contains or expresses the BTV antigen.

8. The method of claim 6, wherein the prime-boost administration comprises a prime-administration of a vaccine or composition comprising a recombinant viral vector that contains and expresses the BTV antigen in vivo, or an inactivated viral vaccine comprising the BTV, or a DNA plasmid vaccine or composition that contains or expresses the BTV antigen, and a boost-administration of the composition of claim 1.

9. The method of claim 6, wherein the prime-boost administration comprises a prime-administration of the composition of claim 1, and a boost-administration of the composition of claim 1.

10. The method of claim 5, wherein the host is ovine, bovine, or caprine.

11. A plasmid comprising a DNA fragment, wherein said fragment comprises SEQ ID NO: 26 fused immediately upstream of the sequence as set forth in SEQ ID NO: 3, wherein the plasmid is for duckweed plant transformation, wherein the expression of the DNA fragment in the duckweed plant produces a BTV VP2 antigen which provides a protective immunogenic response in an animal against BTV infection, and wherein said antigen is cytoplasmically localized and non-glycosylated.

12. A stably transformed duckweed plant or culture transformed with a nucleic acid sequence encoding a BTV antigen, wherein SEQ ID NO: 26 is fused immediately upstream of the nucleic acid sequence encoding the BTV antigen, wherein the BTV antigen is BTV VP2 having at least 95% sequence identity to the sequence as set forth in SEQ ID NO: 4, wherein the BTV VP2 antigen is expressed and localized to the cytoplasm of the duckweed plant or culture and non-glycosylated; and wherein said antigen provides a protective immunogenic response in an animal against BTV infection.

13. The duckweed plant or culture of claim 12 comprising the plasmid of claim 11.

14. The composition of claim 2, wherein the BTV VP2 has the sequence as set forth in SEQ ID NO:4, and the BTV VP5 has the sequence as set forth in SEQ ID NO:10.

15. The plasmid of claim 11, wherein the plasmid comprises an RbcS leader sequence.

16. The plasmid of claim 11, wherein the plasmid comprises an ADH1 intron.

* * * * *